United States Patent
Bae et al.

(10) Patent No.: US 8,835,458 B2
(45) Date of Patent: Sep. 16, 2014

(54) QUINOLINE OR QUINAZOLINE DERIVATIVES WITH APOPTOSIS INDUCING ACTIVITY ON CELLS

(75) Inventors: In Hwan Bae, Hwaseong-si (KR); Eun Young Byun, Hanam-si (KR); Hae Kyoung Ju, Seoul (KR); Ji Young Song, Seoul (KR); Seung Hyun Jung, Goyang-si (KR); Seung Ah Jun, Busan (KR); Ho Seok Kim, Hwaseong-si (KR); Young Hee Jung, Seoul (KR); Mi Yon Shim, Yangpyeong-gun (KR); Young Gil Ahn, Seongnam-si (KR); Maeng Sup Kim, Seoul (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 13 days.

(21) Appl. No.: 13/818,478

(22) PCT Filed: Aug. 31, 2011

(86) PCT No.: PCT/KR2011/006458
§ 371 (c)(1),
(2), (4) Date: Feb. 22, 2013

(87) PCT Pub. No.: WO2012/030160
PCT Pub. Date: Mar. 8, 2012

(65) Prior Publication Data
US 2013/0165386 A1 Jun. 27, 2013

(30) Foreign Application Priority Data
Aug. 31, 2010 (KR) .................. 10-2010-0084731

(51) Int. Cl.
| | |
|---|---|
| *C07D 215/42* | (2006.01) |
| *C07D 239/94* | (2006.01) |
| *A61K 31/4709* | (2006.01) |
| *A61K 31/195* | (2006.01) |
| *C07K 5/02* | (2006.01) |
| *C07D 403/12* | (2006.01) |
| *C07K 5/083* | (2006.01) |
| *A61K 31/495* | (2006.01) |

(52) U.S. Cl.
CPC ............... *C07K 5/02* (2013.01); *C07D 215/42* (2013.01); *A61K 31/4709* (2013.01); *A61K 31/495* (2013.01); *C07D 239/94* (2013.01); *C07D 403/12* (2013.01); *C07K 5/0806* (2013.01)
USPC ...... 514/311; 514/313; 514/314; 514/266.21; 514/266.23; 544/284; 546/159

(58) Field of Classification Search
CPC ............... C07D 215/42; C07D 239/94; A61K 31/4709; A61K 31/495
USPC ............... 514/311, 313, 314, 266.21, 266.23; 544/284; 546/159
See application file for complete search history.

(56) References Cited

U.S. PATENT DOCUMENTS

| | | | |
|---|---|---|---|
| 7,456,209 B2 * | 11/2008 | Condon et al. ................ 514/415 |
| 7,968,590 B2 * | 6/2011 | Condon et al. ................ 514/422 |
| 2006/0025347 A1 | 2/2006 | Condon et al. | |
| 2008/0016893 A1 | 1/2008 | Hayase et al. | |
| 2008/0079735 A1 | 4/2008 | Selwan et al. | |

FOREIGN PATENT DOCUMENTS

| | | |
|---|---|---|
| WO | 2008/016893 A1 | 2/2008 |
| WO | 2008/079735 A1 | 7/2008 |

OTHER PUBLICATIONS

International Searching Authority International Search Report for PCT/KR2011/006458 dated Apr. 30, 2012.
International Searching Authority Written Opinion for PCT/KR2011/006458 dated Apr. 30, 2012.
Gonzalez-Lopez, Marcos, et al., Design, synthesis and evaluation of monovalent Smac mimetics that bind to the BIR2 domain of the anti-apoptotic protein XIAP, Bioorganic & Medicinal Chemistry Letters 21, 2011, pp. 4332-4336.
European Patent Office, European Search Report for EP11822135.7 dated Jan. 30, 2014.

* cited by examiner

*Primary Examiner* — D M Seaman
(74) *Attorney, Agent, or Firm* — Sughrue Mion, PLLC

(57) ABSTRACT

Provided is a pharmaceutical composition comprising, as an active ingredient, a quinoline or quinazoline derivative of formula (I), a pharmaceutically acceptable salt, an isomer, a hydrate, and a solvate thereof, which is effective in the prevention and treatment of a cancer, inflammation, autoimmune diseases or neurodegenerative disorders which are induced by the overexpression of inhibitor of apoptosis proteins (IAPs).

14 Claims, No Drawings

QUINOLINE OR QUINAZOLINE DERIVATIVES WITH APOPTOSIS INDUCING ACTIVITY ON CELLS

CROSS REFERENCE TO RELATED APPLICATIONS

This application is a National Stage of International Application No. PCT/KR2011/006458 filed Aug. 31, 2011, claiming priority based on Korean Patent Application No. 10-2010-0084731 filed Aug. 31, 2010, the contents of all of which are incorporated herein by reference in their entirety.

FIELD OF THE INVENTION

The present invention relates to a novel quinoline or quinazoline derivative which is effective in the prevention or treatment of a cancer, inflammation, autoimmune diseases, or neurodegenerative disorders, which are induced by the overexpression of inhibitor of apoptosis proteins (IAPs); and a pharmaceutical composition comprising the same.

BACKGROUND OF THE INVENTION

Apoptosis or programmed cell death plays an important role in homeostasis of multicellular organisms. This apoptosis maintains organisms by regulating the cell growth and death, but, if it is inhibited by some factors, there may result in pathological diversity including cancers, autoimmune diseases, neurodegenerative disorders, and others [see Thompson, C. B. *Science*, 267, 1456-1462 (1995); Hanahan, D. & Weinberg, R. A., *Cell*, 100, 57-70 (2000)].

In the tumor development stages, such regulatory step of apoptosis allows IAPs (inhibitor of apoptosis proteins) to accumulate within cells via overexpression, to inhibit programmed cell death of mutant cancer cells undergoing an apoptotic stage, which leads to the inhibition of the natural apoptotic mechanism in the processes of development, growth, and metastasis of cancer cells by various apoptosis signals (e.g., stimuli such as DNA damage, chemical agents, and ultraviolet) [see George L. M., *Biochemistry*, 41, 7344-7349, (2002); Yigong Shi, *Nature Rev. Mol. Cell. Bio.*, 5, 897-907, (2004)].

IAPs bind to and incapacitate caspases, a class of cysteine proteases involved in programmed cell death. Caspases bind to BIR (baculovirus IAP repeat) domain of IAPs, an approximately 70 amino acid zinc-binding motif. XIAP (human X chromosome encoded IAP), cIAP1 (cellular IAP1) and cIAP2 (cellular IAP2) each consists of three tandem adjoined BIR domains at the N-terminus, and other mammalian IAPs have one BIR domain. XIAP is the most effective caspase inhibitor among the IAPs class, which binds to both caspase-9 (the initiator caspase) and caspase 3/7 (the effector caspase), respectively. Even though the roles of cIAP1 and 2 in programmed cell death are still unknown, both bind to TNF-receptor 1 signaling complexes.

Smac/DIABLO (the second mitochondrial activator of caspase/direct IAP-binding protein with low pI), a polypeptide released from mitochondria during the apoptotic signal release, regulates the activities of IAPs by binding to the same sites to which IAPs bind. In addition, IAPs gene amplification and overexpression of IAPs have been found in many tumor cells.

For the above reasons, the resistance of tumor cells to apoptosis has been thought to be an important mechanism in tumor progression, and accordingly, there has been suggested that exploiting the difference between the mechanisms in tumor cells and those in normal cells may be as an effective anticancer therapeutic strategy. Further, such drugs must act selectively on cancer cells, exerting no adverse influence on normal cells.

Such drugs have been investigated by several international pharmaceutical manufacturers, as was disclosed in WO2008/073305A1, WO2008/073306A1, WO2008/016893A2, WO2006/107963A1, WO2006/113376A1, and WO2005/097791A1 by Novartis, WO2009/089502A1 and WO2008/079735A1 by Genetech, WO2007/131366A1 by Aegera, WO2008/014252A2 by TetraLogic, and others.

As to the methods for inhibiting IAPs, studies on Smac/DIABLO, a natural IAP inhibitory protein, structure mimetics are currently in progression. As a result, it has been found that the key sequence of alanine-valine-proline-isoleucine (Ala-Val-Pro-Ile, AVPI) is essential protein to bind with IAPs [see Yigong Shi, *Nature structural biology*, 8, 394-401, (2001)]. This key sequence (AVPI or AVPF) shows pharmacological activity of 120-500 nM in an in vitro assay, but failed to overcome its low cell permeability.

The present inventors have endeavored to search for compounds having AVPI properties of a natural IAP inhibitory sequence having good cell permeability, and to evaluate the activities of the compounds on cancer, inflammation, autoimmune diseases and neurodegenerative disorders. As a result, we have successfully identified a novel quinoline or quinazoline derivative having excellent, selective efficacies on IAPs.

SUMMARY OF THE INVENTION

Therefore, it is an object of the present invention to provide a novel compound and a pharmaceutical composition comprising the compound which selectively and effectively inhibits the growth of cancer cells, inflammatory diseases, autoimmune diseases and neurodegenerative disorders caused by inhibition of apoptosis, while having minimized adverse side effects.

In accordance with one aspect of the present invention, there is provided a compound selected from the group consisting of a quinoline or quinazoline derivative of Formula (I), and a pharmaceutically acceptable salt, an isomer, a hydrate, and a solvate thereof:

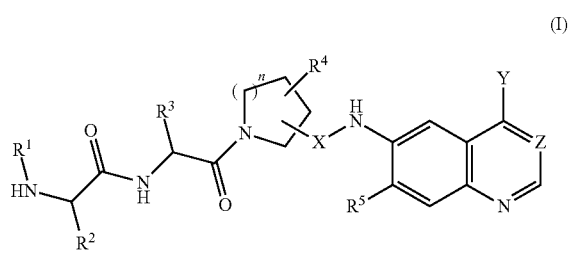

(I)

wherein,
Z is CH or N;
X is C(=O) or $CH_2$;
Y is hydrogen, $-NR^6R^7$, $-NR^6C(=O)R^7$, or $-NR^6C(=O)NR^6R^7$;
n is an integer ranging from 0 to 3;
$R^1$ is hydrogen, $C_{1-6}$alkyl, $C_{1-6}$alkanoyl, $C_{2-6}$alkenoyl, or $C_{2-6}$alkynoyl;
$R^2$ is hydrogen or $C_{1-3}$alkyl;
$R^3$ is hydrogen, $C_{1-6}$alkyl, $C_{3-6}$cycloalkyl, or $C_{3-6}$alkynyloxy$C_{1-4}$alkyl;

$R^4$ and $R^5$ are each independently hydrogen, —O($CH_2$)$_m$—$C_{1-6}$alkyl, —O($CH_2$)$_m$—$C_{3-6}$cycloalkyl, —O($CH_2$)$_m$—$C_{3-6}$heterocycloalkyl, —O($CH_2$)$_m$—$C_{5-10}$aryl, —O($CH_2$)$_m$—$C_{5-10}$heteroaryl or —O($CH_2$)$_m$—$C_{1-3}$alkoxy, in which m is an integer ranging from 0 to 3;

$R^6$ is hydrogen or $C_{1-6}$alkyl; and $R^7$ is hydrogen, $C_{1-8}$alkyl, —($CH_2$)$_l$—$C_{3-6}$cycloalkyl, —($CH_2$)$_l$—$C_{3-6}$heterocycloalkyl, —($CH_2$)$_l$—$C_{5-10}$aryl or —($CH_2$)$_l$—$C_{5-10}$heteroaryl, in which l is an integer ranging from 0 to 3; in which:

said $R^6$ and $R^7$ are optionally linked together to form a ring structure; and said $R^7$ is optionally substituted with one or more substituents selected from the group consisting of halogen, —$CF_3$, —$NO_2$, —CN, $C_{1-8}$alkyl, —($CH_2$)$_p$$NR^8R^9$, —($CH_2$)$_p$$OR^{10}$, —($CH_2$)$_p$C(=O)$R^{11}$, —($CH_2$)$_p$C(=O)$OR^{10}$, —($CH_2$)$_p$C(=O)$NR^8R^9$, —($CH_2$)$_p$$NR^8$C(=O)$R^{11}$, —($CH_2$)$_p$$SR^{12}$, —($CH_2$)$_p$S(=O)$R^{11}$, —($CH_2$)$_p$S(=O)$_2R^{11}$, and —($CH_2$)$_p$—$C_{3-6}$cycloalkyl, —($CH_2$)$_p$—$C_{3-6}$heterocycloalkyl, —($CH_2$)$_p$—$C_{1-10}$aryl and —($CH_2$)$_p$—$C_{5-10}$heteroaryl, in which p is an integer ranging from 0 to 3; in which:

said $R^8$, $R^9$, $R^{10}$, $R^{11}$ and $R^{12}$ are each independently halogen, —$CF_3$, —$NO_2$, —CN, $C_{1-6}$alkyl, —($CH_2$)$_q$—$C_{3-6}$cycloalkyl, —($CH_2$)$_q$—$C_{3-6}$heterocycloalkyl, —($CH_2$)$_q$—$C_{2-4}$alkenyl, —($CH_2$)$_q$—$C_{2-4}$alkynyl, —($CH_2$)$_q$—$C_{5-10}$aryl or —($CH_2$)$_q$—$C_{5-10}$heteroaryl, in which q is an integer ranging from 0 to 3; and said $R^8$ and $R^9$ are optionally linked together to form a ring structure.

In accordance with another aspect of the present invention, there is provided a pharmaceutical composition comprising said compound and a pharmaceutically acceptable carrier.

In accordance with a further aspect of the present invention, there is provided a pharmaceutical composition for preventing or treating a cancer, inflammation, an autoimmune disease or a neurodegenerative disorder, comprising said compound.

In accordance with a still further aspect of the present invention, there is provided a compound library comprising two or more of said compounds.

DETAILED DESCRIPTION OF THE INVENTION

The term 'halogen' as used herein refers to fluorine, chlorine, bromine or iodine, unless otherwise indicated.

The term 'alkyl' as used herein refers to straight, cyclic, or branched hydrocarbon residues, unless otherwise indicated.

The term 'cycloalkyl' as used herein refers to cyclic alkyls including cyclopropyl, and others, unless otherwise indicated.

The term 'aryl' as used herein refers to aromatic groups including phenyl, naphthyl, and others, unless otherwise indicated.

The term 'heterocycloalkyl' as used herein refers to cyclic alkyls including monocyclic, bicyclic alkyls, and others which contain heteroatoms selected from O, N and S, unless otherwise indicated. Examples of monoheterocycloalkyl include piperidinyl, morpholinyl, thiamorpholinyl, pyrrolidinyl, imidazolidinyl, tetrahydrofuranyl, piperazinyl and similar groups thereof, but not limited thereto.

The term 'heteroaryl' as used herein refers to aromatic groups including monocyclic or bicyclic groups, and others which contain heteroatoms selected from O, N and S, unless otherwise indicated. Examples of monocyclic heteroaryl include thiazolyl, oxazolyl, thiophenyl, furanyl, pyrrolyl, imidazolyl, isooxazolyl, pyrazolyl, triazolyl, thiadiazolyl, tetrazolyl, oxadiazolyl, pyridinyl, pyridazinyl, pyrimidinyl, pyrazinyl and similar groups thereof, but not limited thereto. Examples of bicyclic heteroaryl include indolyl, benzothiophenyl, benzofuranyl, benzimidazolyl, benzoxazolyl, benzisoxazolyl, benzthiazolyl, benzthiadiazolyl, benztriazolyl, quinolinyl, isoquinolinyl, furinyl, furopyridinyl and similar groups thereof, but not limited thereto.

The compound of the present invention may also form a pharmaceutically acceptable salt. Such salt may be a pharmaceutically acceptable nontoxic acid addition salt containing anion, but not limited thereto. For example, the salt may include acid addition salts formed by inorganic acids such as hydrochloric acid, sulfuric acid, nitric acid, phosphoric acid, hydrobromic acid, hydriodic acid, and others; organic carbonic acids such as tartaric acid, formic acid, citric acid, acetic acid, trichloroacetic acid, trifluoroacetic acid, gluconic acid, benzoic acid, lactic acid, fumaric acid, maleic acid, and others; and sulfonic acids such as methanesulfonic acid, benzenesulfonic acid, p-toluenesulonic acid, naphthalensulfonic acid, and others. Among them, acid addition salts formed by sulfuric acid, methanesulfonic acid or hydrohalogenic acid, and others are preferred.

Meanwhile, the compound of the present invention can have an asymmetric carbon center, and thus may be present in the form of R or S isomer, racemic compounds, diastereomeric mixture, or individual diastereomer, such entire isomers and mixtures being included within the scope of the present invention In addition, solvates and hydrates of the compound of formula (I) are included within the scope of the present invention.

In the quinoline or quinazoline derivative of formula (I) of the present invention, preferably, Z is CH or N; X is C(=O) or $CH_2$; R is hydrogen, methyl or acroyl; $R^2$ is methyl; $R^3$ is t-butyl, cyclohexyl or propazyloxyethyl; $R^4$ is hydrogen or benzyloxy; $R^5$ is hydrogen, methoxy, methoxyethyl or 3-tetrahydrofuranyloxyl; n is an integer ranging from 0 to 2; and Y is selected from the group consisting of hydrogen, amine, 4-bromo-2-fluoroaniline, 3-chloro-2-fluoroaniline, 3,4-dichloro-2-fluoroaniline, 5-chlorobenzo-[1,3]dioxol-4-amine, 2,4-difluoro-3-chloroaniline, 4-chloro-3-fluoroaminobenzene, phenylmethylamino, 2-chloro-$N^1$-p-tolylbenzene-1,4-diamine, 2-chloroaniline, 4-methoxyaniline, methylamine, piperidine, 2-methylaniline, 2,4-difluoroaniline, 2-methoxyaniline, N-methylaniline, 2-amino naphthalene, 2-amino pyridine, (S)-α-methylbenzylamine, 2,4-difluorobenzylamine, 3-chloro-4-(3-fluorobenzyloxy)aniline, cyclohexylamine, 4-biphenylamine, 4-phenoxyaniline, 2,3-difluoroaniline, dimethylamine, 2-trifluoromethylaniline, 1-phenylurea, 2-nitrileaniline, 3,4-dichloro-2-fluoro-N-methylaniline, 2-morpholinaniline, 1,2,3,4-tetrahydroquinoline, 2,3-dihydro-1H-inden-5-amine, 5-aminoquinoline, 6-aminoquinoline, 8-aminoquinoline, 1H-indazol-5-amine, 1-aminonaphthalene, acetamide, 4-fluoroaniline, 4-chloroaniline, 3-ethynylaniline, 3-chloroaniline, 3-methoxyaniline, 2,4-dichloroaniline, 2,6-difluoroaniline, 2,6-dichloro-3,5-dimethoxyaniline, 4-(4-ethylpiperazin-1-yl)aniline, benzamide, 4-dimethylaminoaniline, 4-diethylaminoaniline, 4-(pyrrolidin-1-yl)aniline, 4-(piperidin-1-yl)aniline, 4-(4-methylpiperazin-1-yl)aniline, 3-chloro-4-(4-ethylpiperazin-1-yl)aniline, 3-fluoro-4-(4-ethylpiperazin-1-yl)aniline, 4-(4-ethylpiperazin-1-yl)-3-(trifluoromethyl)aniline, N-(4-aminophenyl)acetamide, 4-aminopyridine, 4-amino-N-methylbenzamide, N-(4-aminophenyl)benzamide, N-(3-amino-4-chlorophenyl)acetamide, 1-(2-fluorophenyl)urea, 2,3-dichloroaniline, 2-bromo-4-fluoroaniline, 2-chloropyridin-3-amine, 2-chloro-N1,N1-diethylbenzene-1,4-diamine, 2-phenylethanamine, 3,5-dichloro-4-(pyridin-2-ylmethoxy) aniline, 3-chloro-4-(4-(cyclopropylmethyl)piperazin-1-yl) aniline, 3-chloro-4-(4-isopropylpiperazin-1-yl)aniline, 3-chloro-4-(4-propylpiperazin-1-yl)aniline, 3-chloro-4-(pyrrolidin-1-yl)aniline, 3-chloro-4-(pyridin-2-ylmethoxy) aniline, 3-chloro-4-(piperidin-1-yl)aniline, 3-chloro-4-morpholinoaniline, 3-fluoro-4-(piperidin-1-yl)aniline, 4-((1H-imidazol-1-yl)methyl)aniline, 4-((4-methylpiperazin-1-yl)sulfonyl)aniline, 4-([1,4'-bipiperidine]-1'-yl)aniline, 4-(1-methylpiperidin-3-yl)aniline, 4-(1-methylpiperidin-4-yl) aniline, 4-(1H-imidazol-1-yl)aniline, 4-(2-propyn-1-yloxy) aniline, 4-(4-(1-methylpiperidin-4-yl)piperazin-1-yl)aniline, 4-(4-(cyclopropylmethyl)piperazin-1-yl)-3-fluoroaniline, 4-(4-methylpiperidin-1-yl)cyclohexanamine, 4-(piperidin-1-ylmethyl)aniline, 4-morpholinoaniline, 4-bromo-2-chloroaniline, 4-bromo-3-chloro-2-fluoroaniline, 5-aminoindolin-2-one, 6-(prop-2-yn-1-yloxy)pyridin-3-amine, 6-chloropyridin-3-amine, 7-amino-2-methyl-4H-chromen-4-one, cyclohexylmethanamine, 4-(4-(4-methylpiperazin-1-yl)piperidin-1-yl)aniline, 3-chloro-4-(4-methylpiperazin-1-yl)aniline and N-(4-((3-fluoro-4-(4-methylpiperazin-1-yl) aniline. In addition, the pharmaceutically acceptable salt is preferably a hydrochloride.

The examples of preferred quinoline or quinazoline derivatives of the present invention are as follows. In addition to the derivatives, a pharmaceutically acceptable salt, an isomer, a hydrate, or a solvate thereof may be used.

1) (S)—N-(4-(3-chloro-2,4-difluorophenylamino)-7-methoxyquinazolin-6-yl)-1-((S)-3,3-dimethyl-2-((S)-2-(methylamino)propanamido)butanoyl)pyrrolidine-2-carboxamide;

2) (S)—N-(4-(3-chloro-2-fluorophenylamino)-7-(2-methoxyethoxy)quinazolin-6-yl)-1-((S)-3,3-dimethyl-2-((S)-2-(methylamino)propanamido)butanoyl)pyrrolidine-2-carboxamide;

3) (S)—N-(4-(5-chlorobenzo[d][1,3]dioxol-4-ylamino)-7-(2-methoxyethoxy)quinazolin-6-yl)-1-((S)-3,3-dimethyl-2-((S)-2-(methylamino)propanamido)butanoyl)pyrrolidine-2-carboxamide;

4) (S)—N-(4-(3-chloro-2-fluorophenylamino)quinazolin-6-yl)-1-((S)-3,3-dimethyl-2-((S)-2-(methylamino)propanamido)butanoyl)pyrrolidine-2-carboxamide;

5) (S)—N-(4-(3-chloro-4-fluorophenylamino)-7-(2-methoxyethoxy)quinazolin-6-yl)-1-((S)-3,3-dimethyl-2-((S)-2-(methylamino)propanamido)butanoyl)pyrrolidine-2-carboxamide;

6) (S)—N-(4-(3-chloro-2,4-difluorophenylamino)-7-(2-methoxyethoxy)quinazolin-6-yl)-1-((S)-3,3-dimethyl-2-((S)-2-(methylamino)propanamido)butanoyl)pyrrolidine-2-carboxamide;

7) (S)—N-(4-(3-chloro-2-fluorophenylamino)-7-(2-methoxyethoxy)quinazolin-6-yl)-1-((S)-3,3-dimethyl-2-((S)-2-(methylamino)propanamido)butanoyl)pyrrolidine-2-carboxamide;

8) (S)—N-(4-(3,4-dichloro-2-fluorophenylamino)-7-methoxyquinazolin-6-yl)-1-((S)-3,3-dimethyl-2-((S)-2-(methylamino)propanamido)butanoyl)pyrrolidine-2-carboxamide;

9) (S)—N-(4-(4-bromo-2-fluorophenylamino)-7-methoxyquinazolin-6-yl)-1-((S)-3,3-dimethyl-2-((S)-2-(methylamino)propanamido)butanoyl)pyrrolidine-2-carboxamide;

10) (S)-1-((S)-3,3-dimethyl-2-((S)-2-(methylamino)propanamido)butanoyl)-N-(4-(2-fluorophenylamino)-7-methoxyquinazolin-6-yl)pyrrolidine-2-carboxamide;

11) (S)—N-(4-phenylamino-7-methoxyquinazolin-6-yl)-1-((S)-3,3-dimethyl-2-((S)-2-(methylamino)propanamido) butanoyl)pyrrolidine-2-carboxamide;

12) (S)-1-((S)-2-((S)-2-aminopropanamido)-3,3-dimethylbutanoyl)-N-(4-(3-chloro-2,4-difluorophenylamino)-7-methoxyquinazolin-6-yl)pyrrolidine-2-carboxamide;

13) (S)-1-((S)-2-((S)-2-acrylamidopropanamido)-3,3-dimethylbutanoyl)-N-(4-(3-chloro-2,4-difluorophenylamino)-7-methoxyquinazolin-6-yl)pyrrolidine-2-carboxamide;

14) (S)—N-(4-(3-chloro-2,4-difluorophenylamino)-7-((S)-tetrahydrofuran-3-yloxy)quinazolin-6-yl)-1-((S)-3,3-dimethyl-2-((S)-2-(methylamino)propanamido)butanoyl) pyrrolidine-2-carboxamide;

15) (S)—N-(4-(3-chloro-2,4-difluorophenylamino)-7-methoxyquinazolin-6-yl)-1-((S)-2-cyclohexyl-2-((S)-2-(methylamino)propanamido)acetyl)pyrrolidine-2-carboxamide;

16) (S)—N-(4-(3-chloro-2,4-difluorophenylamino)-7-((R)-tetrahydrofuran-3-yloxy)quinazolin-6-yl)-1-((S)-3,3-dimethyl-2-((S)-2-(methylamino)propanamido)butanoyl) pyrrolidine-2-carboxamide;

17) (S)-1-((S)-3,3-dimethyl-2-((S)-2-(methylamino)propanamido)butanoyl)-N-(7-methoxy-4-(2,3,4-trifluorophenylamino)quinazolin-6-yl)pyrrolidine-2-carboxamide;

18) (S)—N-(4-benzylamino-7-methoxyquinazolin-6-yl)-1-((S)-3,3-dimethyl-2-((S)-2-(methylamino)propanamido) butanoyl)pyrrolidine-2-carboxamide;

19) (S)—N-(4-(3-chloro-4-(6-methylpyridin-3-yloxy)phenylamino)-7-methoxyquinazolin-6-yl)-1-((S)-3,3-dimethyl-2-((S)-2-(methylamino)propanamido)butanoyl)pyrrolidine-2-carboxamide;

20) (S)—N-(4-(3-chloro-2,4-difluorophenylamino)-7-methoxyquinazolin-6-yl)-1-((S)-3,3-dimethyl-2-((S)-2-(methylamino)propanamido)butanoyl)azetidine-2-carboxamide;

21) (S)—N-(4-(2-chlorophenylamino)-7-methoxyquinazolin-6-yl)-1-((S)-3,3-dimethyl-2-((S)-2-(methylamino) propanamido)butanoyl)pyrrolidine-2-carboxamide;

22) (S)—N-(4-(2-bromophenylamino)-7-methoxyquinazolin-6-yl)-1-((S)-3,3-dimethyl-2-((S)-2-(methylamino) propanamido)butanoyl)pyrrolidine-2-carboxamide;

23) (S)-1-((S)-3,3-dimethyl-2-((S)-2-(methylamino)propanamido)butanoyl)-N-(7-methoxy-4-(methylamino) quinazolin-6-yl)pyrrolidine-2-carboxamide;

24) (S)-1-((S)-3,3-dimethyl-2-((S)-2-(methylamino)propanamido)butanoyl)-N-(7-methoxy-4-(piperidin-1-yl) quinazolin-6-yl)pyrrolidine-2-carboxamide;

25) (S)—N-(4-(3-chloro-2,4-difluorophenylamino)-7-methoxyquinazolin-6-yl)-1-((S)-3,3-dimethyl-2-((S)-2-(methylamino)propanamido)butanoyl)azetidine-2-carboxamide;

26) (S)—N-(4-(3-chloro-2,4-difluorophenylamino)-7-methoxyquinazolin-6-yl)-1-((S)-3,3-dimethyl-2-((S)-2-(methylamino)propanamido)butanoyl)piperidin-3-carboxamide;

27) (S)—N-(4-(o-toluidino)-7-methoxyquinazolin-6-yl)-1-((S)-3,3-dimethyl-2-((S)-2-(methylamino)propanamido) butanoyl)pyrrolidine-2-carboxamide;

28) (S)—N-(4-(2,4-difluorophenylamino)-7-methoxyquinazolin-6-yl)-1-((S)-3,3-dimethyl-2-((S)-2-(methylamino)propanamido)butanoyl)pyrrolidine-2-carboxamide;

29) (S)—N-(4-(4-chloro-2-fluorophenylamino)-7-methoxyquinazolin-6-yl)-1-((S)-3,3-dimethyl-2-((S)-2-(methylamino)propanamido)butanoyl)pyrrolidine-2-carboxamide;
30) (S)—N-(4-(2-methoxyphenylamino)-7-methoxyquinazolin-6-yl)-1-((S)-3,3-dimethyl-2-((S)-2-(methylamino)propanamido)butanoyl)pyrrolidine-2-carboxamide;
31) (S)-1-((S)-3,3-dimethyl-2-((S)-2-(methylamino)propanamido)butanoyl)-N-(7-methoxy-4-(methyl(phenyl)amino)quinazolin-6-yl)pyrrolidine-2-carboxamide;
32) (S)-1-((S)-3,3-dimethyl-2-((S)-2-(methylamino)propanamido)butanoyl)-N-(7-methoxy-4-(naphthalen-2-ylamino)quinazolin-6-yl)pyrrolidine-2-carboxamide;
33) (S)-1-((S)-3,3-dimethyl-2-((S)-2-(methylamino)propanamido)butanoyl)-N-(7-methoxy-4-(pyridin-2-ylamino)quinazolin-6-yl)pyrrolidine-2-carboxamide;
34) (S)-1-((S)-3,3-dimethyl-2-((S)-2-(methylamino)propanamido)butanoyl)-N-(7-methoxy-4-((S)-1-phenylethylamino)quinazolin-6-yl)pyrrolidine-2-carboxamide;
35) (S)—N-(4-(2,4-difluorobenzylamino)-7-methoxyquinazolin-6-yl)-1-((S)-3,3-dimethyl-2-((S)-2-(methylamino)propanamido)butanoyl)pyrrolidine-2-carboxamide;
36) (S)—N-(4-amino-7-methoxyquinazolin-6-yl)-1-((S)-3,3-dimethyl-2-((S)-2-(methylamino)propanamido)butanoyl)pyrrolidine-2-carboxamide;
37) (S)—N-(4-(3-chloro-4-(3-fluorobenzyloxy)phenylamino)-7-methoxyquinazolin-6-yl)-1-((S)-3,3-dimethyl-2-((S)-2-(methylamino)propanamido)butanoyl)pyrrolidine-2-carboxamide;
38) (S)—N-(4-(cyclohexylamino)-7-methoxyquinazolin-6-yl)-1-((S)-3,3-dimethyl-2-((S)-2-(methylamino)propanamido)butanoyl)pyrrolidine-2-carboxamide;
39) (S)—N-(4-(biphenyl-4-ylamino)-7-methoxyquinazolin-6-yl)-1-((S)-3,3-dimethyl-2-((S)-2-(methylamino)propanamido)butanoyl)pyrrolidine-2-carboxamide;
40) (S)-1-((S)-3,3-dimethyl-2-((S)-2-(methylamino)propanamido)butanoyl)-N-(7-methoxy-4-(4-phenoxyphenylamino)quinazolin-6-yl)pyrrolidine-2-carboxamide;
41) (S)—N-(4-(3-chloro-4-fluorophenylamino)-7-methoxyquinazolin-6-yl)-1-((S)-3,3-dimethyl-2-((S)-2-(methylamino)propanamido)butanoyl)pyrrolidine-2-carboxamide;
42) (S)—N-(4-(2,3-difluorophenylamino)-7-methoxyquinazolin-6-yl)-1-((S)-3,3-dimethyl-2-((S)-2-(methylamino)propanamido)butanoyl)pyrrolidine-2-carboxamide;
43) (S)—N-(4-(3-chloro-2,4-difluorophenylamino)-7-hydroxyquinazolin-6-yl)-1-((S)-3,3-dimethyl-2-((S)-2-(methylamino)propanamido)butanoyl)pyrrolidine-2-carboxamide;
44) (S)—N—((S)-1-((S)-2-(4-((4-bromo-2-fluorophenylamino)-6-methoxyquinazolinyl-7-oxy)methyl)piperidine)-1-carbonyl)-1-pyrrolidinyl)-3,3-dimethyloxobutan-2-yl)-2-(methylamino)propanamide;
45) (S)—N-(4-(3-chloro-2,4-difluorophenylamino)-7-methoxyquinazolin-6-yl)-1-((2S,3R)-2-((S)-2-(methylamino)propanamido)-3-(prop-2-ynyloxy)butanoyl)pyrrolidine-2-carboxamide;
46) (2S,4R)-4-(benzyloxy)-N-(4-(3-chloro-2,4-difluorophenylamino)-7-methoxyquinazolin-6-yl)-1-((S)-3,3-dimethyl-2-((S)-2-(methylamino)propanamido)butanoyl)pyrrolidine-2-carboxamide;
47) (S)-1-((S)-3,3-dimethyl-2-((S)-2-(methylamino)propanamido)butanoyl)-N-(7-methoxy-4-(2-morpholinophenylamino)quinazolin-6-yl)pyrrolidine-2-carboxamide;
48) (S)—N-(4-(3-chloro-2,4-difluorophenylamino)quinazolin-6-yl)-1-((S)-3,3-dimethyl-2-((S)-2-(methylamino)propanamido)butanoyl)pyrrolidine-2-carboxamide;
49) (S)-1-((S)-3,3-dimethyl-2-((S)-2-(methylamino)propanoyl)-N-(7-methoxy-4-(4-methoxyphenylamino)quinazolin-6-yl)pyrrolidine-2-carboxamide;
50) (S)—N-(4-(3,4-dihydroquinoline-1(2H)-yl)-7-methoxyquinazolin-6-yl)-1-((S)-3,3-dimethyl-2-((S)-2-(methylamino)propanamido)butanoyl)pyrrolidine-2-carboxamide;
51) (S)—N-(4-(5-chlorobenzo[d][1,3]dioxol-4-ylamino)-7-methoxyquinazolin-6-yl)-1-((S)-3,3-dimethyl-2-((S)-2-(methylamino)propanamido)butanoyl)pyrrolidine-2-carboxamide;
52) (S)—N-(4-(2,3-dihydro-1H-inden-5-ylamino)-7-methoxyquinazolin-6-yl)-1-((S)-3,3-dimethyl-2-((S)-2-(methylamino)propanamido)butanoyl)pyrrolidine-2-carboxamide;
53) (S)-1-((S)-3,3-dimethyl-2-((S)-2-(methylamino)propanamido)butanoyl)-N-(7-methoxy-4-(quinoline-6-ylamino)quinazolin-6-yl)pyrrolidine-2-carboxamide;
54) (S)—N-(4-(1H-indazol-5-ylamino)-7-methoxyquinazolin-6-yl)-1-((S)-3,3-dimethyl-2-((S)-2-(methylamino)propanamido)butanoyl)pyrrolidine-2-carboxamide;
55) (S)-1-((S)-3,3-dimethyl-2-((S)-2-(methylamino)propanamido)butanoyl)-N-(4-(4-fluorophenylamino)-7-methoxyquinazolin-6-yl)pyrrolidine-2-carboxamide;
56) (S)—N-(4-(4-chlorophenylamino)-7-methoxyquinazolin-6-yl)-1-((S)-3,3-dimethyl-2-((S)-2-(methylamino)propanamido)butanoyl)pyrrolidine-2-carboxamide;
57) (S)-1-((S)-3,3-dimethyl-2-((S)-2-(methylamino)propanamido)butanoyl)-N-(7-methoxy-4-(3-methoxyphenylamino)quinazolin-6-yl)pyrrolidine-2-carboxamide;
58) (S)—N-(4-(2,4-dichlorophenylamino)-7-methoxyquinazolin-6-yl)-1-((S)-3,3-dimethyl-2-((S)-2-(methylamino)propanamido)butanoyl)pyrrolidine-2-carboxamide;
59) (S)—N-(4-(2,6-difluorophenylamino)-7-methoxyquinazolin-6-yl)-1-((S)-3,3-dimethyl-2-((S)-2-(methylamino)propanamido)butanoyl)pyrrolidine-2-carboxamide;
60) (S)-1-((S)-3,3-dimethyl-2-((S)-2-(methylamino)propanamido)butanoyl)-N-(4-(4-(4-ethylpiperazin-1-yl)phenylamino)-7-methoxyquinazolin-6-yl)pyrrolidine-2-carboxamide;
61) (S)—N-(4-(benzo[d][1,3]dioxol-5-ylamino)-7-methoxyquinazolin-6-yl)-1-((S)-3,3-dimethyl-2-((S)-2-(methylamino)propanamido)butanoyl)pyrrolidine-2-carboxamide;
62) (S)-1-((S)-3,3-dimethyl-2-((S)-2-(methylamino)propanamido)butanoyl)-N-(7-methoxy-4-(quinoline-3-ylamino)quinazolin-6-yl)pyrrolidine-2-carboxamide;
63) (S)-1-((S)-3,3-dimethyl-2-((S)-2-(methylamino)propanamido)butanoyl)-N-(7-methoxy-4-(quinoline-5-ylamino)quinazolin-6-yl)pyrrolidine-2-carboxamide;
64) (S)-1-((S)-3,3-dimethyl-2-((S)-2-(methylamino)propanamido)butanoyl)-N-(7-methoxy-4-(4-dimethylamino)phenylamino)quinazolin-6-yl)pyrrolidine-2-carboxamide;
65) (S)-1-((S)-3,3-dimethyl-2-((S)-2-(methylamino)propanamido)butanoyl)-N-(7-methoxy-4-(4-(pyrrolidin-1-yl)phenylamino)quinazolin-6-yl)pyrrolidine-2-carboxamide;
66) (S)-1-((S)-3,3-dimethyl-2-((S)-2-(methylamino)propanamido)butanoyl)-N-(7-methoxy-4-(4-(piperidin-1-yl)phenylamino)quinazolin-6-yl)pyrrolidine-2-carboxamide;

67) (S)-1-((S)-3,3-dimethyl-2-((S)-2-(methylamino)propanamido)butanoyl)-N-(7-methoxy-4-(4-(4-methylpiperazin-1-yl)phenylamino)quinazolin-6-yl)pyrrolidine-2-carboxamide;
68) (S)-1-((S)-3,3-dimethyl-2-((S)-2-(methylamino)propanamido)butanoyl)-N-(7-methoxy-4-(4-diethylamino)phenylamino)quinazolin-6-yl)pyrrolidine-2-carboxamide;
69) (S)—N-(4-(4-acetamidophenylamino)-7-methoxyquinazolin-6-yl)-1-((S)-3,3-dimethyl-2-((S)-2-(methylamino)propanamido)butanoyl)pyrrolidine-2-carboxamide;
70) (S)-1-((S)-3,3-dimethyl-2-((S)-2-(methylamino)propanamido)butanoyl)-N-(4-(4-(4-ethylpiperazin-1-yl)-3-(trifluoromethyl)phenylamino)-7-methoxyquinazolin-6-yl)pyrrolidine-2-carboxamide;
71) (S)-1-((S)-3,3-dimethyl-2-((S)-2-(methylamino)propanamido)butanoyl)-N-(4-(4-(4-ethylpiperazin-1-yl)-3-fluorophenylamino)-7-methoxyquinazolin-6-yl)pyrrolidine-2-carboxamide;
72) (S)—N-(4-((1,1-dioxide-4-thiomorpholinyl)phenylamino)-7-methoxyquinazolin-6-yl)-1-((S)-3,3-dimethyl-2-((S)-2-(methylamino)propanamido)butanoyl)pyrrolidine-2-carboxamide;
73) (S)-1-((S)-3,3-dimethyl-2-((S)-2-(methylamino)propanamido)butanoyl)-N-(7-methoxy-4-(pyridin-4-ylamino)quinazolin-6-yl)pyrrolidine-2-carboxamide;
74) (S)-1-((S)-3,3-dimethyl-2-((S)-2-(methylamino)propanamido)butanoyl)-N-(7-methoxy-4-(4-(methylcarbamoyl)phenylamino)quinazolin-6-yl)pyrrolidine-2-carboxamide;
75) (S)—N-(4-(5-acetamino-2-chlorophenylamino)-7-methoxyquinazolin-6-yl)-1-((S)-3,3-dimethyl-2-((S)-2-(methylamino)propanamido)butanoyl)pyrrolidine-2-carboxamide;
76) (S)—N-(4-(4-benzamidophenylamino)-7-methoxyquinazolin-6-yl)-1-((S)-3,3-dimethyl-2-((S)-2-(methylamino)propanamido)butanoyl)pyrrolidine-2-carboxamide;
77) (S)—N-(4-(cyclohexylmethyl)amino)-7-methoxyquinazolin-6-yl)-1-((S)-3,3-dimethyl-2-((S)-2-(methylamino)propanamido)butanoyl)pyrrolidine-2-carboxamide;
78) (S)—N-(4-((2-chloropyridin-3-yl)amino)-7-methoxyquinazolin-6-yl)-1-((S)-3,3-dimethyl-2-((S)-2-(methylamino)propanamido)butanoyl)pyrrolidine-2-carboxamide;
79) (S)—N-(4-((6-chloropyridin-3-yl)amino)-7-methoxyquinazolin-6-yl)-1-((S)-3,3-dimethyl-2-((S)-2-(methylamino)propanamido)butanoyl)pyrrolidine-2-carboxamide;
80) (S)—N-(4-((4-bromo-2-chlorophenyl)amino)-7-methoxyquinazolin-6-yl)-1-((S)-3,3-dimethyl-2-((S)-2-(methylamino)propanamido)butanoyl)pyrrolidine-2-carboxamide;
81) (S)—N-(4-((2,3-dichlorophenyl)amino)-7-methoxyquinazolin-6-yl)-1-((S)-3,3-dimethyl-2-((S)-2-(methylamino)propanamido)butanoyl)pyrrolidine-2-carboxamide;
82) (S)—N-(4-((2-bromo-4-fluorophenyl)amino)-7-methoxyquinazolin-6-yl)-1-((S)-3,3-dimethyl-2-((S)-2-(methylamino)propanamido)butanoyl)pyrrolidine-2-carboxamide;
83) (S)-1-((S)-3,3-dimethyl-2-((S)-2-(methylamino)propanamido)butanoyl)-N-(7-methoxy-4-(phenylamino)quinazolin-6-yl)pyrrolidine-2-carboxamide;
84) (S)-1-((S)-3,3-dimethyl-2-((S)-2-(methylamino)propanamido)butanoyl)-N-(7-methoxy-4-((6-(prop-2-yn-1-yloxy)pyridin-3-yl)amino)quinazolin-6-yl)pyrrolidine-2-carboxamide;
85) (S)-1-((S)-3,3-dimethyl-2-((S)-2-(methylamino)propanamido)butanoyl)-N-(4-((3-fluoro-4-(piperidin-1-yl)phenyl)amino)-7-methoxyquinazolin-6-yl)pyrrolidine-2-carboxamide;
86) (S)—N-(4-((3-chloro-4-(4-methylpiperazin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;
87) (S)—N-(4-((4-bromo-3-chloro-2-fluorophenyl)amino)-7-methoxyquinazolin-6-yl)-1-((S)-3,3-dimethyl-2-((S)-2-(methylamino)propanamido)butanoyl)pyrrolidine-2-carboxamide;
88) (S)—N-(4-((4-(1H-imidazol-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;
89) (S)-1-((S)-3,3-dimethyl-2-((S)-2-(methylamino)propanamido)butanoyl)-N-(4-(3-(2-fluorophenyl)ureido)-7-methoxyquinazolin-6-yl)pyrrolidine-2-carboxamide;
90) (S)-1-((S)-3,3-dimethyl-((S)-2-(methylamino)propanamido)butanoyl)-N-(7-methoxy-4-((4-morpholinophenyl)amino)quinazolin-6-yl)pyrrolidine-2-carboxamide;
91) (S)-1-((S)-3,3-dimethyl-2-((S)-2-(methylamino)propanamide)butanoyl)-N-(7-methoxy-4-((4-(2-propyn-1-yloxy)phenyl)amino)quinazolin-6-yl)pyrrolidine-2-carboxamide;
92) (S)—N-(4-((3-chloro-4-(4-(cyclopropylmethyl)piperazin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;
93) (S)-1-((S)-3,3-dimethyl-2-((S)-2-(methylamino)propanamide)butanoyl)-N-(7-methoxy-4-((2-methyl-4-oxo-4H-chromen-7-yl)amino)quinazolin-6-yl)pyrrolidine-2-carboxamide;
94) (S)-1-((S)-3,3-dimethyl-2-((S)-2-(methylamino)propanamide)butanoyl)-N-(7-methoxy-4-((2-oxoindolin-5-yl)amino)quinazolin-6-yl)pyrrolidine-2-carboxamide;
95) (S)—N-(4-((3-chloro-4-morpholinophenyl)amino)-7-methoxyquinazolin-6-yl)-1-((S)-3,3-dimethyl-2-((S)-2-(methylamino)propanamido)butanoyl)pyrrolidine-2-carboxamide;
96) (S)—N-(4-((3-chloro-4-(piperidin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;
97) (S)—N-(4-((3-chloro-4-(4-isopropylpiperazin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;
98) (S)—N-(4-((3-chloro-4-(4-propyl-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;
99) (S)—N-(4-((3-chloro-4-(diethylamino)phenyl)amino)-7-methoxyquinazolin-6-yl)-1-((S)-3,3-dimethyl-2-((S)-2-(methylamino)propanamido)butanoyl)pyrrolidine-2-carboxamide;
100) (S)—N-(4-((4-(4-(cyclopropylmethyl)piperazin-1-yl)-3-fluorophenyl)amino)-7-methoxyquinazolin-6-yl)-1-((S)-3,3-dimethyl-2-((S)-2-(methylamino)propanamido)butanoyl)pyrrolizine-2-carboxamide;

101) (S)—N-(4-((3,5-dichloro-4-(pyridin-2-ylmethoxy)phenyl)amino)-7-methoxyquinazolin-6-yl)-1-((S)-3,3-dimethyl-2-((S)-2-(methylamino)propanamido)butanoyl)pyrrolidine-2-carboxamide;
102) (S)—N-(4-((3-chloro-4-(pyridin-2-ylmethoxy)phenyl)amino)-7-methoxyquinazolin-6-yl)-1-((S)-3,3-dimethyl-2-((S)-2-(methylamino)propanamido)butanoyl)pyrrolidine-2-carboxamide;
103) (S)—N-(4-((4-([1,4'-bipiperidine]-1'-yl)phenyl)amino)-7-methoxyquinazolin-6-yl)-1-((S)-3,3-dimethyl-2-((S)-2-(methylamino)propanamido)butanoyl)pyrrolidine-2-carboxamide;
104) (S)-1-((S)-3,3-dimethyl-2-((S)-2-(methylamino)propanamido)butanoyl)-N-(7-methoxy-4-((4-(piperidin-1-ylmethyl)phenyl)amino)quinazolin-6-yl)pyrrolidine-2-carboxamide;
105) (S)-1-((S)-3,3-dimethyl-2-((S)-2-(methylamino)propanamido)butanoyl)-N-(7-methoxy-4-((4-(4-(4-methylpiperazin-1-yl)piperidin-1-yl)phenyl)amino)quinazolin-6-yl)pyrrolidine-2-carboxamide;
106) (S)-1-((S)-3,3-dimethyl-2-((S)-2-(methylamino)propanamido)butanoyl)-N-(7-methoxy-4-((4-(1-methylpiperidin-4-yl)phenyl)amino)quinazolin-6-yl)pyrrolidine-2-carboxamide;
107) (S)-1-((S)-3,3-dimethyl-2-((S)-2-(methylamino)propanamido)butanoyl)-N-(7-methoxy-4-((4-(4-methylpiperidin-1-yl)cyclohexyl)amino)quinazolin-6-yl)pyrrolidine-2-carboxamide;
108) (S)-1-((S)-3,3-dimethyl-2-((S)-2-(methylamino)propanamido)butanoyl)-N-(7-methoxy-4-((4-((4-methylpiperazin-1-yl)sulfonyl)phenyl)amino)quinazolin-6-yl)pyrrolidine-2-carboxamide;
109) (2S)-1-((S)-3,3-dimethyl-2-((S)-2-(methylamino)propanamido)butanoyl)-N-(7-methoxy-4-((4-(1-methylpiperidin-3-yl)phenyl)amino)quinazolin-6-yl)pyrrolidine-2-carboxamide;
110) (S)-1-((S)-3,3-dimethyl-2-((S)-2-(methylamino)propanamido)butanoyl)-N-(7-methoxy-4-((4-(4-(1-methylpiperidin-4-yl)piperazin-1-yl)phenyl)amino)quinazolin-6-yl)pyrrolizine-2-carboxamide;
111) (S)—N-(4-((4-((1H-imidazol-1-yl)methyl)phenyl)amino)-7-methoxyquinazolin-6-yl)-1-((S)-3,3-dimethyl-2-((S)-2-(methylamino)propanamido)butanoyl)pyrrolidine-2-carboxamide;
112) (S)-1-((S)-3,3-dimethyl-2-((S)-2-(methylamino)propanamido)butanoyl)-N-(4-((3-fluoro-4-(4-methylpiperazin-1-yl)phenyl)amino)-7-methoxyquinazolin-6-yl)pyrrolidine-2-carboxamide; and
113) (S)—N-(4-((3-chloro-4-(pyrrolidin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide.

The synthesis of the peptide analogs of the library of the present invention may be carried out using the general reaction scheme for preparing a library of Smac/DIABLO structure mimetics as shown in Reaction Scheme 1, and mass analysis may be performed using MicroMass ZQ™ (Waters).

The pharmaceutical composition comprising, as an active ingredient, the derivatives, salts, isomers, hydrates, or solvates prepared by such methods may be used for the prevention and treatment of cancer, inflammation, autoimmune diseases and neurodegenerative disorders caused by overexpression of IAPs.

The pharmaceutical composition of the present invention may be formulated in accordance with conventional methods, and may be prepared in the form of oral formulations such as tablets, pills, powders, capsules, syrups, emulsions, microemulsions, and others, or parental formulations such as intramuscular, intravenous, or subcutaneous administration.

For oral formulations, carriers such as cellulose, calcium silicate, corn starch, lactose, sucrose, dextrose, calcium phosphate, stearic acid, magnesium stearate, calcium stearate, gelatin, talc, surfactants, suspending agents, emulfiers, diluents, and others. For injectable formulations, carriers such as water, saline, glucose solution, glucose solution analogs, alcohols, glycols, ethers (e.g., polyethylene glycol 400), oils, fatty acids, fatty acid esters, glycerides, surfactants, suspending agents, emulsifiers, and others may be used.

Furthermore, the present invention provides a method for preventing or treating a cancer, inflammation, an autoimmune disease or a neurodegenerative disorder in a subject, which comprises administrating the compound of the present invention to the subject in need thereof.

A proposed daily dose of the inventive compound for administration to a human (of approximately 70 kg body weight) may be in the range of 1 mg/day to 2,000 mg/day. The inventive compound may be administered in a single dose or in divided doses per day. It is understood that the daily dose should be determined in light of various relevant factors including the condition, age, body weight and sex of the subject to be treated, administration route, and disease severity; and, therefore, the dosage suggested above should not be construed to limit the scope of the present invention in anyway.

Following abbreviations are used in preparation methods and Examples below:

Boc-: tert-butoxycarbonyl

Cbz-: 2-benzyloxycarbonylamino

DIPEA: N,N-diisopropylethylamine

DMAP: N,N-dimethylaminopyridine

DMF: N,N-dimethyl formamide

DMSO: dimethyl sulfoxide

EA: ethyl acetate

EDCI: 1-ethyl-3-(3-dimethylaminopropyl)carbodiimide hydrochloride

Fmoc-: 9-fluorenyloxycarbonyl

HATU: [2-(1H-9-azabenzotriazol-1-yl)-1,1,3,3-tetramethyluronium hexafluorophosphate]

Hex.: hexane

HOBT: N-hydroxybenzotriazole

Mass: mass chromatogram

MC: methylene chloride

MeOH: methanol

—OBn: —O-benzyl

THF: tetrahydrofuran

TLC: thin layer chromatography

Tle: t-butylglycine

Chg: cyclohexylglycine

Ala: alanine

MeAla: methylalanine

The compound of formula (I) of the present invention may be prepared by a solid-phase synthetic method as shown in Reaction Scheme 1.

[Reaction Scheme 1]

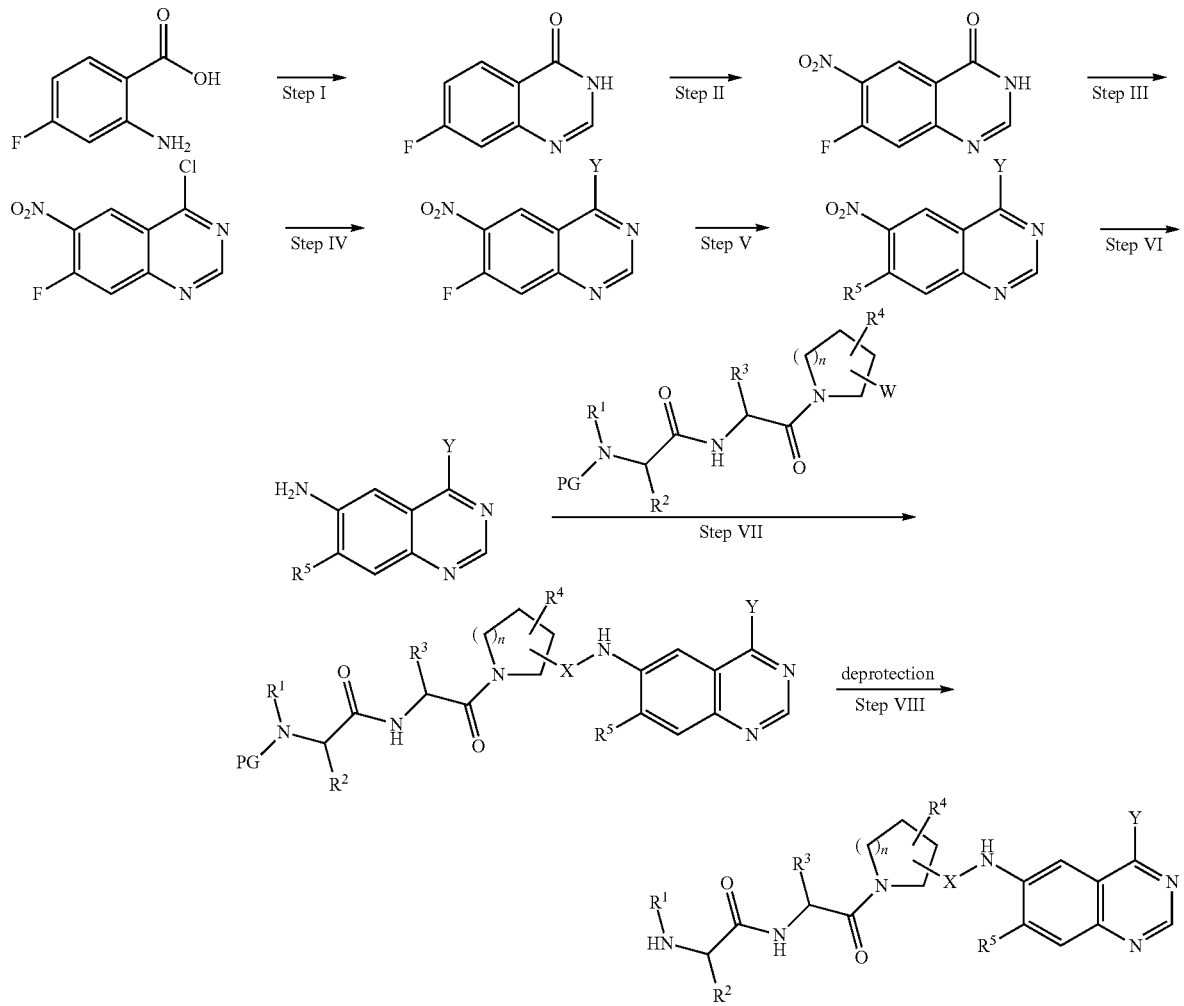

wherein:

X, Y, $R^1$ to $R^5$, and n have the same meanings as defined in formula (I), and PG represents a protection group and W represents —COOH or —CHO.

In Reaction Scheme 1, depending upon the residue of Y group, the sequence of steps IV and V may be changed. The reaction processes are exemplified in following stepwise reaction.

Step (I)

To a mixture of 2-amino-4-fluorobenzoic acid (1 equivalent) and formamide (5~6 equivalents), a catalytic amount (1/160~1/140 of formamide volume) of N,N-dimethylformamide is added and stirred. The mixture is heated to a temperature of 170~190° C., and further stirred for 12-14 hours. After the mixture is cooled to room temperature, distilled water (7~8 times the volume of formamide) is added. The resulting mixture is stirred for 20~40 min and filtered to obtain the desired compound as a solid.

Step (II)

The compound (1 equivalent) obtained in step (I) is gradually added to a mixed solution of sulfuric acid (0.3~0.4 mL/mmol) and nitric acid (0.3~0.4 mL/mmol) at −10~0° C. for 10~20 min. The solution is stirred for 1~2 hours at room temperature and heated to a temperature of 100~120° C., followed by further stirring for 2~3 hours. The solution is cooled to room temperature, and ice water (10 mmol/9~12 mL) is added. The resulting mixture is stirred for 20~30 min and filtered to obtain the desired compound as a solid.

Step (III)

To the compound (1 equivalent) obtained in step (II), thionyl chloride (2.0~2.5 mL/g) and phosphorus oxychloride (1.4~1.6 mL/g) and N,N-dimethylformamide (1 mL) are added. The solution is heated to 90~110° C. When the compound is completely resolved, the solution is stirred for 2~3 hours. The solution is cooled to room temperature and solvents are distilled under reduced pressure. The resulting residue is mixed with toluene (14~16 mL/g), and distilled again under reduced pressure. The procedure is repeated three times to obtain the desired compound.

Step (IV)

The compound (1 equivalent) obtained in step (III) and amine (1.1~1.3 equivalents) are dissolved in 2-propanol (20~22 mL/g). The mixture is heated to 70~90° C. and further stirred for 4~5 hours. The mixture is then cooled to room temperature, diluted with acetone (20~25 mL/g), and stirred for 10~20 min. The resulting mixture is filtered to obtain the desired compound as a solid.

Step (V)

The compound (6.3 g, 17.18 mmol)) obtained in step (IV) and NaY$^a$ (Y$^a$=R$^5$; 2.5~3.0 equivalents) are dissolved in DMSO (1.8~2.2 mL/g). To the mixture, KOTMS (potassium trimethylsilanolate; 3.5~4.5 equivalents) is added for 10~20 min. The mixed solution is stirred for 4~5 hours and completion of the reaction is confirmed using TLC. Then, water (15~20 mL/g) is added at −10~0° C. and the solution is stirred for 30~40 min. The resulting mixture is filtered, rinsed with water, and dried to obtain the desired compound as a solid.

Step (VI)

Iron (0.9~1.1 mg/g) is diluted in an aqueous solution of 5% acetic acid (5~6 mL/g) and activated by heating the solution to 90~110° C. The compound (1 equivalent) obtained in step (V) is dissolved in methylene chloride (3~4 mL/g) and acetic acid (1~1.5 mL/g), and the mixture is added to the activated iron, followed by reflux at 90~110° C. for 2~3 hours. After completion of the reaction, the mixed solution is filtered through a Celite pad, rinsed with a mixture of chloroform and isopropylalcohol (4:1 (v/v), 80~90 mL/g), and the resulting filtrate is rinsed with an aqueous solution of sodium bicarbonate. The organic layer is dried over sodium sulfate, filtered and dried under reduced pressure to obtain the desired compound.

Step (VII)

The compound (1 equivalent) obtained in step (VI) and Ala-Tle-Pro derivative (1.0~1.2 equivalents) and EDCI (1.2~1.4 equivalents) are dissolved in a solvent of pyridine (29~31 mL/g). The mixture is heated to 55~65° C., further stirred for 4~5 hours, distilled under reduced pressure, and purified by column chromatography to obtain the desired compound.

Step (VIII)

The compound (1 equivalent) obtained in step (VII) is dissolved in 4M HCl/dioxane (9~10 mL/g), and stirred for 1~2 hours at room temperature. The mixture is concentrated under reduced pressure, and recrystallized with diethyl ether to obtain the desired compound.

The following Examples are intended to further illustrate the present invention without limiting its scope.

Preparation Example 1

Preparation of (S)-1-((S)-2-((S)-2-(tert-butoxycarbonyl(methyl)amino)propanamido)-3,3-dimethylbutanoyl)pyrrolidine-2-carboxylic acid <Step 1> Preparation of (S)-2-benzyl 1-tert-butyl pyrrolidine-1,2-dicarboxylate Boc-Pro-OH (50.0 g, 0.23 mol) was dissolved in dichloromethane (500 mL), and EDCI (89.1 g, 0.46 mol), DMAP (5.7 g, 0.05 mol), DIPEA (162 mL, 0.93 mol) and benzyl alcohol (48 mL, 0.46 mol) were added dropwise. The mixture was stirred at room temperature for 12 hours. The mixture was washed several times with an aqueous solution of 5% citric acid. The organic layer was dried over sodium sulfate, and filtered and distilled under reduced pressure to obtain the title compound as yellow oil (70.0 g, 99%).

$^1$H NMR (300 MHz, CDCl$_3$): δ 7.32 (m, 5H), 5.20 (m, 2H), 4.27 (d, 1H), 3.52 (m, 2H), 1.91 (m, 4H), 1.35 (s, 9H)

MS (ESI$^+$, m/z): 306 [M+H]$^+$

<Step 2> Preparation of (S)-benzyl pyrrolidine-2-carboxylate hydrochloride

The compound (70.0 g, 0.23 mol) obtained in <Step 1> was dissolved in a solution of 4M HCl/dioxane (175 mL), and the mixture was stirred at room temperature for 1 hour. After completion of the reaction, the mixture was concentrated under reduced pressure, and recrystallized with diethyl ether to obtain the title compound as a white solid (42.6 g, 77%).

$^1$H NMR (300 MHz, CDCl$_3$): δ 7.32 (m, 5H), 5.20 (m, 2H), 4.27 (d, 1H), 3.52 (m, 2H), 1.91 (m, 4H)

MS (ESI$^+$, m/z): 206 [M+H]$^+$

<Step 3> Preparation of (S)-benzyl 1-((S)-2-(tert-butoxycarbonylamino)-3,3-dimethylbutanoyl)pyrrolidine-2-carboxylate The compound (30.0 g, 0.12 mol) obtained in <Step 2> was dissolved in dichloromethane (300 mL), and Boc-Tle-OH (26.7 g, 0.12 mol), HATU (56.6 g, 0.15 mol) and DIPEA (43 mL, 0.25 mol) were added dropwise. The mixture was stirred at room temperature for 4 hours. The mixture was filtered to remove insoluble components, and washed several times with a solution of 5% citric acid. The organic layer was dried over sodium sulfate, filtered and distilled under reduced pressure, and purified by column chromatography (mobile phase MC/methanol) to obtain the title compound as transparent oil (47.0 g, 91%).

$^1$H NMR (300 MHz, CDCl$_3$): δ 7.33 (m, 5H), 5.15 (m, 2H), 4.61 (m, 2H), 3.84 (m, 2H), 2.25 (m, 2H), 1.98 (m, 2H), 1.43 (s, 9H), 0.98 (s, 9H)

MS (ESI$^+$, m/z): 419 [M+H]$^+$

<Step 4> Preparation of (S)-benzyl 1-((S)-2-amino-3,3-dimethylbutanoyl)pyrrolidine-2-carboxylate hydrochloride The compound (47.0 g, 0.11 mol) obtained in <Step 3> was dissolved in a solution of 4M HCl/dioxane (115 mL) and the mixture was stirred at room temperature for 1 hour. After completion of the reaction, the mixture was concentrated under reduced pressure to obtain the title compound as transparent oil (39.0 g, 98%).

$^1$H NMR (300 MHz, CDCl$_3$): δ 7.35 (s, 5H), 5.18 (q, 2H), 4.67 (t, 1H), 4.02 (m, 2H), 3.56 (m, 1H), 2.32 (m, 1H), 1.93 (m, 3H), 1.13 (s, 9H)

MS (ESI$^+$, m/z): 319 [M+H]$^+$

<Step 5> Preparation of (S)-benzyl 1-((S)-2-((S)-2-(tert-butoxycarbonyl(methyl)amino)propanamido)-3,3-dimethylbutanoyl)pyrrolidine-2-carboxylate The compound (29.0 g, 0.08 mol) obtained in <Step 4> was dissolved in dichloromethane (300 mL), and Boc-MeAla-OH (24.9 g, 0.12 mol), EDCI (23.5 g, 0.12 mol) and DIPEA (43 mL, 0.25 mol) were added dropwise. The mixture was stirred at room temperature for 12 hours, and washed several times with an aqueous solution of 5% citric acid. The organic layer was dried over sodium sulfate, filtered and distilled under reduced pressure, and purified by column chromatography to obtain the title compound as transparent oil (30.0 g, 72%).

$^1$H NMR (300 MHz, CDCl$_3$): δ 7.33 (m, 5H), 5.16 (q, 2H), 4.16 (m, 1H), 4.54 (m, 1H), 3.84 (m, 1H), 3.66 (m, 1H), 2.77 (s, 3H), 2.18 (m, 1H), 1.95 (m, 3H), 1.47 (s, 9H), 1.29 (m, 5H), 0.96 (s, 9H)

MS (ESI$^+$, m/z): 504 [M+H]$^+$

<Step 6> Preparation of (S)-1-((S)-2-((S)-2-(tert-butoxycarbonyl(methyl)amino)propanamido)-3,3-dimethylbutanoyl)pyrrolidine-2-carboxylic acid The compound (28.0 g, 0.06 mol) obtained in <Step 5> was dissolved in methanol (300 mL), and 10% Pd/C (2.8 g) was added thereto, followed by stirring for 1.5 hours under hydrogenation conditions. Insoluble components were removed by filtration, and the filtrate was concentrated under reduced pressure, followed by purification using a column chromatography to obtain the title compound as a white solid (21.0 g, 91%).

$^1$H NMR (300 MHz, CDCl$_3$): δ 4.57 (m, 3H), 3.83 (m, 1H), 3.65 (m, 1H), 2.75 (s, 3H), 2.31 (m, 1H), 2.01 (m, 3H), 1.46 (s, 9H), 1.29 (d, 3H), 0.98 (s, 9H)

MS (ESI$^+$, m/z): 414 [M+H]$^+$

Preparation Example 2

Preparation of (S)-2-((S)-2-(tert-butoxycarbonyl(methyl)amino)propanamido)-3,3-dimethylbutanoic acid <Step 1> Preparation of (S)-benzyl 2-(tert-butoxycarbonylamino)-3,3-dimethylbutanoic acid Boc-Tle-OH (4.8 g, 22.3 mmol) was dissolved in dichloromethane (50 mL), and EDCI (4.3 g, 44.6 mmol), DMAP (0.6 g, 4.46 mmol), DIPEA (16 mL, 89.2 mmol), and benzyl alcohol (5 mL, 44.6 mmol) were added dropwise. The mixture was stirred at room temperature for 12 hours. The mixture was washed several times with an aqueous solution of 5% citric acid. The organic layer was dried over sodium sulfate, and filtered and distilled under reduced pressure to obtain the title compound as yellow oil (6.7 g, 99%).

MS (ESI$^+$, m/z): 322 [M+H]$^+$

<Step 2> Preparation of (S)-benzyl 2-amino-3,3-dimethylbutanoate hydrochloride

The compound (6.7 g, 22.3 mmol) obtained in <Step 1> was dissolved in a solution of 4M HCl/dioxane (17 mL) and the mixture was stirred at room temperature for 1 hour. The mixture was concentrated under reduced pressure to obtain the title compound as yellow oil (5.0 g, 93%).

MS (ESI$^+$, m/z): 222 [M+H]$^+$

<Step 3> Preparation of (S)-benzyl 2-((S)-2-(tert-butoxycarbonyl(methyl)amino)propanamido)-3,3-dimethylbutanoate (S)-benzyl 2-amino-3,3-dimethylbutanoate hydrochloride (30.0 g, 0.12 mol) obtained in <Step 2> was dissolved in dichloromethane (300 mL), and Boc-Tle-OH (26.7 g, 0.12 mol), HATU (56.6 g, 0.15 mol) and DIPEA (43 mL, 0.25 mol) were added dropwise. The mixture was stirred at room temperature for 4 hours. Insoluble components were removed by filtration, and the filtrate was washed several times with an aqueous solution of 5% citric acid. The organic layer was dried over sodium sulfate, filtered and distilled under reduced pressure, and purified by column chromatography to obtain the title compound as transparent oil (47.0 g, 91%).

MS (ESI$^+$, m/z): 407 [M+H]$^+$

<Step 4> Preparation of (S)-2-((S)-2-(tert-butoxycarbonyl(methyl)amino)propanamido)-3,3-dimethylbutanoic acid The compound (5.5 g, 14.1 mmol) obtained in <Step 3> was dissolved in methanol (50 mL), and 10% Pd/C (0.6 g) was added thereto, followed by stirring for 2 hours under hydrogenation conditions. Insoluble components were removed by filtration, and the filtrate was concentrated under reduced pressure, followed by purification using a column chromatography to obtain the title compound as a white solid (3.0 g, 71%).

MS (ESI$^+$, m/z): 317 [M+H]$^+$

Example 1

Preparation of (S)—N-(4-(3-chloro-2,4-difluorophenylamino)-7-methoxyquinazolin-6-yl)-1-((S)-3,3-dimethyl-2-((S)-2-(methylamino)propanamido)butanoyl)pyrrolidine-2-carboxamide hydrochloride <Step 1> Preparation of 7-fluoro-3H-quinazolin-4-one 2-amino-4-fluorobenzoic acid (100 g, 0.64 mol) and formamide (154 mL, 3.87 mol) were mixed with a catalytic amount (1 mL) of N,N-dimethylformamide. The mixture was heated to 180° C. and further stirred for 14 hours. The mixture was cooled to room temperature, and distilled water (1000 mL) was added thereto. The mixture was stirred for 30 min and filtered to obtain the title compound (86 g, 81.3%).

$^1$H NMR (300 MHz, CDCl$_3$): δ 12.34 (s, 1H), 8.19-8.12 (m, 2H), 7.46-7.34 (m, 2H)

MS (ESI$^+$, m/z): 165 [M+H]$^+$

<Step 2> Preparation of 7-fluoro-6-nitro-3H-quinazolin-4-one

The compound (25 g, 152 mmol) obtained in <Step 1> was added dropwise to a solution of sulfuric acid (50 mL) and nitric acid (51 mL) at 0° C. The mixture was stirred at room temperature for 1 hour, and heated to 110° C., followed by stirring for 2 hours. The mixture was cooled to room temperature and ice water (300 mL) was added thereto. The resulting mixture was stirred for about 30 min and filtered to obtain the title compound as a solid (25 g, 79%).

$^1$H NMR (300 MHz, CDCl$_3$): δ 12.83 (bs, 1H), 8.72 (d, 1H), 8.32 (s, 1H), 7.79 (d, 1H)

MS (ESI$^+$, m/z): 210 [M+H]$^+$

<Step 3> Preparation of 4-chloro-7-fluoro-6-nitro-quinazoline

The compound (20 g, 96 mmol) obtained in <Step 2> was mixed with thionyl chloride (170 mL), phosphorus oxychloride (30 mL) and N,N-dimethylformamide (1 mL) by stirring. The mixture was heated to 100° C. in order to melt the compounds completely, and stirred for 2 hours. The mixture was cooled to room temperature and distilled under reduced pressure. The residue thus obtained was mixed with toluene (300 mL) and the mixture was again distilled under reduced pressure. The procedure was repeated three times to obtain the title compound (21 g, 99%).

$^1$H NMR (300 MHz, CDCl$_3$): δ 8.72 (d, 1H), 8.30 (s, 1H), 7.73 (d, 1H)

MS (ESI$^+$, m/z): 227 [M+H]$^+$

<Step 4> Preparation of (3-chloro-2,4-difluoro-phenyl)-(7-fluoro-6-nitro-quinazolin-4-yl)-amine 4-chloro-7-fluoro-6-nitro-quinazoline (5 g, 22.0 mmol) obtained in <Step 3> and 3-chloro-2,4-difluoro-aniline (5.39 g, 33.0 mmol) were dissolved in 2-propanol (109 mL). The mixture was heated to 80° C. and further stirred for 4 hours. The mixture was cooled to room temperature, diluted with acetone (100 mL), and stirred for 10 min. The resulting mixture was filtered to the title compound as a solid (7.21 g, 92%).

$^1$H NMR (300 MHz, CDCl$_3$): δ 9.62 (s, 1H), 8.47 (s, 1H), 7.95 (d, 1H), 7.53 (s, 1H), 7.46 (s, 1H)

MS (ESI$^+$, m/z): 355 [M+H]$^+$

<Step 5> Preparation of (3-chloro-2,4-difluoro-phenyl)-(7-methoxy-6-nitro-quinazolin-4-yl)-amine The compound (6.3 g, 17.18 mmol) obtained in <Step 4> and NaOMe (2.78 g, 51.54 mmol) was dissolved in 10 mL of DMSO. Then, KOTMS (8.82 g, 68.72 mmol) was added thereto for 10 min. The mixture was stirred for 4 hours. After confirming completion of the reaction using TLC, water (200 mL) was added thereto at 0° C., followed by stirring for 30 min. The resulting mixture was filtered, washed with water, and dried to obtain the title compound as a solid (3.5 g, 56%).

$^1$H NMR (300 MHz, CDCl$_3$): δ 9.62 (s, 1H), 8.47 (s, 1H), 7.95 (d, 1H), 7.53 (s, 1H), 7.46 (s, 1H), 4.06 (s, 3H)

MS (ESI$^+$, m/z): 367 [M+H]$^+$

<Step 6> Preparation of N4-(3-chloro-2,4-difluoro-phenyl)-7-methoxy-quinazolin-4,6-diamine Iron (100 mg) was diluted with an aqueous solution of 5% acetic acid (5 mL) and activated by heating to 100° C. The compound (1 g, 2.73 mmol) obtained in <Step 5> was dissolved in 3 mL of methylene chloride and 1 mL of acetic acid, mixed with the activated iron, and the mixture was refluxed at 100° C. for 2 hours. After completion of the reaction, the mixture was filtered through a Celite pad under reduced pressure, washed with a solution of chloroform:isopropylalcohol=4:1 (v/v) (80 mL), and the resulting filtrate was washed with an aqueous solution of sodium bicarbonate. The organic layer was dried over sodium sulfate, and filtered and distilled under reduced pressure to obtain the title compound (551 mg, 60%).

$^1$H NMR (300 MHz, CDCl$_3$): δ 10.40 (s, 1H), 9.16 (s, 1H), 8.50 (s, 1H), 7.71 (m, 2H), 7.52 (m, 1H), 5.42 (s, 2H), 4.05 (s, 3H)

MS (ESI$^+$, m/z): 337 [M+H]$^+$

<Step 7> Preparation of tert-butyl(S)-1-((S)-1-((S)-2-(4-(3-chloro-2,4-difluorophenylamino)-7-methoxyquinazolin-6-ylcarbamoyl)pyrrolidin-1-yl)-3,3-dimethyl-1-oxobutan-2-ylamino)-1-oxopropan-2-yl(methyl)carbamate The compound (1 g, 2.97 mmol) obtained in <Step 6>, AVP derivatives (1.23 g, 2.97 mmol) obtained in pyridine (29.7 mL). The mixture was heated to 60° C., further stirred for 4 hours, distilled under reduced pressure, and purified by column chromatography to obtain the title compound (1.21 g, 56%).

MS (ESI$^+$, m/z): 731 [M+H]$^+$

<Step 8> Preparation of (S)—N-(4-(3-chloro-2,4-difluorophenylamino)-7-methoxyquinazolin-6-yl)-1-((S)-3,3-dimethyl-2-((S)-2-(methylamino)propanamido)butanoyl)pyrrolidine-2-carboxamide hydrochloride The compound (88 mg, 0.12 mmol) obtained in <Step 7> was dissolved in a solution of 4M HCl/dioxane (1 mL), and the mixture was stirred at room temperature for 1 hour. After completion of the reaction, the mixture was concentrated under reduced pressure and recrystallized with diethyl ether to obtain the title compound as white oil (75 mg, 94%).

$^1$H NMR (300 MHz, CDCl$_3$): δ 11.34 (s, 1H), 9.86 (s, 1H), 9.32 (s, 1H), 9.21 (s, 1H), 8.89 (m, 2H), 8.57 (d, 1H), 7.57 (m, 1H), 7.43 (m, 2H), 4.80 (m, 1H), 4.06 (d, 1H), 4.11 (s, 3H), 3.92 (m, 7H), 1.31 (d, 3H), 0.98 (s, 9H)

MS (ESI$^+$, m/z): 632 [M+H]$^+$

Example 2

Preparation of (S)—N-(4-(3-chloro-2-fluorophenylamino)-7-(2-methoxyethoxy)quinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2-fluoro-4-chloro-aniline instead of 3-chloro-2,4-difluoro-aniline in <Step 4> and using 2-methoxyethanol instead of NaOMe in <Step 5> to obtain the title compound (300 mg, 9%).

$^1$H NMR (300 MHz, DMSO-d6): δ 9.76 (s, 1H), 9.32 (m, 1H), 8.89 (s, 1H), 8.78 (m, 2H), 8.60 (d, 1H), 7.63 (t, 1H), 7.52 (m, 2H), 7.35 (m, 1H), 4.80 (m, 1H), 4.43 (m, 1H), 4.41 (m, 2H), 3.99 (m, 2H), 3.88 (s, 3H), 3.80 (m, 4H), 1.99 (m, 6H), 1.35 (d, 3H), 1.01 (s, 9H)

MS (ESI$^+$, m/z): 658 [M+H]$^+$

Example 3

Preparation of ((S)—N-(4-(5-chlorobenzo[d][1,3]dioxol-4-ylamino)-7-(2-methoxyethoxy)quinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 5-chloro[d][1,3]dioxol-4-amine instead of 3-chloro-2,4-difluoro-aniline in <Step 4> to obtain the title compound (38 mg, 75%).

$^1$H NMR (300 MHz, DMSO-d6): δ 11.56 (brs, 1H), 9.64 (brs, 1H), 9.09 (s, 1H), 8.92 (brs, 1H), 8.85 (s, 1H), 8.65 (d, 1H), 7.60 (s, 1H), 7.12-7.01 (m, 2H), 6.12 (s, 2H), 4.81-4.80 (m, 1H), 4.51-4.39 (m, 3H), 3.99-3.81 (m, 5H), 3.35 (s, 3H), 2.43 (s, 3H), 2.02-1.89 (m, 4H), 1.33 (s, 3H), 0.99 (s, 9H).

MS (ESI$^+$, m/z): 721 [M+H]$^+$

Example 4

Preparation of (S)—N-(4-(3-chloro-2-fluorophenylamino)quinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2-amino benzoic acid instead of 2-amino-4-fluorobenzoic acid in <Step 1>, using 2-fluoro-3-chloro-aniline instead of 3-chloro-2,4-difluoro-aniline in <Step 4>, and omitting <Step 5> to obtain the title compound (35 mg, 7%).

MS (ESI$^+$, m/z): 584 [M+H]$^+$

Example 5

Preparation of (S)—N-(4-(3-chloro-4-fluorophenylamino)-7-(2-methoxyethoxy)quinazolin-6-yl)-1-((S)-3,3-dimethyl-2-((S)-2-(methylamino)propanamido)butanoyl)pyrrolidine-2-carboxamide hydrochloride The procedure of Example 2 was repeated except for using 3-chloro-4-fluoro-aniline instead of 3-chloro-2,4-difluoro-aniline in <Step 4> to obtain the title compound (57 mg, 8%).

$^1$H NMR (300 MHz, DMSO-d6): δ 11.2 (s, 1H), 9.87 (s, 1H), 9.47 (s, 1H), 9.11 (s, 1H), 8.91 (m, 2H), 8.69 (m, 1H), 7.96 (m, 1H), 7.78 (s, 1H), 7.51 (m, 2H), 4.91 (m, 1H), 4.81 (m, 1H), 4.51 (m, 1H), 4.38 (m, 3H), 3.37 (m, 1H), 3.51 (m, 10H), 2.01 (m, 5H), 1.35 (s, 3H), 1.03 (s, 9H)

MS (ESI$^+$, m/z): 658 [M+H]$^+$

Example 6

Preparation of (S)—N-(4-(3-chloro-2,4-difluorophenylamino)-7-(2-methoxyethoxy)quinazolin-6-yl)-1-((S)-3,3-dimethyl-2-((S)-2-(methylamino) propanamido)butanoyl)pyrrolidine-2-carboxamide hydrochloride The procedure of Example 2 was repeated except for using 2,4-difluoro-3-chloro-aniline instead of 3-chloro-2,4-difluoro-aniline in <Step 4> to obtain the title compound (52 mg, 8%).

$^1$H NMR (300 MHz, DMSO-d6): δ 9.78 (s, 2H), 9.19 (s, 1H), 8.99 (s, 1H), 8.81 (s, 1H), 8.63 (d, 1H), 7.60 (m, 2H), 7.47 (m, 1H), 4.80 (m, 1H), 4.51 (d, 1H), 3.99 (s, 1H), 3.86 (m, 2H), 3.77 (m, 1H), 3.47 (m, 1H), 3.37 (s, 3H), 2.44 (s, 3H), 2.04 (s, 1H), 2.01 (m, 2H), 1.93 (m, 2H), 1.37 (d, 3H), 0.99 (s, 9H)

MS (ESI$^+$, m/z): 676 [M+H]$^+$

Example 7

Preparation of (S)—N-(4-(3-chloro-2-fluorophenylamino)-7-(2-methoxyethoxy)quinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2-fluoro-3-chloro-aniline instead of 3-chloro-2,4-difluoro-aniline in <Step 4> to obtain the title compound (172 mg, 9%).

¹H NMR (300 MHz, DMSO-d6): δ 9.98 (s, 1H), 9.25 (s, 1H), 8.94 (s, 1H), 8.79 (s, 1H), 8.72 (s, 1H), 8.69 (s, 1H), 7.71 (m, 2H), 7.59 (m, 4H), 7.42 (m, 3H), 4.84 (m, 1H), 4.64 (d, 1H), 4.13 (m, 9H), 3.79 (m, 15H), 2.18 (s, 1H), 2.12 (m, 1H), 2.08 (m, 5H), 1.44 (d, 3H), 1.24 (s, 9H)
MS (ESI⁺, m/z): 614 [M+H]⁺

Example 8

Preparation of (S)—N-(4-(3,4-dichloro-2-fluorophenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 3,4-dichloro-2-fluoro-aniline instead of 3-chloro-2,4-difluoro-aniline in <Step 4> to obtain the title compound (32 mg, 55%).
¹H NMR (300 MHz, MeOD): δ 9.89 (s, 1H), 9.55 (br, 1H), 9.14 (s, 1H), 8.92 (br, 1H), 8.62 (d, 1H), 7.66 (d, 1H), 7.59-7.54 (m, 2H), 4.84-4.80 (m, 1H), 4.52 (d, 1H), 4.08 (s, 3H), 3.98-3.97 (m, 1H), 3.81-3.67 (m, 2H), 2.80 (s, 3H), 2.44 (d, 3H), 2.03-1.93 (m, 4H), 1.35 (d, 3H), 1.01 (s, 9H)
MS (ESI⁺, m/z): 647, 649 [M+H]⁺

Example 9

Preparation of (S)—N-(4-(4-bromo-2-fluorophenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2-fluoro-4-bromoaniline instead of 2,4-difluoro-aniline in <Step 4> to obtain the title compound (290 mg, 89%).
¹H NMR (300 MHz, DMSO-d6): δ 11.44 (brs, 1H), 9.89 (s, 1H), 9.60 (brs, 1H), 9.14 (s, 1H), 9.33 (brs, 1H), 9.83 (s, 1H), 8.62 (d, 1H), 7.78 (d, 1H), 7.61 (s, 1H), 4.83-4.82 (m, 1H), 4.52 (d, 1H), 4.13 (s, 3H), 4.07-4.01 (m, 1H), 3.80-3.56 (m, 2H), 2.46 (s, 3H), 2.04-1.99 (m, 4H), 1.35 (d, 3H), 1.01 (s, 9H)
MS (ESI⁺, m/z): 696, 698 [M+H]⁺

Example 10

Preparation of (S)-1-((S)-3,3-dimethyl-2-((S)-2-(methylamino)propanamido)butanoyl)-N-(4-(2-fluorophenylamino)-7-methoxyquinazolin-6-yl)pyrrolidine-2-carboxamide hydrochloride The procedure of Example 1 was repeated except for using 2-fluoroaniline instead of 3-chloro-2,4-difluoro-aniline in <Step 4> to obtain the title compound (32 mg, 55%).
¹H NMR (300 MHz, MeOD): δ 9.19 (s, 1H), 8.66 (s, 1H), 7.54 (m, 1H), 7.44 (m, 1H), 7.29 (m, 2H), 4.68 (s, 1H), 4.17 (s, 3H), 3.97 (m, 2H), 3.80 (m, 1H), 2.67 (s, 3H), 2.17 (m, 4H), 1.49 (s, 3H), 1.11 (s, 9H)
MS (ESI⁺, m/z): 580 [M+H]⁺

Example 11

Preparation of (S)—N-(4-phenylamino-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using aniline instead of 2,4-difluoro-aniline in <Step 4> to obtain the title compound (250 mg, 93%).

¹H NMR (300 MHz, DMSO-d6): δ 11.41 (brs, 1H), 9.79 (brs, 1H), 8.97 (brs, 1H), 8.62 (s, 1H), 7.70 (d, 2H), 7.41 (t, 2H), 7.29-7.14 (m, 3H), 7.00-6.90 (brs, 1H), 4.91-4.88 (m, 1H), 4.80-4.66 (m, 1H), 4.65 (d, 1H), 3.99-3.88 (m, 4H), 3.74-3.72 (m, 1H), 2.80 (s, 3H), 2.55-2.50 (m, 2H), 2.20-2.05 (m, 2H), 1.34 (d, 3H), 0.99 (s, 9H)
MS (ESI⁺, m/z): 599 [M+H]⁺

Example 12

Preparation of (S)-1-((S)-2-((S)-2-aminopropanamido)-3,3-dimethylbutanoyl)-N-(4-(3-chloro-2,4-difluorophenylamino)-7-methoxyquinazolin-6-yl)pyrrolidine-2-carboxamide hydrochloride The procedure of Example 1 was repeated except for using Boc-Ala-OH instead of Boc-MeAla-OH in <Step 5> of Preparation Example 1 to obtain the title compound (100 mg, 5%).
¹H NMR (300 MHz, DMSO-d6): δ 10.87 (s, 2H), 9.82 (s, 1H), 9.06 (s, 1H), 8.68 (s, 1H), 8.45 (m, 4H), 7.56 (s, 2H), 7.43 (s, 1H), 4.78 (s, 2H), 4.43 (d, 2H), 4.17 (s, 6H), 3.93 (s, 2H), 3.77 (d, 8H), 3.01 (m, 13H), 2.00 (m, 7H), 1.30 (d, 3H), 0.99 (s, 9H)
MS (ESI⁺, m/z): 618 [M+H]⁺

Example 13

Preparation of (S)-1-((S)-2-((S)-2-acrylamidopropanamido)-3,3-dimethylbutanoyl)-N-(4-(3-chloro-2,4-difluorophenylamino)-7-methoxyquinazolin-6-yl)pyrrolidine-2-carboxamide hydrochloride The compound (30 mg, 0.046 mmol) obtained in Example 12 and NaHCO₃ (11.6 mg, 0.14 mmol) were dissolved in THF (0.8 mL): H₂O (0.2 mL), and acryloyl chloride (0.004 mL, 0.046 mmol) was added thereto at 0° C. The mixture was stirred at 0° C. for 30 min, and an aqueous solution of NaHCO₃ was added thereto, followed by washing several times with chloroform. The organic layer was dried over sodium sulfate, filtered and distilled under reduced pressure, and purified by column chromatography to obtain the title compound (15 mg, 8%).
¹H NMR (300 MHz, MeOD): δ 9.92 (s, 1H), 9.21 (s, 1H), 9.15 (s, 1H), 8.61 (s, 1H), 7.92 (s, 1H), 7.72 (m, 1H), 7.26 (m, 1H), 7.04 (m, 1H), 6.31 (m, 2H), 6.12 (m, 1H), 5.71 (d, 1H), 4.90 (m, 3H), 4.62 (m, 1H), 4.35 (d, 1H), 3.89 (s, 3H), 3.79 (m, 6H), 3.71 (m, 6H), 2.02 (m, 4H), 1.99 (m, 7H), 1.50 (m, 4H), 1.36 (d, 3H), 1.25 (s, 9H), 1.02 (m, 17H)
MS (ESI⁺, m/z): 672 [M+H]⁺

Example 14

Preparation of (S)—N-(4-(3-chloro-2,4-difluorophenylamino)-7-((S)-tetrahydrofuran-3-yloxy)quinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using (S)-tetrahydrofuran-3-ol instead of NaOMe in <Step 5> to obtain the title compound (402 mg, 52%).
¹H NMR (300 MHz, DMSO-d6): δ 9.87 (s, 1H), 9.55 (s, 1H), 8.86 (s, 1H), 8.39 (s, 1H), 8.01 (d, 1H), 4.36 (t, 1H), 4.01 (m, 3H), 3.83 (m, 3H), 3.46 (m, 2H), 3.19 (m, 1H), 2.25 (s, 3H), 2.12 (m, 4H), 1.17 (d, 3H), 0.97 (s, 9H)
MS (ESI⁺, m/z): 687, 689 [M+H]⁺

Example 15

Preparation of (S)—N-(4-(3-chloro-2,4-difluorophenylamino)-7-methoxyquinazolin-6-yl)-1-((S)-2-cyclohexyl-2-((S)-2-(methylamino)propanamido)acetyl)pyrrolidine-2-carboxamide hydrochloride The procedure of Example 1 was repeated except for using Boc-Chg-OH instead of Boc-Tle-OH in <Step 3> of Preparation Example 1 to obtain the title compound (71 mg, 8%).
$^1$H NMR (300 MHz, MeOD): δ 9.18 (s, 1H), 8.72 (s, 1H), 8.60 (d, 1H), 7.71 (m, 1H), 7.69 (m, 1H), 7.58 (m, 1H), 7.36 (s, 1H), 7.26 (m, 1H), 4.73 (s, 1H), 4.55 (m, 1H), 4.20 (m, 4H), 4.01 (m, 2H), 3.73 (m, 5H), 3.67 (m, 9H), 3.67 (m, 9H), 3.57 (m, 1H), 2.68 (s, 2H), 2.02 (m, 6H), 1.68 (m, 8H), 1.42 (d, 3H), 1.32 (m, 9H), 1.25 (m, 5H), 0.97 (m, 4H)
MS (ESI$^+$, m/z): 658 [M+H]$^+$

Example 16

Preparation of (S)—N-(4-(3-chloro-2,4-difluorophenylamino)-7-((R)-tetrahydrofuran-3-yloxy)quinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using (R)-tetrahydrofuran-3-ol instead of NaOMe in <Step 5> to obtain the title compound (41 mg, 84%).
$^1$H NMR (300 MHz, MeOD): δ 9.17 (s, 1H), 8.72 (s, 1H), 7.57 (m, 1H), 7.34 (m, 2H), 5.39 (s, 1H), 4.69 (s, 3H), 4.32 (d, 1H), 4.12 (m, 6H), 2.69 (s, 3H), 2.52 (m, 7H), 1.52 (d, 3H), 1.10 (s, 9H)
MS (ESI$^+$, m/z): 687, 689 [M+H]$^+$

Example 17

Preparation of (S)-1-((S)-3,3-dimethyl-2-((S)-2-(methylamino)propanamido)butanoyl)-N-(7-methoxy-4-(2,3,4-trifluorophenylamino)quinazolin-6-yl)pyrrolidine-2-carboxamide hydrochloride The procedure of Example 1 was repeated except for using 2,3,4-trifluoroaniline instead of 3-chloro-2,4-difluoro-aniline in <Step 4> to obtain the title compound (61 mg, 77%).
$^1$H NMR (300 MHz, MeOD): δ 9.20 (s, 1H), 8.71 (s, 1H), 7.36 (m, 3H), 4.69 (s, 1H), 4.18 (s, 3H), 3.99 (m, 3H), 2.67 (s, 3H), 2.18 (m, 4H), 1.50 (s, 3H), 1.11 (s, 9H)
MS (ESI$^+$, m/z): 616 [M+H]$^+$

Example 18

Preparation of (S)—N-(4-benzylamino-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for carrying a reaction at room temperature using benzylamine instead of 2,4-difluoro-aniline in <Step 4> to obtain the title compound (153 mg, 93%).
$^1$H NMR (300 MHz, DMSO-d6): δ 10.44 (brs, 1H), 9.81 (s, 1H), 9.53 (brs, 1H), 8.96 (s, 1H), 8.95-8.88 (brs, 1H), 8.83 (s, 1H), 8.61 (d, 1H), 7.45 (s, 1H), 7.40-7.28 (m, 5H), 4.91 (d, 2H), 4.81-4.77 (m, 1H), 4.52 (d, 1H), 4.10 (s, 3H), 4.06-3.96 (m, 1H), 3.80-3.71 (m, 2H), 2.46 (s, 3H), 2.14-1.91 (m, 3H), 1.35 (d, 3H), 1.00 (s, 9H).
MS (ESI$^+$, m/z): 613 [M+H]$^+$

Example 19

Preparation of (S)—N-(4-(3-chloro-4-(6-methylpyridin-3-yloxy)phenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 3-chloro-4-(6-methylpyridin-3-yloxy)phenylamine instead of 2,4-difluoro-aniline in <Step 4> to obtain the title compound (134 mg, 91%).
$^1$H NMR (300 MHz, DMSO-d6): δ 11.51 (brs, 1H), 9.90 (s, 1H), 9.65 (brs, 1H), 9.17 (s, 1H), 8.94 (brs, 1H), 8.93 (s, 1H), 8.63 (d, 1H), 8.51 (s, 1H), 8.02 (s, 1H), 7.88 (brs, 1H), 7.72-7.68 (m, 2H), 7.61 (s, 1H), 7.37 (d, 1H), 4.83-4.80 (m, 1H), 4.52 (d, 1H), 4.08 (s, 3H), 4.07-4.01 (m, 1H), 3.98-3.71 (m, 2H), 2.64 (s, 3H), 2.45 (s, 3H), 2.10-1.95 (m, 4H), 1.36 (d, 3H), 1.01 (s, 9H).
MS (ESI$^+$, m/z): 740, 742 [M+H]$^+$

Example 20

Preparation of (S)—N-(4-(3-chloro-2,4-difluorophenylamino)-7-methoxyquinazolin-6-yl)-1-((S)-3,3-dimethyl-2-((S)-2-(methylamino)propanamido)butanoyl)azetidine-2-carboxamide hydrochloride <Step 7> Preparation of (S)-tert-butyl 2-(4-(3-chloro-2,4-difluorophenylamino)-7-methoxyquinazolin-6-ylcarbamoyl)azetidine-1-carboxylate The compound (300 mg, 0.891 mmol) obtained in <Step 6> of Example 1, 1-Boc-L-azetidine-2-carboxylic acid (269 mg, 1.336 mmol) and HATU (677 mg, 1.782 mmol) were dissolved in N,N-dimethylformamide (4 mL). Then, DIPEA (0.63 mL, 3.564 mmol) was added thereto, and the mixture was stirred at 45° C. for 12 hours. The mixture was diluted with ethyl acetate and washed with an aqueous solution of sodium bicarbonate. The organic layer was dried over sodium sulfate, filtered and distilled under reduced pressure, and purified by column chromatography to obtain the title compound as a transparent solid (300 mg, 65%).
$^1$H NMR (300 MHz, CDCl$_3$): δ 9.11 (s, 1H), 8.65 (s, 1H), 8.20 (m, 1H), 7.43 (s, 1H), 7.27 (s, 1H), 7.04 (td, 1H), 4.86 (m, 1H), 4.04 (s, 3H), 3.99 (m, 1H), 3.89 (m, 1H), 2.80 (s, 1H), 2.59 (m, 2H), 1.51 (s, 9H)

<Step 8> Preparation of (S)—N-(4-(3-chloro-2,4-difluorophenylamino)-7-methoxyquinazolin-6-yl)azetidine-2-carboxamide The compound (300 mg, 0.577 mmol) obtained in <Step 7> was dissolved in methylene chloride (5 mL) and TFA (5 mL) was added thereto. The mixture was stirred at room temperature for 1 hour and concentrated under reduced pressure. The concentrate was diluted with ethyl acetate and washed with an aqueous solution of sodium bicarbonate. The organic layer was dried over sodium sulfate, filtered and distilled under reduced pressure, and purified by column chromatography to obtain the title compound as a white solid (125 mg, 63%).
$^1$H NMR (300 MHz, CDCl$_3$): δ 10.43 (s, 1H), 9.15 (s, 1H), 8.67 (s, 1H), 8.21 (m, 1H), 7.49 (s, 1H), 7.31 (s, 1H), 7.06 (td, 1H), 4.55 (m, 1H), 4.11 (s, 3H), 3.90 (m, 1H), 3.45 (m, 1H), 2.79 (m, 1H), 2.55 (m, 1H), 2.40 (s, 1H)

<Step 9> Preparation of tert-butyl(S)-1-((S)-1-((S)-2-(4-(3-chloro-2,4-difluorophenylamino)-7-methoxyquinazolin-6-ylcarbamoyl)azetidine-1-yl)-3,3-dimethyl-1-oxobutan-2-ylamino)-1-oxopropan-2-yl(methyl)carbamate The compound (152 mg, 0.362 mmol) obtained in <Step 8> and HATU (275 mg, 0.724 mmol) were dissolved in N,N-dimethylformamide (20 mL). Then, DIPEA (0.25 mL, 1.448 mmol) was added thereto and the mixture was stirred at 45° C. for 12 hours. The mixture was diluted with ethyl acetate and washed with an aqueous solution of sodium bicarbonate. The organic layer was dried over sodium sulfate, filtered and distilled under reduced pressure, and purified by column chromatography to obtain the title compound (80 mg, 31%).

MS (ESI$^+$, m/z): 718.29 [M+H]$^+$

<Step 10> Preparation of (S)—N-(4-(3-chloro-2,4-difluorophenylamino)-7-methoxyquinazolin-6-yl)-1-((S)-3,3-dimethyl-2-((S)-2-(methylamino)propanamido)butanoyl)azetidine-2-carboxamide hydrochloride The compound (80 mg, 0.11 mmol) obtained in <Step 9> was dissolved in a solution of 4M HCl/dioxane (1 mL) and the mixture was stirred at room temperature for 1 hour. After completion of the reaction, the mixture was concentrated under reduced pressure, and recrystallized with diethyl ether to obtain the title compound as a white solid (10 mg, 14%).

$^1$H NMR (300 MHz, DMSO-d6): δ 10.02 (s, 1H), 9.86 (s, 1H), 9.32 (s, 1H), 8.53 (s, 1H), 8.05 (d, 1H), 7.65 (m, 1H), 7.50 (m, 1H), 7.40 (s, 1H), 5.21 (s, 1H), 4.43 (m, 3H), 4.14 (s, 3H), 3.53 (m, 1H), 3.18 (m, 1H), 2.40 (s, 3H), 2.25 (m, 1H), 2.09 (m, 1H), 1.26 (d, 3H), 1.12 (s, 9H).

Example 21

Preparation of (S)—N-(4-(2-chlorophenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2-chloroaniline instead of 2,4-difluoro-aniline in <Step 4> to obtain the title compound (320 mg, 88%).

$^1$H NMR (300 MHz, DMSO-d6): δ 9.8 (m, 1H0, 9.4 (m, 1H), 9.15 (m, 1H), 8.8 (m, 1H), 8.7 (m, 1H), 8.5 (m, 1H), 7.63 (m, 1H), 7.45 (m, 5H), 4.8 (m, 1H), 4.5 (m, 1H), 4.0 (s, 3H), 3.9 (m, 1H), 3.7 (m, 2H), 2.3-1.9 (m, 5H), 1.33 (d, 3H), 1.00 (s, 9H).

MS (ESI$^+$, m/z): 633[M+H]$^+$

Example 22

Preparation of (S)—N-(4-(2-bromophenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2-chloroaniline instead of 2,4-difluoro-aniline in <Step 4> to obtain the title compound (200 mg, 93%).

$^1$H NMR (300 MHz, DMSO-d6): δ 11.7 (m, 1H), 9.8 (m, 1H), 9.4 (m, 1H), 9.3 (m, 1H), 8.9 (m, 1H), 8.7 (m, 1H), 8.6 (dd, 1H), 7.7 (dd, 1H), 7.4 (m, 3H), 7.3 (m, 1H), 4.8 (m, 1H), 4.5 (m, 1H), 4.0 (s, 3H), 3.9 (m, 1H), 3.7 (m, 3H), 2.4 (m, 2H), 2.0 (m, 4H), 1.3 (d, 2H), 1.1 (m, 2H), 1.01 (s, 9H).

MS (ESI$^+$, m/z): 678 [M+H]$^+$

Example 23

Preparation of (S)-1-((S)-3,3-dimethyl-2-((S)-2-(methylamino)propanamido)butanoyl)-N-(7-methoxy-4-(methylamino)quinazolin-6-yl)pyrrolidine-2-carboxamide <Step 5> Preparation of (7-fluoro-6-nitroquinazolin-4-yl)methylamine 4-chloro-7-fluoro-6-nitro-quinazoline (1 g, 4.39 mmol) obtained in <Step 4> of Example 1 and methylamine (dissolved in THF, 2.0 M, 11 mL, 22.0 mmol) were dissolved in 2-propanol (14 mL) and the mixture was stirred at room temperature for 1 hour. The mixture was diluted with chloroform (64 mL) and washed with an aqueous solution of sodium bicarbonate. The organic layer was dried over sodium sulfate, filtered and distilled under reduced pressure to obtain the title compound (623 mg, 64%).

$^1$H NMR (300 MHz, DMSO-d6): δ 9.23 (d, 1H), 9.03 (br.s, 1H), 8.57 (s, 1H), 7.67 (d, 1H), 3.01 (s, 3H)

MS (ESI$^+$, m/z): 223 [M+H]$^+$

<Step 6> Preparation of (7-methoxy-6-nitroquinazolin-4-yl)methylamine

The procedure of Example 1 was repeated except for using (7-fluoro-6-nitroquinazolin-4-yl)methylamine (623 mg, 8.41 mmol) instead of (3-chloro-2,4-difluoro-phenyl)-(7-fluoro-6-nitro-quinazolin-4-yl)amine in <Step 6> to obtain the title compound (313 mg, 48%).

$^1$H NMR (300 MHz, DMSO-d6): δ 8.89 (s, 1H), 8.65 (br.s, 1H), 8.50 (s, 1H), 7.33 (s, 1H), 4.00 (s, 3H), 2.98 (s, 3H)

MS (ESI$^+$, m/z): 235 [M+H]$^+$

<Step 7> Preparation of 7-methoxy-N4-methylquinazolin-4,6-diamine

The compound (313 mg, 1.34 mmol) obtained in <Step 6> was dissolved in 13 mL of ethanol, Pd/C (32 mg) was added thereto, and the mixture was stirred under hydrogen balloon at room temperature for 5 hours. The mixture was filtered through a Celite pad and distilled under reduced pressure to obtain the title compound (196 mg, 72%).

MS (ESI$^+$, m/z): 205 [M+H]$^+$

<Step 8> Preparation of tert-butyl(S)-1-((S)-1-((S)-2-(7-methoxy-4-(methylamino)quinazolin-6-ylcarbamoyl)pyrrolidin-1-yl)-3,3-dimethyl-1-oxobutan-2-ylamino)-1-oxopropan-2-yl(methyl)carbamate The AVP derivative 594 mg, 1.44 mmol) obtained in Preparation Example 1, HATU (1.09 g, 2.87 mmol) and DIEA (0.83 mL, 4.79 mmol) were dissolved in DMF (5.0 mL) by stirring at room temperature for 30 min. Then, the compound (196 mg, 0.958 mmol) obtained in <Step 7> was added thereto, and the mixture was stirred at 45° C. for 18 hours. The mixture was cooled to room temperature, distilled with 30 mL of ethyl acetate, and washed with an aqueous solution of sodium bicarbonate. The organic layer was washed three times with water, dried over sodium sulfate, and filtered and distilled under reduced pressure. The resulting oil was recrystallized with ethyl acetate and hexane to obtain the title compound (506 mg, 88%).

MS (ESI$^+$, m/z): 602 [M+H]$^+$

<Step 9> Preparation of (S)-1-((S)-3,3-dimethyl-2-((S)-2-(methylamino)propanamido)butanoyl)-N-(7-methoxy-4-(methylamino)quinazolin-6-yl)pyrrolidine-2-carboxamide The compound (506 mg, 0.12 mmol) obtained in <Step 8> was dissolved in dichloromethane (6 mL), and trifluoroacetic acid (6 mL) was added thereto, followed by stirring at room temperature for 1 hour. The mixture was washed with sodium bicarbonate, dried over sodium sulfate, and filtered and distilled under reduced pressure. The resultant was recrystallized with ethyl acetate and hexane to obtain the title compound (240 mg, 57%) as a white solid.

$^1$H NMR (300 MHz, DMSO-d6): δ 9.49 (s, 1H), 8.59 (s, 1H), 8.35 (s, 1H), 7.98 (br.d, 1H), 7.85 (d, 1H), 7.15 (s, 1H), 4.74 (m, 1H), 4.52 (d, 1H), 3.96 (s, 3H), 3.72 (m, 2H), 2.98 (m, 1H), 2.93 (d, 3H), 2.17 (s, 3H), 1.97 (m, 4H), 1.08 (d, 3H), 0.95 (s, 9H)

MS (ESI$^+$, m/z): 501 [M+H]$^+$

Example 24

Preparation of (S)-1-((S)-3,3-dimethyl-2-((S)-2-(methylamino)propanamido)butanoyl)-N-(7-methoxy-4-(piperidin-1-yl)quinazolin-6-yl)pyrrolidine-2-carboxamide hydrochloride The procedure of Example 1 was repeated except for using piperidine instead of 2,4-difluoro-aniline in <Step 4> to obtain the title compound (330 mg, 92%).

$^1$H NMR (300 MHz, DMSO-d6): δ 9.94 (s, 1H), 9.60 (brs, 1H), 8.95 (s, 1H), 8.94 (brs, 1H), 8.75 (s, 1H), 8.61 (d, 1H), 7.47 (s, 1H), 4.76-4.74 (m, 1H), 4.51 (d, 1H), 4.05 (s, 3H), 4.02-3.97 (m, 1H), 3.78-3.57 (m, 7H), 2.46 (s, 3H), 2.30-1.92 (m, 3H), 1.77 (brs, 6H), 1.34 (d, 3H), 1.03 (s, 9H).

MS (ESI$^+$, m/z): 591 [M+H]$^+$

Example 25

Preparation of (S)—N-(4-(3-chloro-2,4-difluorophenylamino)-7-methoxyquinazolin-6-yl)-1-((S)-3,3-dimethyl-2-((S)-2-(methylamino)propanamido)butanoyl)azetidine-2-carboxamide The procedure of Example 20 was repeated except for using (S)-(−)-N-Boc-carbonyl-2-piperidin-carboxylic acid instead of 1-Boc-L-azetidine-2-carboxylic acid in <Step 7> to obtain the title compound (3 mg, 5%).

$^1$H NMR (300 MHz, DMSO-d6): δ 9.84 (s, 1H), 9.20 (s, 1H), 8.84 (s, 1H), 8.38 (s, 1H), 7.91 (d, 1H), 7.51 (m, 1H), 7.35 (m, 1H), 7.28 (s, 1H), 5.43 (s, 1H), 4.89 (d, 1H), 4.14 (d, 1H), 3.98 (s, 3H), 2.97 (m, 1H), 2.13 (m, 5H), 1.97 (m, 1H), 1.62 (m, 4H), 1.41 (m, 1H), 1.22 (d, 3H), 0.95 (s, 9H)

Example 26

Preparation of (S)—N-(4-(3-chloro-2,4-difluorophenylamino)-7-methoxyquinazolin-6-yl)-1-((S)-3,3-dimethyl-2-((S)-2-(methylamino)propanamido)butanoyl)piperidin-3-carboxamide hydrochloride The procedure of Example 20 was repeated except for using (S)-(−)-N-Boc-carbonyl-3-piperidin-carboxylic acid instead of 1-Boc-L-azetidine-2-carboxylic acid in <Step 7> to obtain the title compound (3 mg, 2%).

$^1$H NMR (300 MHz, DMSO-d6): δ 8.84 (s, 1H), 8.48 (s, 1H), 7.71 (m, 1H), 7.18 (s, 1H), 7.00 (td, 1H), 4.81 (s, 1H), 4.64 (m, 1H), 4.13 (m, 1H), 4.01 (s, 3H), 3.33 (m, 1H), 3.04 (m, 2H), 2.90 (m, 1H), 2.37 (s, 3H), 2.10-1.80 (m, 4H), 1.26 (d, 3H), 0.94 (s, 9H)

Example 27

Preparation of (S)—N-(4-(o-toluidino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using o-toluidine instead of 2,4-difluoro-aniline in <Step 4> to obtain the title compound (70 mg, 54%).

$^1$H NMR (300 MHz, DMSO-d6): δ 11.4 (m, 1H), 9.8 (m, 1H), 9.48 (m, 1H), 9.1 (m, 1H), 8.9 (m, 1H), 8.8 (m, 1H), 8.7 (m, 1H), 7.52 (m, 1H), 7.36 (m, 1H), 7.3 (m, 3H), 4.8 (m, 1H), 4.5 (m, 1H), 4.00 (s, 3H), 3.99 (m, 2H), 3.40 (m, 2H), 2.4 (m, 3H), 2.15 (m, 3H), 1.96 (m, 4H), 1.13 (m, 3H), 1.17 (m, 2H), 0.99 (s, 9H).

MS (ESI$^+$, m/z): 613[M+H]$^+$

Example 28

Preparation of (S)—N-(4-(2,4-difluorophenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2,4-difluoro-aniline instead of 3-chloro-2,4-difluoro-aniline in <Step 4> to obtain the title compound (57 mg, 7%).

$^1$H NMR (300 MHz, DMSO-d6): δ 11.4 (s, 1H), 9.95 (s, 1H), 9.46 (m, 1H), 9.07 (s, 1H), 8.85 (s, 1H), 8.75 (s, 1H), 8.58 (d, 1H), 7.53 (m, 3H), 7.19 (t, 1H), 4.78 (m, 1H), 4.51 (d, 1H), 4.05 (s, 3H), 3.75 (m, 1H), 3.58 (m, 3H), 2.19 (m, 1H), 1.98 (m, 4H), 1.32 (d, 3H), 0.98 (s, 1H), 0.93 (s, 9H)

MS (ESI$^+$, m/z): 597 [M+H]$^+$

Example 29

Preparation of (S)—N-(4-(4-chloro-2-fluorophenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2-fluoro-4-chloro-aniline instead of 3-chloro-2,4-difluoro-aniline in <Step 4> to obtain the title compound (75 mg, 9%).

$^1$H NMR (300 MHz, DMSO-d6): δ 11.35 (s, 1H), 9.85 (s, 1H), 9.43 (m, 1H), 8.89 (s, 1H), 8.78 (s, 1H), 8.67 (s, 1H), 8.58 (d, 1H), 7.65 (d, 1H), 7.53 (m, 2H), 7.38 (m, 1H), 4.77 (m, 1H), 4.49 (d, 1H), 4.11 (s, 3H), 3.95 (s, 1H), 3.67 (m, 4H), 1.97 (m, 1H), 1.93 (m, 4H), 1.32 (d, 4H), 0.98 (s, 9H), 0.92 (s, 3H)

MS (ESI$^+$, m/z): 614 [M+H]$^+$

Example 30

Preparation of (S)—N-(4-(2-methoxyphenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for carrying a reaction at room temperature using 2-methoxyaniline instead of 3-chloro-2,4-difluoro-aniline in <Step 4> to obtain the title compound (100 mg, 48%).

$^1$H NMR (300 MHz, DMSO-d6): δ 11.4 (m, 1H), 9.85 (m, 1H), 9.6 (m, 1H), 9.1 (m, 1H), 8.9 (m, 1H), 8.7 (m, 1H), 8.6 (m, 1H), 7.48 (m, 1H), 7.38 (m, 2H), 7.10 (m, 1H), 7.0 (m,

1H), 4.8 (m, 1H), 4.5 (m, 1H), 4.0 (m, 3H), 3.9 (m, 1H), 3.7 (s, 3H), 3.68 (m, 1H), 2.4 (m, 3H), 2.0 (m, 4H), 1.34 (m, 3H), 0.95 (s, 9H).
MS (ESI$^+$, m/z): 629 [M+H]$^+$

Example 31

Preparation of (S)-1-((S)-3,3-dimethyl-2-((S)-2-(methylamino)propanamido)butanoyl)-N-(7-methoxy-4-(methyl(phenyl)amino)quinazolin-6-yl)pyrrolidine-2-carboxamide hydrochloride The procedure of Example 1 was repeated except for using N-methyl-aniline instead of 3-chloro-2,4-difluoro-aniline in <Step 4> to obtain the title compound (5 mg, 7%).
$^1$H NMR (300 MHz, DMSO-d6): 8.59 (s, 1H), 8.01 (s, 1H), 7.40 (m, 2H), 7.25 (t, 1H), 7.15 (m, 3H), 4.45 (s, 2H), 3.90 (s, 3H), 3.76 (m, 1H), 3.71 (m, 1H), 3.60 (s, 3H), 3.50 (s, 3H), 3.17 (m, 1H), 2.32 (s, 3H), 1.25 (d, 6H), 1.07 (s, 9H)
MS (ESI$^+$, m/z): 575 [M+H]$^+$ Example 32

Preparation of (S)-1-((S)-3,3-dimethyl-2-((S)-2-(methylamino)propanamido)butanoyl)-N-(7-methoxy-4-(naphthalen-2-ylamino)quinazolin-6-yl)pyrrolidine-2-carboxamide <Step 5> Preparation of (7-fluoro-6-nitroquinazolin-4-yl)naphthalen-2-ylamine
The procedure of Example 23 was repeated except for using 2-naphthylamine instead of methylamine in <Step 5> to obtain the title compound (66 mg, 23%).
$^1$H NMR (300 MHz, DMSO-d6): δ 10.7 (s, 1H), 9.68 (d, 1H), 8.75 (s, 1H), 8.38 (s, 1H), 7.87 (m, 5H), 7.50 (m, 2H)
MS (ESI$^+$, m/z): 335 [M+H]$^+$
<Step 6> Preparation of (7-methoxy-6-nitroquinazolin-4-yl)naphthalen-2-ylamine
The procedure of Example 23 was repeated except for using (7-fluoro-6-nitroquinazolin-4-yl)naphthalen-2-ylamine instead of (7-methoxy-6-nitroquinazolin-4-yl)methylamine in <Step 6> to obtain the title compound (42 mg, 61%).
$^1$H NMR (300 MHz, DMSO-d6): δ 10.3 (s, 1H), 9.34 (s, 1H), 8.69 (s, 1H), 8.41 (s, 1H), 7.94 (s, 2H), 7.88 (d, 2H), 7.49 (m, 3H), 4.07 (s, 3H)
MS (ESI$^+$, m/z): 347 [M+H]$^+$
<Step 7> Preparation of 7-methoxy-N4-naphthalen-2-yl-quinazolin-4,6-diamine
The procedure of Example 23 was repeated except for using the compound obtained in <Step 6> instead of 7-methoxy-6-nitroquinazolin-4-yl)methylamine in <Step 7> to obtain the title compound (37 mg, 99%).
MS (ESI$^+$, m/z): 317 [M+H]$^+$
<Step 8> Preparation of tert-butyl(S)-1-((S)-1-((S)-2-(7-methoxy-4-(naphthalen-2-ylamino)quinazolin-6-ylcarbamoyl)pyrrolidin-1-yl)-3,3-dimethyl-1-oxobutan-2-ylamino)-1-oxopropan-2-yl(methyl)carbamate
The procedure of Example 23 was repeated except for using the compound obtained in <Step 7> instead of 7-methoxy-N4-methylquinazolin-4,6-diamine in <Step 8> to obtain the title compound (17 mg, 20%).
MS (ESI$^+$, m/z): 712 [M+H]$^+$
<Step 9> Preparation of (S)-1-((S)-3,3-dimethyl-2-((S)-2-(methylamino)propanamido)butanoyl)-N-(7-methoxy-4-(naphthalen-2-ylamino)quinazolin-6-yl)pyrrolidine-2-carboxamide
The procedure of Example 23 was repeated except for using [1-(1-{2-[7-methoxy-4-(naphthalen-2-ylamino)quinazolin-6-ylcarbamoyl]pyrrolidine-1-carbonyl}-2,2-dimethylpropylcarbamoyl)ethyl]methylcarbamic acid tert-butylester instead of (1-{1-[2-(7-methoxy-4-methylaminoquinazolin-6-ylcarbamoyl)pyrrolidine-1-carbonyl]-2,2-dimethylpropylcarbamoyl}ethyl) methylcarbamic acid tert-butylester in <Step 9> to obtain the title compound (2.5 mg, 4%).
$^1$H NMR (300 MHz, DMSO-d6): δ 9.97 (s, 1H), 9.60 (s, 1H), 8.96 (s, 1H), 8.54 (m, 1H), 8.29 (s, 1H), 7.88 (m, 5H), 7.47 (m, 3H), 4.80 (m, 1H), 4.33 (d, 1H), 3.96 (s, 3H), 3.75 (m, 2H), 2.19 (s, 3H), 1.96 (m, 4H), 1.14 (d, 3H), 0.95 (s, 9H)
MS (ESI$^+$, m/z): 612 [M+H]$^+$ Example 33

Preparation of (S)-1-((S)-3,3-dimethyl-2-((S)-2-(methylamino)propanamido)butanoyl)-N-(7-methoxy-4-(pyridin-2-ylamino)quinazolin-6-yl)pyrrolidine-2-carboxamide <Step 7> Preparation of (7-methoxy-6-nitro-quinazolin-4-yl)pyridin-2-ylamine
7-methoxy-6-nitroquinazolin-4-ylamine (300 mg, 1.36 mmol) in <Step 6> of Example 23, 2-bromopyridine (0.2 mL, 2.04 mmol), palladium acetate (31 mg, 0.136 mmol), Xantphos (158 mg, 0.273 mmol) and cesium carbonate (888 mg, 2.73 mmol) were placed under 6.5 mL of 1,4-dioxane in a closed container, degassed, and the mixture was stirred at 120° C. for 2 hours. The mixture was cooled to room temperature, 50 mL water was added thereto, and the mixture was washed with a solution of chloroform/isopropanol (4:1). The mixture was dried over sodium sulfate and filtered and distilled under reduced pressure. The resulting oil was purified by column chromatography to obtain the title compound (78.5 mg, 20%).
$^1$H NMR (300 MHz, DMSO-d6): δ 10.7 (s, 1H), 9.46 (s, 1H), 8.73 (s, 1H), 8.42 (br.d, 1H), 8.36 (d, 1H), 7.87 (t, 1H), 7.49 (s, 1H)
MS (ESI$^+$, m/z): 298 [M+H]$^+$
<Step 8> Preparation of 7-methoxy-N4-pyridin-2-yl-quinazolin-4,6-diamine
The procedure of Example 23 was repeated except for using the compound obtained in <Step 7> instead of 7-methoxy-N4-methylquinazolin-4,6-diamine in <Step 8> to obtain the title compound (30 mg, 42%).
MS (ESI$^+$, m/z): 268 [M+H]$^+$
<Step 9> Preparation of tert-butyl(S)-1-((S)-1-((S)-2-(7-methoxy-4-(pyridin-2-ylamino)quinazolin-6-ylcarbamoyl) pyrrolidin-1-yl)-3,3-dimethyl-1-oxobutan-2-ylamino)-1-oxopropan-2-yl(methyl)carbamate
The procedure of Example 23 was repeated except for using the compound obtained in <Step 8> instead of 7-methoxy-N4-methylquinazolin-4,6-diamine in <Step 8> to obtain the title compound (35 mg, 47%).
MS (ESI$^+$, m/z): 664 [M+H]$^+$
<Step 10> Preparation of (S)-1-((S)-3,3-dimethyl-2-((S)-2-(methylamino)propanamido)butanoyl)-N-(7-methoxy-4-(pyridin-2-ylamino)quinazolin-6-yl)pyrrolidine-2-carboxamide
The procedure of Example 23 was repeated except for using [1-(1-{2-[7-methoxy-4-(pyridin-2-ylamino)-quinazolin-6-ylcarbamoyl]-pyrrolidine-1-carbonyl}-2,2-dimethylpropylcarbamoyl)ethyl]methylcarbamic acid tert-butylester instead of (1-{1-[2-(7-methoxy-4-methylaminoquinazolin-6-ylcarbamoyl)pyrrolidine-1-carbonyl]-2,2-dimethylpropylcarbamoyl}ethyl)methylcarbamic acid tert-butylester in <Step 9> to obtain the title compound (21 mg, 69%).

¹H NMR (300 MHz, DMSO-d6): δ 10.0 (br.s, 1H), 9.57 (s, 1H), 9.01 (s, 1H), 8.59 (s, 1H), 8.34 (m, 2H), 8.23 (d, 1H), 7.82 (t, 1H), 7.30 (m, 1H), 7.10 (m, 1H), 4.78 (m, 1H), 4.52 (d, 1H), 4.01 (s, 3H), 3.74 (m, 2H), 3.45 (m, 1H), 2.32 (s, 3H), 2.06 (m, 2H), 1.92 (m, 2H), 1.23 (d, 3H), 0.99 (s, 9H)
MS (ESI⁺, m/z): 564 [M+H]⁺

Example 34

Preparation of (S)-1-((S)-3,3-dimethyl-2-((S)-2-(methylamino)propanamido)butanoyl)-N-(7-methoxy-4-((S)-1-phenylmethylamino)quinazolin-6-yl)pyrrolidine-2-carboxamide hydrochloride The procedure of Example 1 was repeated except for carrying a reaction at room temperature using (S)-(−)-alpha-methylbenzyl amine instead of 3-chloro-2,4-difluoro-aniline in <Step 4> to obtain the title compound (40 mg, 41%).
¹H NMR (300 MHz, DMSO-d6): δ 10.12 (d, 1H), 9.77 (s, 1H), 9.35 (s, 1H), 8.98 (s, 1H), 8.91 (s, 1H), 8.81 (s, 1H), 8.60 (d, 1H), 7.47 (m, 2H), 7.37 (m, 3H), 7.30 (m, 1H), 5.83 (m, 1H), 4.77 (m, 1H), 4.52 (d, 1H), 4.03 (s, 3H), 3.97 (m, 1H), 3.78 (m, 1H), 3.69 (m, 2H), 3.56 (s, 3H), 2.14-1.94 (m, 4H), 1.65 (d, 3H), 1.34 (d, 3H), 1.00 (s, 9H)

Example 35

Preparation of (S)—N-(4-(2,4-difluorobenzylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for carrying a reaction at room temperature using 2,4-difluorobenzylamine instead of 3-chloro-2,4-difluoro-aniline in <Step 4> to obtain the title compound (50 mg, 47%).
¹H NMR (300 MHz, DMSO-d6): δ 10.30 (s, 1H), 9.78 (s, 1H), 9.40 (s, 1H), 8.94 (s, 1H), 8.85 (m, 1H), 8.80 (s, 1H), 8.59 (d, 1H), 7.42 (m, 1H), 7.40 (s, 1H), 7.26 (td, 1H), 7.04 (td, 1H), 4.89 (m, 2H), 4.78 (m, 1H), 4.50 (d, 1H), 4.05 (s, 3H), 4.00 (m, 2H), 3.89 (m, 1H), 3.73 (m, 1H), 2.46 (s, 3H), 2.13 (m, 1H), 1.90 (m, 3H), 1.33 (d, 3H), 0.99 (s, 9H)

Example 36

Preparation of (S)—N-(4-amino-7-methoxyquinazolin-6-yl)-1-((S)-3,3-dimethyl-2-((S)-2-(methylamino)propanamido)butanoyl)pyrrolidine-2-carboxamide <Step 5>: Preparation of 7-fluoro-6-nitroquinazolin-4-ylamine
The procedure of Example 23 was repeated except for using ammonia instead of methylamine in <Step 5> to obtain the title compound (7.5 g, 82%).
¹H NMR (300 MHz, DMSO-d6): δ 8.69 (s, 1H), 7.99 (d, 1H), 7.67 (br.s, 2H), 7.05 (s, 1H)
MS (ESI⁺, m/z): 209[M+H]⁺
<Step 6> Preparation of 7-methoxy-6-nitroquinazolin-4-ylamine
The procedure of Example 23 was repeated except for using 7-fluoro-6-nitroquinazolin-4-ylamine instead of (7-fluoro-6-nitroquinazolin-4-yl)methylamine in <Step 6> to obtain the title compound (3.9 g, 49%).
¹H NMR (300 MHz, DMSO-d6): δ 8.92 (s, 1H), 8.42 (s, 1H), 8.04 (br.s, 2H), 7.32 (s, 1H), 4.02 (s, 3H)
MS (ESI⁺, m/z): 221 [M+H]⁺

<Step 7> Preparation of 7-methoxy-quinazolin-4,6-diamine
The procedure of Example 23 was repeated except for using 7-methoxy-6-nitroquinazolin-4-ylamine instead of 7-methoxy-6-nitroquinazolin-4-yl)methylamine in <Step 7> to obtain the title compound (158 mg, 92%).
MS (ESI⁺, m/z): 191 [M+H]⁺
<Step 8> Preparation of tert-butyl(S)-1-((S)-1-((S)-2-(4-amino-7-methoxyquinazolin-6-ylcarbamoyl)pyrrolidin-1-yl)-3,3-dimethyl-1-oxobutan-2-ylamino)-1-oxopropan-2-yl (methyl)carbamate
The procedure of Example 23 was repeated except for using 7-methoxy-quinazolin-4,6-diamine instead of 7-methoxy-N4-methylquinazolin-4,6-diamine in <Step 8> to obtain the title compound (42 mg, 9%).
MS (ESI⁺, m/z): 587[M+H]⁺
<Step 9> Preparation of (S)—N-(4-amino-7-methoxyquinazolin-6-yl)-((S)-3,3-dimethyl-2-((S)-2-(methylamino)propanamido)butanoyl)pyrrolidine-2-carboxamide
The procedure of Example 23 was repeated except for using (1-{1-[2-(4-amino-7-methoxy-quinazolin-6-ylcarbamoyl)pyrrolidine-1-carbonyl]-2,2-dimethylpropylcarbamoyl}ethyl)methylcarbamic acid tert-butylester instead of (1-{1-[2-(7-methoxy-4-methylaminoquinazolin-6-ylcarbamoyl)pyrrolidine-1-carbonyl]-2,2-dimethylpropylcarbamoyl}ethyl)methylcarbamic acid tert-butylester in <Step 9> to obtain the title compound (5 mg, 16%).
¹H NMR (300 MHz, DMSO-d6): δ 10.9 (s, 1H), 9.69 (s, 1H), 8.86 (s, 1H), 8.73 (s, 1H), 8.19 (br.s, 2H), 7.49 (s, 1H), 4.78 (m, 1H), 4.50 (d, 1H), 4.05 (s, 3H), 3.69 (m, 2H), 2.29 (s, 3H), 1.93 (m, 4H), 1.40 (d, 3H), 6.97 (s, 9H)
MS (ESI⁺, m/z): 487 [M+H]⁺

Example 37

Preparation of (S)—N-(4-(3-chloro-4-(3-fluorobenzyloxy)phenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 3-chloro-4-(3-fluorobenzyloxy)aniline instead of 3-chloro-2,4-difluoro-aniline in <Step 4> to obtain the title compound (61 mg, 77%).
¹H NMR (300 MHz, MeOD): δ 9.10 (s, 1H), 8.68 (s, 1H), 7.80 (s, 1H), 7.52 (m, 1H), 7.40 (m, 1H), 7.27 (m, 4H), 7.05 (t, 1H), 5.24 (s, 2H), 4.68 (s, 1H), 4.14 (s, 3H), 3.97 (m, 2H), 3.80 (m, 1H), 2.66 (s, 3H), 2.17 (m, 4H), 1.48 (s, 3H), 1.11 (s, 9H)
MS (ESI⁺, m/z): 719, 721 [M+H]⁺

Example 38

Preparation of (S)—N-(4-(cyclohexylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using cyclohexylamine instead of 3-chloro-2,4-difluoro-aniline in <Step 4> to obtain the title compound (32 mg, 88%).
¹H NMR (300 MHz, DMSO-d6): δ 9.76 (s, 1H), 9.66 (d, 1H), 9.40 (s, 1H), 8.86 (s, 1H), 8.85 (s, 1H), 8.78 (s, 1H) 8.60 (d, 1H), 7.36 (s, 1H), 4.75 (m, 1H), 4.50 (d, 2H), 4.42 (m, 1H), 4.07 (s, 3H), 4.00 (m, 2H), 3.78 (m, 2H), 2.45 (s, 3H), 2.02-1.78 (m, 10H), 1.60-1.42 (m, 4H), 1.33 (d, 3H), 0.99 (s, 9H).

Example 39

Preparation of (S)—N-(4-(biphenyl-4-ylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 4-aminobiphenyl instead of 3-chloro-2,4-difluoro-aniline in <Step 4> to obtain the title compound (5 mg, 3%).
MS (ESI$^+$, m/z): 638 [M+H]$^+$ Example 40

Preparation of (S)-1-((S)-3,3-dimethyl-2-((S)-2-(methylamino)propanamido)butanoyl)-N-(7-methoxy-4-(4-phenoxyphenylamino)quinazolin-6-yl)pyrrolidine-2-carboxamide hydrochloride The procedure of Example 1 was repeated except for using 4-phenoxyaniline instead of 3-chloro-2,4-difluoro-aniline in <Step 4> to obtain the title compound (25 mg, 9%).
$^1$H NMR (300 MHz, DMSO-d6): δ 9.14 (s, 1H), 8.67 (s, 1H), 8.48 (m, 1H), 7.66 (m, 3H), 7.41 (m, 3H), 7.33 (s, 1H), 7.20 (m, 1H), 7.06 (m, 5H), 4.70 (d, 1H), 4.16 (s, 3H), 3.69 (s, 1H), 3.78 (m, 1H), 2.69 (s, 3H), 2.31 (m, 4H), 1.50 (t, 3H), 1.13 (s, 9H)
MS (ESI$^+$, m/z): 654 [M+H]$^+$ Example 41

Preparation of (S)—N-(4-(3-chloro-4-fluorophenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 3-chloro-4-fluoroaniline instead of 3-chloro-2,4-difluoro-aniline in <Step 4> to obtain the title compound (72 mg, 80%).
$^1$H NMR (300 MHz, MeOD): δ 9.23 (s, 1H), 8.77 (s, 1H), 7.37 (m, 4H), 4.71 (m, 1H), 4.20 (s, 3H), 4.02 (m, 2H), 3.84 (m, 1H), 2.69 (s, 3H), 2.22 (m, 4H), 1.52 (d, 3H), 1.13 (s, 9H)
MS (ESI$^+$, m/z): 613, 615 [M+H]$^+$ Example 42

Preparation of (S)—N-(4-(2,3-difluorophenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2,3-difluoroaniline instead of 3-chloro-2,4-difluoro-aniline in <Step 4> to obtain the title compound (47 mg, 73%).
$^1$H NMR (300 MHz, MeOD): δ 9.17 (s, 1H), 8.77 (s, 1H), 7.92 (d, 1H), 7.64 (m, 1H), 7.38 (m, 2H), 4.71 (m, 1H), 4.19 (s, 3H), 4.01 (m, 2H), 3.83 (m, 1H), 2.69 (s, 3H), 2.19 (m, 4H), 1.52 (d, 3H), 1.13 (s, 9H)
MS (ESI$^+$, m/z): 598 [M+H]$^+$ Example 43

Preparation of (S)—N-(4-(3-chloro-2,4-difluorophenylamino)-7-hydroxyquinazolin-6-yl)-1-((S)-3,3-dimethyl-2-((S)-2-(methylamino)propanamido)butanoyl)pyrrolidine-2-carboxamide The procedure of Example 1 was repeated except for using benzyl alcohol instead of NaOMe in <Step 5> and trifluoroacetic acid instead of a 4M HCl/dioxane solution in <Step 8> to obtain the title compound (1.2 mg, 16%).
MS (ESI$^+$, m/z): 618[M+H]$^+$ Example 44

Preparation of (S)—N—((S)-1-((S)-2-(4-((4-bromo-2-fluorophenylamino)-6-methoxyquinazolinyl-7-oxy)methyl)piperidine)-1-carbonyl)-1-pyrrolidinyl)-3,3-dimethyloxobutan-2-yl)-2-(methylamino)propanamide hydrochloride <Step 1> Preparation of 4-benzyloxy-5-methoxy-2-nitrobenzaldehyde Nitric acid (100 mL) was cooled to 0° C., 4-benzyloxy-3-methoxybenzaldehyde (20 g, 82.55 mmol) was added dropwise, and the mixture was stirred at room temperature for 2 hours. After completion of the reaction, distilled water was added thereto and the mixture was stirred for 30 min, followed by filtration of the solid to obtain the title compound (20.52 g, 87%).
$^1$H NMR (300 MHz, CDCl$_3$): δ 10.43 (s, 1H), 7.66 (s, 1H), 7.47-7.34 (m, 6H), 5.26 (s, 2H), 4.01 (s, 3H).
MS (ESI$^+$, m/z): 288 [M+H]$^+$ <Step 2> Preparation of 4-benzyloxy-5-methoxy-2-nitrobenzoic acid The compound (20 g, 69.62 mmol) obtained in <Step 1> was dissolved in acetone (200 mL), and a hot 10% potassium permanganate solution was slowly added thereto at 30° C. The mixture was stirred at 50° C. for 2 hours, and cooled to room temperature. Subsequently, the mixture was filtered through a Celite pad, and washed with acetone and a small amount of hot water. The filtrate was concentrated under reduced pressure and cooled to 0° C. Then, the concentrate was acidified into pH 4 using hydrochloric acid, and the resulting mixture was stirred for 30 min and filtered to the title compound as a solid (18.5 g, 88%).
$^1$H NMR (300 MHz, DMSO-d$_6$): δ 13.58 (brs, 1H), 7.70 (s, 1H), 7.46-7.40 (m, 6H), 7.39 (s, 1H), 5.25 (s, 2H), 3.92 (s, 3H).
MS (ESI$^+$, m/z): 304 [M+H]$^+$ <Step 3> Preparation of 4-benzyloxy-5-methoxy-2-nitrobenzamide The compound (18.5 g, 61.00 mmol) obtained in <Step 2> was dissolved in toluene (200 mL), oxalyl chloride (8 mL, 91.50 mmol) was added thereto, and the mixture was heated under reflux for 2 hours. After removing the solvent under reduced pressure, the resultant was dissolved in 1,4-dioxane (300 mL), and the mixture was stirred under ammonia gas for 2 hours. The resulting solid was dissolved in hexane, filtered, and washed with hexane to obtain the title compound (18.22 g, 99%).
$^1$H NMR (300 MHz, CDCl$_3$): δ 8.05 (s, 1H), 7.68-7.35 (m, 5H), 6.97 (s, 1H), 5.80 (brs, 2H), 5.22 (s, 2H), 3.99 (s, 2H).
MS (ESI$^+$, m/z): 303 [M+H]$^+$ <Step 4> Preparation of 2-amino-4-benzyloxy-5-methoxybenzamide The compound (17.9 g, 59.22 mmol) obtained in <Step 3> was dissolved in acetic acid (250 mL), and the mixture was heated to 90° C., followed by stirring for 10 min. Then, iron (29.8 g, 532.95 mmol) was added and the mixture was heated under reflux for 1 hour. The mixture was cooled to 50° C., and filtered through a Celite pad. The filtrate was cooled to 0° C., acidified with a 10% hydrochloric acid solution, and the resulting solid was filtered. Then, the white solid was dissolved in hot water, basified with 15% sodium hydroxide, and the resulting solid was filtered. The solid thus obtained was dried to obtain the title compound (5.2 g, 32%).

$^1$H NMR (300 MHz, DMSO-d$_6$): δ 8.05 (s, 1H), 7.68~7.35 (m, 5H), 6.97 (s, 1H), 5.80 (brs, 2H), 5.22 (s, 2H), 3.99 (s, 2H).

MS (ESI$^+$, m/z): 273 [M+H]$^+$

<Step 5> Preparation of 7-benzyloxy-6-methoxy-3H-quinazolin-4-one

The compound (5 g, 18.36 mmol) obtained in <Step 4> was dissolved in 1,4-dioxane (60 mL), Gold's reagent (4.5 g, 27.54 mmol) was added thereto, and the mixture was heated under reflux for 12 hours. Then, sodium acetate (1.53 g, 18.36 mmol) and acetic acid (530 μL) were added, and the solution was heated under reflux for 3 hours. The solution was concentrated under reduced pressure, and water was added. The resulting solid was filtered to obtain the title compound (4.5 g, 87%).

$^1$H NMR (300 MHz, CDCl$_3$): δ 7.97 (s, 1H), 7.64 (s, 1H), 7.55-7.35 (m, 5H), 7.20 (s, 1H), 5.29 (s, 2H), 4.01 (s, 3H).

MS (ESI$^+$, m/z): 283 [M+H]$^+$

<Step 6> Preparation of 7-benzyloxy-4-chloro-6-methoxyquinazoline hydrochloride

The compound (3.7 g, 13.10 mmol) obtained in <Step 5> was mixed with dimethylformamide (2 mL, a catalytic amount), thionyl chloride (18 mL, 262.0 mmol) and phosphorus oxychloride (1.8 mL, 19.65 mmol), and the mixture was then heated under reflux for 2 hours. The mixture was concentrated under reduced pressure and ice water was added thereto. The resulting mixture was filtered to obtain the title compound as a brown solid (4.4 g, 100%).

$^1$H NMR (300 MHz, CDCl$_3$): δ 8.85 (s, 1H), 7.51-7.35 (m, 7H), 5.33 (s, 2H), 4.07 (s, 3H).

MS (ESI$^+$, m/z): 337[M+H]$^+$

<Step 7> Preparation of 7-(benzyloxy)-N-(4-bromo-2-fluorophenyl)-6-methoxyquinazolin-4-amine The compound obtained in <Step 6> was dissolved in isopropanol (50 mL), 4-bromo-2-fluorophenylamine (3.22 g, 16.94 mmol) was added thereto, and the mixture was heated under reflux for 2 hours. The mixture was cooled to room temperature, filtered, and the resulting solid was filtered to obtain the title compound as a brown solid (4.0 g, 62%).

$^1$H NMR (300 MHz, CDCl$_3$): δ 8.24 (s, 1H), 7.59-7.35 (m, 9H), 7.05 (s, 1H0, 5.33 (s, 2H), 4.07 (s, 3H).

MS (ESI$^+$, m/z): 454[M+H]$^+$

<Step 8> Preparation of 4-(4-bromo-2-fluorophenylamino)-6-methoxyquinazolin-7-ol The compound (2.3 g, 5.06 mmol) obtained in <Step 7> was diluted with trifluoroacetic acid (10 mL) and the solution was stirred by heating for 2 hours. The solution was neutralized successively with methanol and water, basified with a ammonium hydroxide solution, and the resulting solid was filtered to obtain the title compound (1.0 g, 44%).

$^1$H NMR (300 MHz, DMSO-d$_6$): δ 8.25 (s, 1H), 7.74 (s, 1H), 7.64 (d, J=10.2 Hz, 1H), 7.50-7.47 (m, 2H), 7.20 (brs, 1H, NH), 7.01 (s, 1H), 3.92 (s, 3H).

MS (ESI$^+$, m/z): 364 [M+H]$^+$

<Step 9> Preparation of N-(4-bromo-2-fluorophenyl)-6-methoxy-7-(piperidinyl-4-methoxy)quinazolin-4-amine hydrochloride The compound (800 mg, 2.20 mmol) obtained in <Step 8> was dissolved in dichloromethane (30 mL), and triphenylphosphine (1.73 g, 6.60 mmol), DIAD (1.3 mL, 6.60 mmol) and t-butyl 4-(hydroxymethyl)piperidine-1-carboxylate (662 mg, 3.08 mmol) were added thereto, followed by stirring at room temperature for 3 hours. The mixture was extracted with ethyl acetate. The organic layer was washed with water, dried over magnesium sulfate, and filtered and concentrated under reduced pressure. The resulting residue was purified by column chromatography (ethyl acetate/hexane=2/1, ethyl acetate). The resulting intermediate was dissolved in ethyl acetate (25 mL) and a 4M-HCl/dioxane solution (5.5 mL) was added thereto, followed by stirring at room temperature for 10 hours. The solid thus obtained was filtered to obtain the title compound (410 mg, 2 Step 40%).

$^1$H NMR (300 MHz, MeOD): δ 8.24 (s, 1H), 7.60 (s, 1H), 7.59-7.31 (m, 3H), 7.06 (s, 1H), 3.92 (s, 3H), 3.90 (s, 2H), 3.04-2.99 (m, 2H), 2.61-2.53 (m, 2H), 1.95-1.91 (m, 1H), 1.83-1.78 (m, 2H), 1.32-1.25 (m, 2H).

MS (ESI$^+$, m/z): 497 [M+H]$^+$

<Step 10> Preparation of (S)-(4-((4-bromo-2-fluorophenylamino)-6-methoxyquinazolinyl-7-oxy)methyl)-1-piperidinyl)-2-pyrrolidinyl)methanone hydrochloride The compound (100 mg, 0.22 mmol) obtained in <Step 9> was dissolved in dichloromethane (2 mL), and (S)-1-(t-butoxycarbonyl)proline (70 mg, 0.33 mmol), HATU (125 mg, 0.33 mmol) and DIPEA (77 uL, 0.44 mmol) were added thereto, followed by stirring at room temperature for 3 hours. The mixture was extracted with ethyl acetate. The organic layer was washed with water, dried over magnesium sulfate, and filtered and concentrated under reduced pressure. The resulting residue was purified by column chromatography (dichloromethane/methanol=30/1). The resulting intermediate was dissolved in ethyl acetate (2 mL) and a 4M-HCl/dioxane solution (0.4 mL) was added thereto, followed by stirring at room temperature for 10 hours. The solid thus obtained was filtered to obtain the title compound (94 mg, 2 Step 100%).

$^1$H NMR (300 MHz, CDCl$_3$): δ 8.69 (s, 1H), 8.51 (t, J=8.4 Hz, 1H), 7.35 (d, J=9.0 Hz, 2H), 7.24 (s, 1H), 7.01 (s, 1H), 4.73-4.69 (m, 1H), 4.04 (s, 3H), 4.02 (s, 2H), 3.95-3.89 (m, 2H), 3.17-3.07 (m, 2H), 2.84-2.68 (m, 2H), 2.40-1.95 (m, 2H), 1.83-1.67 (m, 2H), 1.40-1.31 (m, 3H).

MS (ESI$^+$, m/z): 594 [M+H]$^+$

<Step 11> Preparation of (S)-2-amino-1-((S)-2-(4-((4-bromo-2-fluorophenylamino)-6-methoxyquinazolinyl-7-oxy)methyl)-1-piperidine)-1-carbonyl)-1-pyrrolidinyl)-3,3-dimethylbutan-1-one hydrochloride The compound (90 mg, 0.16 mmol) obtained in <Step 10> was dissolved in dichloromethane (2 mL), and (S)-2-(t-butoxycarbonylamino)-t-butylglycine (56 mg, 0.24 mmol), EDC (91 mg, 0.24 mmol) and DIPEA (83 μL, 0.48 mmol) were added thereto, followed by stirring at room temperature for 3 hours. The mixture was extracted with ethyl acetate. The organic layer was washed with water, dried over magnesium sulfate, and filtered and concentrated under reduced pressure. The resulting residue was purified by column chromatography (dichloromethane/methanol=30/1). The resulting intermediate was dissolved in ethyl acetate (2 mL), and a 4M-HCl/dioxane solution (0.3 mL) was added thereto, followed by stirring at room temperature for 10 hours. The resulting mixture was filtered to obtain the title compound as a solid (69 mg, 2 Step 79%).

¹H NMR (300 MHz, CDCl₃): δ 8.69 (s, 1H), 8.48-8.41 (m, 1H, NH), 7.38 (s, 1H), 7.35 (s, 1H), 7.26 (s, 1H), 7.23 (s, 1H), 7.08-7.02 (m, 1H), 5.30-5.25 (m, 1H), 4.95-4.93 (m, 1H), 4.65-4.61 (m, 1H), 4.36-4.33 (m, 1H), 4.03 (s, 3H), 3.97 (s, 2H), 3.87-3.85 (m, 2H), 3.76-3.70 (m, 2H), 3.22-3.14 (m, 2H), 2.11-1.70 (m, 8H), 1.06 (s, 9H).

MS (ESI⁺, m/z): 671 [M+H]⁺

<Step 12> Preparation of (S)—N—((S)-1-((S)-2-(4-((4-bromo-2-fluorophenylamino)-6-methoxyquinazolinyl-7-oxy)methyl)piperidine)-1-carbonyl)-1-pyrrolidinyl)-3,3-dimethyloxobutan-2-yl)-2-(methylamino)propanamide hydrochloride The compound (47 mg, 0.070 mmol) obtained in <Step 11> was dissolved in dichloromethane (1 mL), and (S)-2-(t-butoxycarbonyl(methyl)amino)-alanine (17 mg, 0.084 mmol), EDC (20 mg, 0.11 mmol) and DIPEA (37 µL, 0.21 mmol) were added thereto, followed by stirring at room temperature for 3 hours. The mixture was extracted with ethyl acetate. The organic layer was washed with water, dried over magnesium sulfate, and filtered and concentrated under reduced pressure. The resulting residue was purified by column chromatography (dichloromethane/methanol=30/1). The resulting intermediate was dissolved in ethyl acetate (1 mL), and a 4M–HCl/dioxane solution (0.14 mL) was added thereto, followed by stirring at room temperature for 10 hours. The resulting mixture was filtered to obtain the title compound as a solid (30 mg, 2 Step 62%).

¹H NMR (300 MHz, DMSO-d₆): δ 11.81 (brs, 1H, NH), 9.45 (brs, 1H, NH), 8.80 (brs, 1H, NH), 8.73 (s, 1H), 8.53-8.45 (m, 1H), 8.39 (s, 1H), 7.70 (d, J=9.0 Hz, 1H), 7.52-7.41 (m, 3H), 4.78-4.76 (m, 1H), 4.48-4.45 (m, 1H), 4.34-4.30 (m, 1H), 4.00 (m, 2H), 3.96 (s, 3H), 3.89-3.88 (m, 1H), 3.70-3.69 (m, 1H), 3.54-3.38 (m, 4H), 3.07-3.03 (m, 1H), 2.62-2.58 (m, 1H), 2.38 (s, 3H), 2.12-2.10 (m, 2H), 1.84-1.62 (m, 5H), 1.26 (d, J=6.6 Hz, 3H), 0.96 (s, 9H).

MS (ESI⁺, m/z): 756 [M+H]⁺

Example 45

Preparation of (S)—N-(4-(3-chloro-2,4-difluorophenylamino)-7-methoxyquinazolin-6-yl)-1-((2S,3R)-2-((S)-2-(methylamino)propanamido)-3-(prop-2-ynyloxy)butanoyl)pyrrolidine-2-carboxamide hydrochloride The procedure of Example 1 was repeated except for using 2-Boc-3-(ethynyloxy)butanoic acid instead of Boc-Tle-OH in <Step 3> of Preparation Example 1 to obtain the title compound (300 mg, 9%).

¹H NMR (300 MHz, MeOD): δ 9.16 (s, 1H), 8.68 (s, 1H), 7.51 (m, 1H), 7.28 (m, 2H), 4.71 (d, 1H), 4.14 (s, 3H), 3.92 (m, 2H), 3.74 (m, 2H), 3.62 (s, 3H), 3.45 (m, 2H), 2.64 (s, 3H), 2.25 (m, 2H), 2.15 (m, 2H), 1.50 (m, 3H), 1.25 (m, 3H)

MS (ESI⁺, m/z): 658 [M+H]⁺

Example 46

Preparation of (2S,4R)-4-(benzyloxy)-N-(4-(3-chloro-2,4-difluorophenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using Boc-Hyp(Bzl)-OH instead of Boc-Tle-OH in <Step 3> of Preparation Example 1 to obtain the title compound (35 mg, 7%).

MS (ESI⁺, m/z): 738 [M+H]⁺

Example 47

Preparation of (S)-1-((S)-3,3-dimethyl-2-((S)-2-(methylamino)propanamido)butanoyl)-N-(7-methoxy-4-(2-morpholinophenylamino)quinazolin-6-yl)pyrrolidine-2-carboxamide <Step 5> Preparation of 7-fluoro-N-(2-morpholinophenyl)-6-nitroquinazolin-4-amine The procedure of Example 23 was repeated except for using 2-morpholinoaniline instead of methylamine in <Step 5> to obtain the title compound (300 mg, 85%).

MS (ESI⁺, m/z): 370[M+H]⁺

<Step 6> Preparation of 7-methoxy-N-(2-morpholinophenyl)-6-nitroquinazolin-4-amine The procedure of Example 23 was repeated except for using 7-fluoro-N-(2-morpholinophenyl)-6-nitroquinazolin-4-amine instead of (7-fluoro-6-nitroquinazolin-4-yl)methylamine in <Step 6> to obtain the title compound (200 mg, 60%).

MS (ESI, m/z): 382 [M+H]⁺

<Step 7> Preparation of 7-methoxy-N4-(2-morpholinophenyl)quinazolin-4,6-diamine

The procedure of Example 23 was repeated except for using 7-methoxy-N-(2-morpholinophenyl)-6-nitroquinazolin-4-amine instead of 7-methoxy-6-nitroquinazolin-4-yl)methylamine in <Step 7> to obtain the title compound (65 mg, 35%).

MS (ESI⁺, m/z): 352 [M+H]⁺

<Step 8> Preparation of tert-butyl(S)-1-((S)-1-((S)-2-(7-methoxy-4-(2-morpholinophenylamino)quinazolin-6-ylcarbamoyl)pyrrolidin-1-yl)-3,3-dimethyl-1-oxobutan-2-ylamino)-1-oxopropan-2-yl(methyl)carbamate The procedure of Example 23 was repeated except for using 7-methoxy-N4-(2-morpholinophenyl)quinazolin-4,6-diamine instead of 7-methoxy-N4-methylquinazolin-4,6-diamine in <Step 8> to obtain the title compound (119 mg, 85%).

MS (ESI⁺, m/z): 748 [M+H]⁺

<Step 9> Preparation of (S)-1-((S)-3,3-dimethyl-2-((S)-2-(methylamino)propanamido)butanoyl)-N-(7-methoxy-4-(methylamino)quinazolin-6-yl)pyrrolidine-2-carboxamide The procedure of Example 23 was repeated except for using [1-(1-{2-[7-methoxy-4-(naphthalen-2-ylamino)quinazolin-6-ylcarbamoyl]pyrrolidine-1-carbonyl}-2,2-dimethylpropylcarbamoyl)ethyl]methylcarbamic acid tert-butylester instead of (1-{1-[2-(7-methoxy-4-methylaminoquinazolin-6-ylcarbamoyl)pyrrolidine-1-carbonyl]-2,2-dimethylpropylcarbamoyl}ethyl)methylcarbamic acid tert-butylester in <Step 9> to obtain the title compound (26 mg, 25%).

¹H NMR (300 MHz, DMSO-d6): δ 9.97 (s, 1H), 9.60 (s, 1H), 8.96 (s, 1H), 8.54 (m, 1H), 8.29 (s, 1H), 7.88 (m, 5H), 7.47 (m, 3H), 4.80 (m, 1H), 4.33 (d, 1H), 3.96 (s, 3H), 3.75 (m, 2H), 2.19 (s, 3H), 1.96 (m, 4H), 1.14 (d, 3H), 0.95 (s, 9H)

MS (ESI⁺, m/z): 612 [M+H]⁺

Example 48

Preparation of (S)—N-(4-(3-chloro-2,4-difluorophenylamino)quinazolin-6-yl)-1-((S)-3,3-dimethyl-2-((S)-2-(methylamino)propanamido)butanoyl)pyrrolidine-2-carboxamide <Step 4> Preparation of 4-chloro-6-nitroquinazoline The procedure of Example 1 was repeated except for using 6-nitroquinazolin-4(3H)-one instead of 7-fluoro-6-nitroquinazolin-4(3H)-one in <Step 4> to obtain the title compound (448 mg, 99%).

¹H NMR (300 MHz, DMSO-d6): δ 8.78 (s, 1H), 8.54 (d, 1H), 8.39 (s, 1H), 7.87 (d, 1H)

MS (ESI⁺, m/z): 210 [M+H]⁺

<Step 5> Preparation of N-(3-chloro-2,4-difluorophenyl)-6-nitroquinazolin-4-amine The procedure of Example 23 was repeated except for using 3-chloro-2,4-difluoroaniline instead of methylamine in <Step 5> to obtain the title compound (535 mg, 74%).

¹H NMR (300 MHz, DMSO-d6): δ 9.76 (s, 1H), 8.90 (s, 1H), 8.74 (d, 1H), 8.12 (d, 1H), 7.61 (m, 1H), 7.50 (m, 1H)

MS (ESI⁺, m/z): 338 [M+H]⁺

<Step 6> Preparation of N4-(3-chloro-2,4-difluorophenyl)quinazolin-4,6-diamine

Iron (888 mg, 15.9 mmol) was refluxed under a solvent of ethanol (4 mL) and distilled water for 30 min, and the compound obtained in <Step 5> was added thereto, followed by refluxing for 2 hours. The mixture was filtered through a Celite pad and distilled under reduced pressure. The resulting oil was diluted with ethyl acetate (30 mL) and washed with an aqueous solution of sodium bicarbonate. The organic layer was dried over sodium sulfate, and filtered and distilled under reduced pressure to obtain the title compound (406 mg, 83%).

MS (ESI⁺, m/z): 308 [M+H]⁺

<Step 7> Preparation of tert-butyl(S)-1-((S)-1-((S)-2-(4-(3-chloro-2,4-difluorophenylamino)quinazolin-6-ylcarbamoyl)pyrrolidin-1-yl)-3,3-dimethyl-1-oxobutan-2-ylamino)-1-oxopropan-2-yl(methyl)carbamate The procedure of Example 23 was repeated except for using the compound obtained in <Step 6> instead of 7-methoxy-N4-methylquinazolin-4,6-diamine in <Step 8> to obtain the title compound (439 mg, 85%).

MS (ESI⁺, m/z): 703 [M+H]⁺

<Step 8> Preparation of (S)—N-(4-(3-chloro-2,4-difluorophenylamino)quinazolin-6-yl)-1-((S)-3,3-dimethyl-2-((S)-2-(methylamino)propanamido)butanoyl)pyrrolidine-2-carboxamide The procedure of Example 23 was repeated except for using tert-butyl(S)-1-((S)-1-((S)-2-(4-(3-chloro-2,4-difluorophenylamino)quinazolin-6-ylcarbamoyl)pyrrolidin-1-yl)-3,3-dimethyl-1-oxobutan-2-ylamino)-1-oxopropan-2-yl(methyl)carbamate instead of (1-{1-[2-(7-methoxy-4-methylaminoquinazolin-6-ylcarbamoyl)pyrrolidine-1-carbonyl]-2,2-dimethylpropylcarbamoyl}ethyl)methylcarbamic acid tert-butylester in <Step 9> to obtain the title compound (45 mg, 12%).

¹H NMR (300 MHz, DMSO-d6): δ 10.5 (s, 1H), 9.97 (s, 1H), 8.67 (s, 1H), 8.42 (s, 1H), 7.80 (m, 3H), 7.51 (m, 1H), 7.35 (m, 1H), 4.53 (m, 2H), 3.66 (m, 2H), 2.97 (m, 1H), 2.24 (s, 3H), 1.98 (m, 4H), 1.15 (d, 3H), 0.97 (s, 9H)

MS (ESI⁺, m/z): 603 [M+H]⁺

Example 49

Preparation of (S)-1-((S)-3,3-dimethyl-2-((S)-2-(methylamino)propanamido)butanoyl)-N-(7-methoxy-4-(4-methoxyphenylamino)quinazolin-6-yl)pyrrolidine-2-carboxamide hydrochloride The procedure of Example 1 was repeated except for using p-anisidine instead of 3-chloro-2,4-difluoro-aniline in <Step 4> to obtain the title compound (57 mg, 8%).

¹H NMR (300 MHz, DMSO-d6): δ 10.20 (s, 1H), 9.73 (m, 1H), 8.96 (m, 2H), 8.57 (d, 1H), 8.26 (d, 1H), 7.95 (d, 1H), 7.30 (d, 1H), 7.04 (m, 4H), 4.56 (m, 1H), 4.42 (d, 1H), 3.96 (s, 3H), 3.93 (s, 1H), 3.66 (m, 3H), 3.54 (s, 7H), 3.45 (m, 1H), 2.84 (m, 2H), 2.48 (s, 3H), 1.86 (m, 3H), 1.71 (m, 4H), 1.30 (d, 3H), 0.98 (s, 9H), 0.88 (m, 3H)

MS (ESI⁺, m/z): 592 [M+H]⁺

Example 50

Preparation of (S)—N-(4-(3,4-dihydroquinoline-1(2H)-yl)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 1,2,3,4-tetrahydroquinoline instead of 3-chloro-2,4-difluoroaniline in <Step 4> to obtain the title compound (52 mg, 8%).

MS (ESI⁺, m/z): 602 [M+H]⁺

Example 51

Preparation of (S)—N-(4-(5-chlorobenzo[d][1,3]dioxol-4-ylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 4-chlorobenzo[d][1,3]dioxol-5-amine instead of 3-chloro-2,4-difluoro-aniline in <Step 4> to obtain the title compound (136 mg, 75%).

¹H NMR (300 MHz, MeOD): δ 9.07 (s, 1H), 8.61 (s, 1H), 7.25 (s, 1H), 6.97 (d, 1H), 6.72 (d, 1H), 6.02 (s, 2H), 4.89-4.87 (m, 1H), 4.65-4.63 (d, 1H), 4.03 (s, 3H), 4.00-3.70 (m, 2H), 2.80 (s, 3H), 2.56-2.52 (d, 1H), 2.12-1.72 (m, 4H), 1.34 (d, 3H), 1.00 (s, 9H)

MS (ESI⁺, m/z): 641 [M+H]⁺

Example 52

Preparation of (S)—N-(4-(2,3-dihydro-1H-inden-5-ylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 5-aminoindane instead of 3-chloro-2,4-difluoro-aniline in <Step 4> to obtain the title compound (172 mg, 9%).

¹H NMR (300 MHz, DMSO-d6): δ 11.09 (s, 1H), 10.57 (s, 1H), 8.94 (m, 1H), 8.74 (m, 1H), 8.65 (s, 1H), 8.53 (m, 2H), 8.43 (s, 1H), 7.76 (s, 1H), 7.45 (s, 4H), 7.16 (m, 3H), 4.58 (m, 1H), 4.42 (m, 2H), 3.93 (m, 3H), 3.66 (m, 1H), 2.28 (m, 2H), 2.06 (m, 7H), 1.97 (m, 2H), 1.30 (d, 3H), 0.95 (s, 9H)

MS (ESI⁺, m/z): 602 [M+H]⁺

Example 53

Preparation of (S)-1-((S)-3,3-dimethyl-2-((S)-2-(methylamino)propanamido)butanoyl)-N-(7-methoxy-4-(quinoline-6-ylamino)quinazolin-6-yl)pyrrolidine-2-carboxamide <Step 5> Preparation of 7-fluoro-6-nitro-N-(quinolin-6-yl)quinazolin-4-amine The procedure of Example 23 was repeated except for using 6-aminoquinoline instead of methylamine in <Step 5> to obtain the title compound (578 mg, 78%).

MS (ESI⁺, m/z): 336 [M+H]⁺

<Step 6> Preparation of 7-methoxy-6-nitro-N-(quinolin-6-yl)quinazolin-4-amine

The procedure of Example 23 was repeated except for using the compound obtained in <Step 5> instead of (7-fluoro-6-nitroquinazolin-4-yl)methylamine in <Step 6> to obtain the title compound (189 mg, 32%).

$^1$H NMR (300 MHz, DMSO-d6): δ 10.4 (s, 1H), 9.34 (s, 1H), 9.32 (d, 1H), 8.72 (s, 1H), 8.51 (d, 1H), 8.35 (d, 1H), 8.16 (d, 1H), 8.04 (d, 1H), 7.51 (m, 2H), 4.07 (s, 3H)

MS (ESI$^+$, m/z): 348 [M+H]$^+$

<Step 7> Preparation of 7-methoxy-N4-(quinoline-6-yl)quinazolin-4,6-diamine

The procedure of Example 23 was repeated except for using the compound obtained in <Step 6> instead of 7-methoxy-6-nitroquinazolin-4-yl)methylamine in <Step 7> to obtain the title compound (55 mg, 32%).

MS (ESI$^+$, m/z): 318 [M+H]$^+$

<Step 8> Preparation of tert-butyl(S)-1-((S)-1-((S)-2-(7-methoxy-4-(quinoline-6-ylamino)quinazolin-6-yl)pyrrolidin-1-yl)-3,3-dimethyl-1-oxobutan-2-ylamino)-1-oxopropan-2-yl(methyl)carbamate The procedure of Example 23 was repeated except for using the compound obtained in <Step 7> instead of 7-methoxy-N4-methylquinazolin-4,6-diamine in <Step 8> to obtain the title compound (76 mg, 62%).

MS (ESI$^+$, m/z): 714 [M+H]$^+$

<Step 9> Preparation of (S)-1-((S)-3,3-dimethyl-2-((S)-2-(methylamino)propanamido)butanoyl)-N-(7-methoxy-4-(quinoline-6-ylamino)quinazolin-6-yl)pyrrolidine-2-carboxamide The procedure of Example 23 was repeated except for using the compound obtained in <Step 8> instead of (1-{1-[2-(7-methoxy-4-methylaminoquinazolin-6-ylcarbamoyl)pyrrolidine-1-carbonyl]-2,2-dimethylpropylcarbamoyl}ethyl)methylcarbamic acid tert-butylester in <Step 9> to obtain the title compound (15 mg, 23%).

$^1$H NMR (300 MHz, DMSO-d6): δ 10.0 (s, 1H), 9.63 (s, 1H), 8.97 (s, 1H), 8.79 (d, 1H), 8.55 (s, 1H), 8.38 (s, 1H), 8.30 (d, 1H), 8.15 (d, 1H), 7.97 (d, 1H), 7.87 (d, 1H), 7.48 (q, 1H), 7.30 (s, 1H), 4.78 (m, 1H), 4.53 (d, 1H), 4.02 (s, 3H), 3.75 (m, 2H), 2.97 (m, 1H), 2.18 (s, 3H), 2.00 (m, 4H), 1.11 (d, 3H), 0.96 (s, 9H)

MS (ESI$^+$, m/z): 614 [M+H]$^+$

Example 54

Preparation of (S)—N-(4-(1H-indazol-5-ylamino)-7-methoxyquinazolin-6-yl)-1-((S)-3,3-dimethyl-2-((S)-2-(methylamino)propanamido)butanoyl)pyrrolidine-2-carboxamide <Step 5> Preparation of 7-fluoro-N-(1H-indazol-5-yl)-6-nitroquinazolin-4-amine The procedure of Example 23 was repeated except for using 5-aminoindazole instead of methylamine in <Step 5> to obtain the title compound (710 mg, 99%).

MS (ESI$^+$, m/z): 325 [M+H]$^+$

<Step 6> Preparation of N-(1H-indazol-5-yl)-7-methoxy-6-nitroquinazolin-4-amine

The procedure of Example 23 was repeated except for using the compound obtained in <Step 5> instead of (7-fluoro-6-nitroquinazolin-4-yl)methylamine in <Step 6> to obtain the title compound (158 mg, 21%).

$^1$H NMR (300 MHz, DMSO-d6): δ 9.29 (s, 1H), 8.62 (s, 1H), 8.23 (s, 1H), 7.98 (s, 1H), 7.69 (d, 1H), 7.42 (m, 3H), 4.01 (s, 3H)

MS (ESI$^+$, m/z): 337 [M+H]$^+$

<Step 7> Preparation of 7-methoxy-N4-(quinoline-6-yl)quinazolin-4,6-diamine

The procedure of Example 23 was repeated except for using the compound obtained in <Step 6> instead of 7-methoxy-6-nitroquinazolin-4-yl)methylamine in <Step 7> to obtain the title compound (87 mg, 60%).

MS (ESI$^+$, m/z): 307 [M+H]$^+$

<Step 8> Preparation of tert-butyl(S)-1-((S)-1-((S)-2-(4-(1H-indazol-5-ylamino)-7-methoxyquinazolin-6-ylcarbamoyl)pyrrolidin-1-yl)-3,3-dimethyl-1-oxobutan-2-ylamino)-1-oxopropan-2-yl(methyl)carbamate The procedure of Example 23 was repeated except for using the compound obtained in <Step 7> instead of 7-methoxy-N4-methylquinazolin-4,6-diamine in <Step 8> to obtain the title compound (143 mg, 72%).

MS (ESI$^+$, m/z): 703 [M+H]$^+$

<Step 9> Preparation of (S)—N-(4-(1H-indazol-5-ylamino)-7-methoxyquinazolin-6-yl)-1-((S)-3,3-dimethyl-2-((S)-2-(methylamino)propanamido)butanoyl)pyrrolidine-2-carboxamide The procedure of Example 23 was repeated except for using the compound obtained in <Step 8> instead of (1-{1-[2-(7-methoxy-4-methylaminoquinazolin-6-ylcarbamoyl)pyrrolidine-1-carbonyl]-2,2-dimethylpropylcarbamoyl}ethyl)methylcarbamic acid tert-butylester in <Step 9> to obtain the title compound (23 mg, 19%).

$^1$H NMR (300 MHz, DMSO-d6): δ 10.4 (s, 1H), 9.29 (s, 1H), 8.68 (d, 2H), 8.50 (s, 1H), 8.17 (d, 1H), 7.92 (d, 1H), 7.85 (d, 1H), 7.49 (s, 1H), 5.62 (m, 1H), 4.59 (d, 1H), 4.06 (s, 3H), 3.81 (m, 2H), 2.97 (m, 1H), 2.15 (s, 3H), 2.01 (m, 4H), 1.10 (d, 3H), 0.94 (s, 9H)

MS (ESI$^+$, m/z): 602 [M+H]$^+$

Example 55

Preparation of (S)-1-((S)-3,3-dimethyl-2-((S)-2-(methylamino)propanamido)butanoyl)-N-(4-(4-fluorophenylamino)-7-methoxyquinazolin-6-yl)pyrrolidine-2-carboxamide The procedure of Example 1 was repeated except for using 4-fluoroaniline instead of 3-chloro-2,4-difluoro-aniline in <Step 4> to obtain the title compound (100 mg, 5%).

$^1$H NMR (300 MHz, MeOD): δ 8.91 (s, 1H), 8.45 (s, 1H), 7.65 (m, 2H), 7.22 (s, 1H), 7.12 (m, 2H), 4.69 (s, 1H), 4.07 (s, 3H), 3.84 (d, 2H), 3.82 (m, 1H), 3.51 (m, 1H), 2.69 (s, 3H), 2.18 (m, 5H), 1.50 (d, 3H), 1.10 (s, 9H)

MS (ESI$^+$, m/z): 580 [M+H]$^+$

Example 56

Preparation of (S)—N-(4-(4-chlorophenylamino)-7-methoxyquinazolin-6-yl)-1-((S)-3,3-dimethyl-2-((S)-2-(methylamino)propanamido)butanoyl)pyrrolidine-2-carboxamide The procedure of Example 1 was repeated except for using 4-chloroaniline instead of 3-chloro-2,4-difluoro-aniline in <Step 4> to obtain the title compound (15 mg, 8%).

$^1$H NMR (300 MHz, MeOD): δ 8.88 (s, 1H), 8.45 (s, 1H), 7.73 (d, 2H), 7.36 (d, 2H), 7.22 (s, 1H), 4.68 (m, 1H), 4.07 (m, 3H), 3.96 (m, 2H), 2.65 (m, 5H), 2.21 (m, 6H), 1.48 (m, 5H), 1.28 (m, 2H), 1.11 (s, 9H), 1.00 (m, 5H)

MS (ESI, m/z): 596 [M+H]$^+$

Example 57

Preparation of (S)-1-((S)-3,3-dimethyl-2-((S)-2-(methylamino)propanamido)butanoyl)-N-(7-methoxy-4-(3-methoxyphenylamino)quinazolin-6-yl)pyrrolidine-2-carboxamide hydrochloride The procedure of Example 1 was repeated except for using 3-methoxyaniline instead of 3-chloro-2,4-difluoro-aniline in <Step 4> to obtain the title compound (55 mg, 67%).

$^1$H NMR (300 MHz, MeOD): δ 8.56 (s, 1H), 7.46 (s, 1H), 7.31-7.23 (m, 3H), 7.19 (s, 1H), 6.71-6.68 (m, 1H), 4.90-4.89 (m, 1H), 4.66-4.63 (m, 1H), 4.03 (s, 3H), 3.84 (s, 3H), 3.74-3.70 (m, 1H), 2.80 (s, 3H), 2.52 (br, 2H), 2.15-2.10 (m, 4H), 1.34 (d, 3H), 0.98 (s, 9H)

MS (ESI$^+$, m/z): 591 [M+H]$^+$

Example 58

Preparation of (S)—N-(4-(2,4-dichlorophenylamino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2,4-dichloro aniline instead of 3-chloro-2,4-difluoro-aniline in <Step 4> to obtain the title compound (78 mg, 70%).

$^1$H NMR (300 MHz, MeOD): δ 9.15 (s, 1H), 8.68 (s, 1H), 8.65 (d, 1H), 7.88 (s, 1H), 7.46 (s, 1H), 7.32 (d, 1H), 7.27 (s, 1H), 4.89-4.86 (m, 1H), 4.66-4.63 (m, 1H), 4.04 (s, 3H), 3.99-3.91 (m, 1H), 2.88 (s, 3H), 2.60-2.55 (m, 1H), 2.08-1.96 (m, 4H), 1.34 (d, 3H), 1.00 (s, 9H)

MS (ESI$^+$, m/z): 630 [M+H]$^+$

Example 59

Preparation of (S)—N-(4-(2,6-difluorophenylamino)-7-methoxyquinazolin-6-yl)-1-((S)-3,3-dimethyl-2-((S)-2-(methylamino)propanamido)butanoyl)pyrrolidine-2-carboxamide <Step 5> Preparation of N-(2,6-difluorophenyl)-7-fluoro-6-nitroquinazolin-4-amine The procedure of Example 23 was repeated except for using 2,6-difluoroaniline instead of methylamine in <Step 5> to obtain the title compound (378 mg, 54%).

$^1$H NMR (300 MHz, DMSO-d6): δ 8.69 (s, 1H), 7.99 (d, 1H), 7.67 (br.s, 2H), 7.05 (s, 1H)

MS (ESI$^+$, m/z): 321 [M+H]$^+$

<Step 6> Preparation of N-(2,6-difluorophenyl)-7-methoxy-6-nitroquinazolin-4-amine The procedure of Example 23 was repeated except for using the compound obtained in <Step 5> instead of (7-fluoro-6-nitroquinazolin-4-yl)methylamine in <Step 6> to obtain the title compound (134 mg, 34%).

$^1$H NMR (300 MHz, DMSO-d6): δ 10.3 (br. s, 1H), 9.20 (s, 1H), 8.52 (s, 1H), 7.50 (s, 1H), 7.42 (m, 1H), 7.25 (m, 2H), 4.06 (s, 3H)

MS (ESI$^+$, m/z): 333 [M+H]$^+$

<Step 7> Preparation of N4-(2,6-difluorophenyl)-7-methoxyquinazolin-4,6-diamine

The procedure of Example 23 was repeated except for using the compound obtained in <Step 6> instead of 7-methoxy-6-nitroquinazolin-4-yl)methylamine in <Step 7> to obtain the title compound (85 mg, 70%).

MS (ESI$^+$, m/z): 303 [M+H]$^+$

<Step 8> Preparation of tert-butyl(S)-1-((S)-1-((S)-2-(4-(2,6-difluorophenylamino)-7-methoxyquinazolin-6-ylcarbamoyl)pyrrolidin-1-yl)-3,3-dimethyl-1-oxobutan-2-ylamino)-1-oxopropan-2-yl(methyl)carbamate The procedure of Example 23 was repeated except for using the compound obtained in <Step 7> instead of 7-methoxy-N4-methylquinazolin-4,6-diamine in <Step 8> to obtain the title compound (118 mg, 60%).

MS (ESI$^+$, m/z): 698 [M+H]$^+$

<Step 9> Preparation of (S)—N-(4-(2,6-difluorophenylamino)-7-methoxyquinazolin-6-yl)-1-((S)-3,3-dimethyl-2-((S)-2-(methylamino)propanamido)butanoyl)pyrrolidine-2-carboxamide The procedure of Example 23 was repeated except for using the compound obtained in <Step 8> instead of (1-{1-[2-(7-methoxy-4-methylaminoquinazolin-6-ylcarbamoyl)pyrrolidine-1-carbonyl]-2,2-dimethylpropylcarbamoyl}ethyl)methylcarbamic acid tert-butylester in <Step 9> to obtain the title compound (12 mg, 12%).

$^1$H NMR (300 MHz, DMSO-d6): δ 9.61 (s, 1H), 9.51 (s, 1H), 8.89 (s, 1H), 8.39 (s, 1H), 8.07 (br.d, 1H), 7.39 (m, 1H), 7.28 (s, 1H), 7.20 (t, 2H), 4.78 (m, 1H), 4.53 (d, 1H), 4.01 (s, 3H), 3.73 (m, 2H), 3.19 (m, 1H), 2.25 (s, 3H), 1.98 (m, 4H), 1.16 (d, 3H), 0.97 (s, 9H)

MS (ESI$^+$, m/z): 598 [M+H]$^+$

Example 60

Preparation of (S)-1-((S)-3,3-dimethyl-2-((S)-2-(methylamino)propanamido)butanoyl)-N-(4-(4-(4-ethylpiperazin-1-yl)phenylamino)-7-methoxyquinazolin-6-yl)pyrrolidine-2-carboxamide <Step 5> Preparation of N-(4-(4-ethylpiperazin-1-yl)phenyl)-7-fluoro-6-nitroquinazolin-4-amine The procedure of Example 23 was repeated except for using 4-(4-ethylpiperazin-1-yl)aniline instead of methylamine in <Step 5> to obtain the title compound (762 mg, 87%).

MS (ESI$^+$, m/z): 397 [M+H]$^+$

<Step 6> Preparation of N-(4-(4-ethylpiperazin-1-yl)phenyl)-7-methoxy-6-nitroquinazolin-4-amine The procedure of Example 23 was repeated except for using the compound obtained in <Step 5> instead of (7-fluoro-6-nitroquinazolin-4-yl)methylamine in <Step 6> to obtain the title compound (212 mg, 27%).

$^1$H NMR (300 MHz, DMSO-d6): δ 8.92 (s, 1H), 8.42 (s, 1H), 8.04 (br.s, 2H), 7.32 (s, 1H), 4.02 (s, 3H)

MS (ESI$^+$, m/z): 409 [M+H]$^+$

<Step 7> Preparation of N-(4-(4-ethylpiperazin-1-yl)phenyl)-7-methoxyquinazolin-4,6-diamine The procedure of Example 23 was repeated except for using the compound obtained in <Step 6> instead of 7-methoxy-6-nitroquinazolin-4-yl)methylamine in <Step 7> to obtain the title compound (148 mg, 75%).

MS (ESI$^+$, m/z): 379[M+H]$^+$

<Step 8> Preparation of tert-butyl(S)-1-((S)-1-((S)-2-(4-(4-(4-ethylpiperazin-1-yl)phenylamino)-7-methoxyquinazolin-6-ylcarbamoyl)pyrrolidin-1-yl)-3,3-dimethyl-1-oxobutan-2-ylamino)-1-oxopropan-2-yl(methyl)carbamate The procedure of Example 23 was repeated except for using the compound obtained in <Step 7> instead of 7-methoxy-N4-methylquinazolin-4,6-diamine in <Step 8> to obtain the title compound (207 mg, 69%).

MS (ESI$^+$, m/z): 775 [M+H]$^+$

<Step 9> Preparation of (S)-1-((S)-3,3-dimethyl-2-((S)-2-(methylamino)propanamido)butanoyl)-N-(4-(4-(4-ethylpiperazin-1-yl)phenylamino)-7-methoxyquinazolin-6-yl)pyrrolidine-2-carboxamide The procedure of Example 23 was repeated except for using the compound obtained in <Step 8> instead of (1-{1-[2-(7-methoxy-4-methylaminoquinazolin-6-ylcarbamoyl)pyrrolidine-1-carbonyl]-2,2-dimethylpropylcarbamoyl}ethyl)methylcarbamic acid tert-butylester in <Step 9> to obtain the title compound (43 mg, 24%).

$^1$H NMR (300 MHz, DMSO-d6): δ 9.53 (br. d, 2H), 8.81 (s, 1H), 8.38 (s, 1H), 7.86 (d, 1H), 7.49 (d, 2H), 7.21 (s, 1H), 6.92 (d, 2H), 4.75 (m, 1H), 4.52 (d, 1H), 3.98 (s, 3H), 3.72 (m, 2H), 3.11 (m, 4H), 2.98 (d, 1H), 2.48 (m, 4H), 2.35 (q, 2H), 2.18 (s, 3H), 1.96 (m, 4H), 1.11 (d, 3H), 1.02 (t, 3H), 0.96 (s, 9H)

MS (ESI$^+$, m/z): 675 [M+H]$^+$

Example 61

Preparation of (S)—N-(4-(benzo[d][1,3]dioxol-5-ylamino)-7-methoxyquinazolin-6-yl)-1-((S)-3,3-dimethyl-2-((S)-2-(methylamino)propanamido)butanoyl)pyrrolidine-2-carboxamide The procedure of Example 1 was repeated except for using 3,4-(methylenedioxy)aniline instead of 3-chloro-2,4-difluoro-aniline in <Step 4> to obtain the title compound (71 mg, 8%).

$^1$H NMR (300 MHz, MeOD): δ 8.84 (s, 1H), 8.56 (m, 2H), 8.37 (s, 1H), 8.20 (m, 3H), 7.38 (m, 3H), 7.21 (m, 2H), 7.01 (d, 1H), 6.83 (d, 1H), 5.98 (s, sH), 4.68 (s, 1H), 4.03 (s, 3H), 3.88 (m, 3H), 2.64 (s, 3H), 2.42 (m, 3H), 2.20 (m, 2H), 1.46 (d, 3H), 1.29 (m, 1H), 1.10 (s, 9H)

MS (ESI$^+$, m/z): 606 [M+H]$^+$

Example 62

Preparation of (S)-1-((S)-3,3-dimethyl-2-((S)-2-(methylamino)propanamido)butanoyl)-N-(7-methoxy-4-(quinoline-3-ylamino)quinazolin-6-yl)pyrrolidine-2-carboxamide dihydrochloride The procedure of Example 1 was repeated except for using 3-aminoquinoline instead of 3-chloro-2,4-difluoro-aniline in <Step 4> to obtain the title compound (57 mg, 7%).

$^1$H NMR (300 MHz, DMSO-d6): δ 11.75 (s, 1H), 9.92 (s, 1H), 9.39 (s, 1H), 9.21 (d, 2H), 8.91 (s, 2H), 8.62 (m, 2H), 7.84 (t, 2H), 7.69 (dt, 2H), 7.53 (s, 1H), 4.90 (m, 2H), 4.60 (d, 2H), 4.15 (s, 3H), 4.10 (m, 1H), 3.73 (m, 2H), 2.26 (m, 2H), 1.98 (m, 3H), 1.34 (d, 3H), 1.01 (s, 9H)

MS (ESI$^+$, m/z): 613 [M+H]$^+$

Example 63

Preparation of (S)-1-((S)-3,3-dimethyl-2-((S)-2-(methylamino)propanamido)butanoyl)-N-(7-methoxy-4-(quinoline-5-ylamino)quinazolin-6-yl)pyrrolidine-2-carboxamide hydrochloride The procedure of Example 1 was repeated except for using 5-aminoquinoline instead of 3-chloro-2,4-difluoro-aniline in <Step 4> to obtain the title compound (38 mg, 50%).

$^1$H NMR (300 MHz, MeOD): δ 8.92 (s, 1H), 8.44 (s, 1H), 8.22 (d, 1H), 8.05-8.02 (m, 1H), 7.74-7.70 (m, 2H), 7.37-7.32 (m, 1H), 7.18 (s, 1H), 7.07 (s, 1H), 4.90-4.89 (m, 1H), 4.66- 4.63 (m, 1H), 4.03 (s, 3H), 3.84 (s, 3H), 3.74-3.70 (m, 1H), 2.80 (s, 3H), 2.52 (br, 2H), 2.15-2.10 (m, 4H), 1.34 (d, 3H), 0.98 (s, 9H)

MS (ESI$^+$, m/z): 612 [M+H]$^+$

Example 64

Preparation of (S)-1-((S)-3,3-dimethyl-2-((S)-2-(methylamino)propanamido)butanoyl)-N-(7-methoxy-4-(4-dimethylamino)phenylamino)quinazolin-6-yl)pyrrolidine-2-carboxamide dihydrochloride The procedure of Example 1 was repeated except for using 4-dimethylaniline instead of 3-chloro-2,4-difluoro-aniline in <Step 4> to obtain the title compound (68 mg, 80%).

$^1$H NMR (300 MHz, DMSO-d$_6$): δ 11.40 (brs, 1H), 9.86 (s, 1H), 9.61 (brs, 1H), 9.11 (s, 1H), 8.94 (brs, 1H), 8.80 (s, 1H), 8.62 (d, 1H), 7.59-7.54 (m, 3H), 7.28 (brs, 2H), 4.83-4.79 (m, 1H), 4.53-4.51 (m, 1H), 4.06 (s, 3H), 4.01-3.98 (m, 1H), 3.80-3.71 (m, 2H), 3.03 (s, 6H), 2.48 (s, 3H), 2.30-1.90 (m, 4H), 1.35 (d, 3H), 1.01 (s, 9H).

MS (ESI$^+$, m/z): 604 [M+H]$^+$

Example 65

Preparation of (S)-1-((S)-3,3-dimethyl-2-((S)-2-(methylamino)propanamido)butanoyl)-N-(7-methoxy-4-(4-(pyrrolidin-1-yl)phenylamino)quinazolin-6-yl)pyrrolidine-2-carboxamide dihydrochloride The procedure of Example 1 was repeated except for using 4-(pyrrolidin-1-yl)benzenamine instead of 3-chloro-2,4-difluoro-aniline in <Step 4> to obtain the title compound (75 mg, 9%).

$^1$H NMR (300 MHz, DMSO-d6): δ 11.25 (s, 1H), 9.82 (s, 1H), 9.23 (m, 1H), 9.06 (s, 1H), 8.83 (m, 1H), 8.73 (s, 1H), 8.59 (d, 1H), 7.39 (d, 2H), 6.60 (d, 2H), 4.78 (m, 1H), 4.53 (d, 1H), 4.10 (s, 3H), 3.97 (m, 1H), 3.25 (m, 4H), 2.49 (s, 3H), 2.26 (m, 1H), 1.97 (m, 9H), 1.34 (d, 3H), 1.16 (s, 9H)

MS (ESI$^+$, m/z): 631 [M+H]$^+$

Example 66

Preparation of (S)-1-((S)-3,3-dimethyl-2-((S)-2-(methylamino)propanamido)butanoyl)-N-(7-methoxy-4-(4-(piperidin-1-yl)phenylamino)quinazolin-6-yl)pyrrolidine-2-carboxamide dihydrochloride The procedure of Example 1 was repeated except for using 4-(piperidin-1-yl)benzenamine instead of 3-chloro-2,4-difluoro-aniline in <Step 4> to obtain the title compound (5 mg, 7%).

$^1$H NMR (300 MHz, DMSO-d6): δ 11.42 (s, 1H), 9.85 (s, 1H), 9.39 (m, 1H), 8.87 (s, 1H), 8.60 (m, 1H), 8.57 (s, 1H), 8.48 (d, 1H), 7.26 (s, 1H), 4.79 (m, 1H), 4.49 (d, 1H), 4.01 (s, 3H), 3.81 (m, 12H), 3.42 (m, 5H), 2.01 (m, 9H), 1.89 (m, 3H), 1.34 (d, 3H), 0.99 (s, 9H)

MS (ESI$^+$, m/z): 645 [M+H]$^+$

Example 67

Preparation of (S)-1-((S)-3,3-dimethyl-2-((S)-2-(methylamino)propanamido)butanoyl)-N-(7-methoxy-4-(4-(4-methylpiperazin-1-yl)phenylamino)quinazolin-6-yl)pyrrolidine-2-carboxamide dihydrochloride The procedure of Example 1 was repeated except for using 4-(4-methylpiperazin-1-yl)aniline instead of 3-chloro-2,4-difluoro-aniline in <Step 4> to obtain the title compound (334 mg, 34%).

¹H NMR (300 MHz, DMSO-d6): δ 11.33 (m, 2H), 9.83 (s, 1H), 9.65 (br, 1H), 9.09 (s, 1H), 8.90 (br, 1H), 8.76 (s, 1H), 8.60 (d, 1H), 7.51-7.46 (m, 3H), 7.07 (d, 2H), 4.80-4.76 (m, 1H), 4.50 (d, 1H), 4.04 (s, 3H), 3.97-3.79 (m, 5H), 3.47 (d, 2H), 3.17-3.14 (m, 4H), 2.79 (d, 3H), 2.47-2.42 (m, 4H), 2.26-1.97 (m, 4H), 1.33 (d, 3H), 0.99 (s, 9H)

MS (ESI⁺, m/z): 660 [M+H]⁺

Example 68

Preparation of (S)-1-((S)-3,3-dimethyl-2-((S)-2-(methylamino)propanamido)butanoyl)-N-(7-methoxy-4-(4-diethylamino)phenylamino)quinazolin-6-yl)pyrrolidine-2-carboxamide dihydrochloride The procedure of Example 1 was repeated except for using 4-diethylaniline instead of 3-chloro-2,4-difluoro-aniline in <Step 4> to obtain the title compound (89 mg, 83%).

¹H NMR (300 MHz, DMSO-d₆): δ 9.70 (s, 1H), 8.94 (brs, 1H), 9.11 (s, 1H), 8.94 (brs, 1H), 8.80 (s, 1H), 8.62 (d, 1H), 7.59-7.54 (m, 3H), 7.28 (brs, 2H), 4.83-4.79 (m, 1H), 4.53-4.51 (m, 1H), 4.06 (s, 3H), 4.01-3.98 (m, 1H), 3.80-3.71 (m, 2H), 3.35 (q, 4H), 2.48 (s, 3H), 2.30-1.90 (m, 4H), 1.35 (d, 3H), 1.17 (t, 6H), 1.01 (s, 9H).

MS (ESI⁺, m/z): 632 [M+H]⁺

Example 69

Preparation of (S)—N-(4-(4-acetamidophenylamino)-7-methoxyquinazolin-6-yl)-1-((S)-3,3-dimethyl-2-((S)-2-(methylamino)propanamido)butanoyl) pyrrolidine-2-carboxamide The procedure of Example 1 was repeated except for using N-(4-amino-phenyl)-acetamide instead of 3-chloro-2,4-difluoro-aniline in <Step 4> to obtain the title compound (89 mg, 83%).

¹H NMR (300 MHz, DMSO): δ 9.91 (s, 1H), 9.64 (s, 1H), 9.57 (s, 1H), 8.85 (s, 1H), 8.41 (s, 1H), 7.62 (d, 2H), 7.54 (d, 2H), 7.24 (s, 1H), 4.78-4.74 (m, 1H), 4.53 (d, 1H), 3.81-3.71 (m, 2H), 3.29 (s, 3H), 2.98 (q, 1H), 2.18 (s, 3H), 2.13-2.97 (m, 4H), 1.23 (s, 1H), 1.09 (d, 3H), 0.96 (s, 9H).

Example 70

Preparation of (S)-1-((S)-3,3-dimethyl-2-((S)-2-(methylamino)propanamido)butanoyl)-N-(4-(4-(4-ethylpiperazin-1-yl)-3-(trifluoromethyl)phenylamino)-7-methoxyquinazolin-6-yl)pyrrolidine-2-carboxamide dihydrochloride The procedure of Example 1 was repeated except for using 4-(4-ethylpiperazin-1-yl)-3-(trifluoromethyl)aniline instead of 3-chloro-2,4-difluoro-aniline in <Step 4> to obtain the title compound (8 mg, 51%).

¹H NMR (300 MHz, DMSO): δ 9.86 (s, 1H), 9.61 (s, 1H), 8.89 (s, 1H), 8.49 (s, 1H), 8.08-8.10 (d, 1H), 8.05 (s, 1H), 7.96-7.98 (br, 1H), 7.55-7.58 (d, 1H), 7.28 (s, 1H), 4.77 (m, 1H), 4.52-4.55 (d, 1H), 4.01 (s, 3H), 3.65-4.01 (m, 2H), 3.15 (m, 1H), 2.87 (m, 4H), 2.35-2.42 (q, 2H), 2.23 (s, 3H), 1.98-2.11 (m, 8H), 1.16-1.20 (d, 3H), 1.00-1.05 (t, 3H), 0.97 (s, 9H)

MS (ESI⁺, m/z): 742.41 [M+H]⁺

Example 71

Preparation of (S)-1-((S)-3,3-dimethyl-2-((S)-2-(methylamino)propanamido)butanoyl)-N-(4-(4-(4-ethylpiperazin-1-yl)-3-fluorophenylamino)-7-methoxyquinazolin-6-yl)pyrrolidine-2-carboxamide dihydrochloride The procedure of Example 1 was repeated except for using 4-(4-ethylpiperazin-1-yl)-3-fluoroaniline instead of 3-chloro-2,4-difluoro-aniline in <Step 4> to obtain the title compound (32 mg, 55%).

¹H NMR (300 MHz, MeOD): δ 8.84 (s, 1H), 8.44 (s, 1H), 7.64 (d, 1H), 7.39 (d, 1H), 7.20 (s, 1H), 7.07 (t, 1H), 4.69 (s, 1H), 4.07 (s, 3H), 3.99-3.82 (m, 2H), 3.18-3.10 (m, 4H), 2.79-2.75 (m, 4H), 2.62 (q, 2H), 2.40 (s, 3H), 2.30-2.03 (m, 6H), 1.31 (d, 3H), 1.20 (d, 3H), 1.10 (s, 9H)

MS (ESI⁺, m/z): 692 [M+H]⁺

Example 72

Preparation of (S)—N-(4-((1,1-dioxide-4-thiomorpholinyl)phenylamino)-7-methoxyquinazolin-6-yl)-1-((S)-3,3-dimethyl-2-((S)-2-(methylamino)propanamido)butanoyl)pyrrolidine-2-carboxamide The procedure of Example 1 was repeated except for using 4-(1,1-dioxide-4-thiomorpholinyl)aniline instead of 3-chloro-2,4-difluoro-aniline in <Step 4> to obtain the title compound (2.7 mg, 25%).

¹H NMR (300 MHz, CDCl₃): δ 9.67 (s, 1H), 9.55 (br, 1H), 9.14 (s, 1H), 8.92 (br, 1H), 7.63 (d, 2H), 7.53 (s, 1H), 6.98 (d, 2H) 4.84-4.80 (m, 1H), 4.50 (d, 1H), 4.11 (s, 3H), 3.92 (m, 7H), 3.85 (m, 2H), 3.67 (m, 2H), 3.16 (m, 2H), 2.03-1.95 (m, 4H), 1.30 (d, 3H), 0.98 (s, 9H)

MS (ESI⁺, m/z): 695 [M+H]⁺

Example 73

Preparation of (S)-1-((S)-3,3-dimethyl-2-((S)-2-(methylamino)propanamido)butanoyl)-N-(7-methoxy-4-(pyridin-4-ylamino)quinazolin-6-yl)pyrrolidine-2-carboxamide hydrochloride The procedure of Example 1 was repeated except for using 4-aminopyridine instead of 3-chloro-2,4-difluoro-aniline in <Step 4> to obtain the title compound (3 mg, 15%).

¹H NMR (300 MHz, MeOD): δ 9.80 (s, 1H), 8.72 (s, 1H), 8.51 (d, 1H), 7.90 (d, 1H), 7.28 (s, 1H), 4.89 (m, 1H), 4.67-4.64 (m, 1H), 4.04 (s, 3H), 3.99-3.96 (m, 2H), 2.80 (s, 3H), 2.50 (m, 1H), 2.09-2.02 (m, 4H), 1.34 (d, 3H), 0.98 (s, 9H).

MS (ESI⁺, m/z): 563 [M+H]⁺

Example 74

Preparation of (S)-1-((S)-3,3-dimethyl-2-((S)-2-(methylamino)propanamido)butanoyl)-N-(7-methoxy-4-(4-(methylcarbamoyl)phenylamino)quinazolin-6-yl) pyrrolidine-2-carboxamide The procedure of Example 1 was repeated except for using 4-amino-N-methyl-benzamide instead of 3-chloro-2,4-difluoro-aniline in <Step 4> to obtain the title compound (44 mg, 43%).

¹H NMR (300 MHz, MeOD): δ 8.87 (s, 1H), 8.52 (s, 1H), 7.95-7.81 (m, 4H), 7.22 (s, 1H), 4.79 (s, 1H), 4.69 (s, 1H), 4.06 (s, 3H), 3.93-3.87 (m, 2H), 3.71-3.67 (m, 1H), 2.55 (s, 3H), 2.33-1.83 (m, 4H), 1.35 (d, 3H), 1.03 (s, 9H)
MS (ESI⁺, m/z): 619 [M+H]⁺

Example 75

Preparation of (S)—N-(4-(5-acetamino-2-chlorophenylamino)-7-methoxyquinazolin-6-yl)-1-((S)-3,3-dimethyl-2-((S)-2-(methylamino)propanamido)butanoyl)pyrrolidine-2-carboxamide <Step 4> Preparation of 7-methoxy-6-nitroquinazolin-4(3H)-one 7-fluoro-6-nitroquinazolin-4(3H)-one (60 g, 287 mmol) in <Step 3> of Example 3 was dissolved in DMSO (600 mL) and sodium methoxide (46.5 g, 861 mmol) was added dropwise thereto in an ice water bath. Thirty minutes later, KOTMS (147 g, 1150 mmol) was added slowly to the water bath, and the mixture was subjected to a reaction for one day. Then, the mixture was neutralized with a 2N HCl solution. Subsequently, the solid thus obtained was filtered and dried to obtain the title compound (48 g, 76%).

¹H NMR (300 MHz, DMSO-d6): δ 8.51 (s, 1H), 8.22 (s, 1H), 7.41 (s, 1H), 4.03 (s, 3H)
MS (ESI⁺, m/z): 222 [M+H]⁺

<Step 5> Preparation of 4-chloro-7-methoxy-6-nitroquinazoline

The procedure of Example 1 was repeated except for using the compound obtained in <Step 4> instead of 7-fluoro-6-nitroquinazolin-4(3H)-one in <Step 4> to obtain the title compound (332 mg, 61%).

¹H NMR (300 MHz, DMSO-d6): δ 9.14 (s, 1H), 8.81 (s, 1H), 7.81 (s, 1H), 4.12 (s, 3H)
MS (ESI⁺, m/z): 240 [M+H]⁺

<Step 6> Preparation of N-(4-chloro-3-(7-methoxy-6-nitroquinazolin-4-ylamino)phenyl)acetamide The procedure of Example 23 was repeated except for using the compound obtained in <Step 5> instead of 4-chloro-7-fluoro-6-nitroquinazoline in <Step 5> and N-(3-amino-4-chlorophenyl)acetamide instead of methylamine to obtain the title compound (455 mg, 98%).

¹H NMR (300 MHz, DMSO-d6): δ 10.3 (s, 1H), 9.43 (s, 1H), 8.80 (s, 1H), 7.91 (br. s, 1H), 7.58 (s, 1H), 7.54 (s, 2H), 4.10 (s, 3H), 2.06 (s, 3H)
MS (ESI⁺, m/z): 389 [M+H]⁺

<Step 7> Preparation of N-(3-(6-amino-7-methoxyquinazolin-4-ylamino)-4-chlorophenyl)acetamide The procedure of Example 23 was repeated except for using the compound obtained in <Step 6> instead of 7-methoxy-6-nitroquinazolin-4-yl)methylamine in <Step 7> to obtain the title compound (42 mg, 10%).

¹H NMR (300 MHz, DMSO-d6): δ 10.1 (s, 1H), 9.01 (s, 1H), 8.20 (s, 1H), 7.94 (d, 1H), 7.46 (d, 1H), 7.43 (s, 1H), 7.29 (s, 1H), 7.07 (s, 1H), 5.36 (br.s, 2H), 3.95 (s, 3H), 2.04 (s, 3H)
MS (ESI⁺, m/z): 359 [M+H]⁺

<Step 8> Preparation of tert-butyl(S)-1-((S)-1-((S)-2-(4-(5-acetamido-2-chlorophenylamino)-7-methoxyquinazolin-6-ylcarbamoyl)pyrrolidin-1-yl)-3,3-dimethyl-1-oxobutan-2-ylamino)-1-oxopropan-2-yl(methyl)carbamate The procedure of Example 23 was repeated except for using the compound obtained in <Step 7> instead of 7-methoxy-N4-methylquinazolin-4,6-diamine in <Step 8> to obtain the title compound (74 mg, 86%).
MS (ESI⁺, m/z): 754 [M+H]⁺

<Step 9> Preparation of (S)—N-(4-(5-acetamino-2-chlorophenylamino)-7-methoxyquinazolin-6-yl)-1-((S)-3,3-dimethyl-2-((S)-2-(methylamino)propanamido)butanoyl)pyrrolidine-2-carboxamide The procedure of Example 23 was repeated except for using the compound obtained in <Step 8> instead of (1-{1-[2-(7-methoxy-4-methylaminoquinazolin-6-ylcarbamoyl)pyrrolidine-1-carbonyl]-2,2-dimethylpropylcarbamoyl}ethyl)methylcarbamic acid tert-butylester in <Step 9> to obtain the title compound (5 mg, 7%).

¹H NMR (300 MHz, DMSO-d6): 10.1 (s, 1H), 9.68 (s, 1H), 9.60 (s, 1H), 8.89 (s, 1H), 8.34 (s, 1H), 7.96 (d, 1H), 7.83 (s, 1H), 7.45 (m, 2H), 7.26 (s, 1H), 4.77 (m, 1H), 4.53 (d, 1H), 4.01 (s, 3H), 3.74 (m, 2H), 3.04 (m, 1H), 2.20 (s, 3H), 2.04 (s, 3H), 1.90 (m, 4H), 1.12 (d, 3H), 0.97 (s, 9H)
MS (ESI⁺, m/z): 654 [M+H]⁺

Example 76

Preparation of (S)—N-(4-(4-benzamidophenylamino)-7-methoxyquinazolin-6-yl)-1-((S)-3,3-dimethyl-2-((S)-2-(methylamino)propanamido)butanoyl)pyrrolidine-2-carboxamide The procedure of Example 1 was repeated except for using N-(4-amino-phenyl)-benzamide instead of 3-chloro-2,4-difluoro-aniline in <Step 4> to obtain the title compound (10 mg, 19%).

¹H NMR (300 MHz, CDCl₃): δ 9.62 (br, 1H), 8.88 (br, 1H), 8.59 (s, 1H), 8.05 (s, 1H), 7.89-7.87 (m, 2H), 7.73-7.64 (m, 4H), 7.54-7.45 (m, 3H), 7.18 (s, 1H), 4.86-4.84 (m, 1H), 4.63 (d, 1H), 3.96 (s, 3H), 3.72 (m, 2H), 3.09 (q, 1H), 2.41 (s, 3H), 2.10-1.95 (m, 4H), 1.33 (d, 3H), 1.03 (s, 9H).

Example 77

Preparation of (S)—N-(4-(cyclohexylmethyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using cyclohexylmethanamine instead of 3-chloro-2,4-difluoro-aniline in <Step 4> to obtain the title compound (530 mg, 4%).

¹H NMR (300 MHz, CDCl3): δ 9.59 (s, 1H), 8.79 (s, 1H), 8.52 (s, 1H), 7.88 (d, 1H), 6.97 (s, 1H), 5.78 (m, 1H), 4.85 (m, 1H), 4.61 (d, 1H), 3.99 (s, 3H), 3.70 (m, 2H), 3.09 (m, 1H), 2.41 (s, 3H), 2.11-1.98 (m, 4H), 1.75 (m, 6H), 1.33 (d, 3H), 1.19 (m, 5H), 1.03 (s, 9H).
MS (ESI⁺, m/z): 582 [M+H]⁺

Example 78

Preparation of (S)—N-(4-((2-chloropyridin-3-yl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2-chloropyridin-3-amine instead of 3-chloro-2,4-difluoro-aniline in <Step 4> to obtain the title compound (20 mg, 0.3%).

¹H NMR (300 MHz, DMSO-d6): δ 9.86 (s, 1H), 9.14 (s, 1H), 8.79 (s, 1H), 8.58 (d, 1H), 8.45 (m, 1H), 8.03 (m, 1H), 7.61 (m, 1H), 7.43 (s, 1H), 4.81 (m, 3H), 4.52 (d, 1H), 4.08 (s,

3H), 3.95 (m, 2H), 2.49 (s, 3H), 2.47 (m, 1H), 2.14-1.89 (m, 4H), 1.33 (d, 3H), 1.00 (s, 9H).
MS (ESI$^+$, m/z): 597 [M+H]$^+$

Example 79

Preparation of (S)—N-(4-((6-chloropyridin-3-yl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 6-chloropyridin-3-amine instead of 3-chloro-2,4-difluoro-aniline in <Step 4> to obtain the title compound (45 mg, 8%).
$^1$H NMR (300 MHz, CDCl3): δ 9.84 (s, 1H), 9.19 (s, 1H), 8.76 (s, 1H), 8.60 (d, 1H), 8.51 (m, 1H), 7.99 (s, 1H), 7.74 (s, 1H), 7.39 (d, 1H), 4.85 (m, 3H), 4.52 (d, 1H), 4.11 (s, 3H), 3.95 (m, 2H), 2.49 (s, 3H), 2.39 (m, 1H), 2.13 (m, 4H), 1.29 (d, 3H), 1.02 (s, 9H).
MS (ESI$^+$, m/z): 597 [M+H]$^+$ Example 80

Preparation of (S)—N-(4-((4-bromo-2-chlorophenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 4-bromo-2-chloroaniline instead of 3-chloro-2,4-difluoro-aniline in <Step 4> to obtain the title compound (112 mg, 5%).
$^1$H NMR (300 MHz, DMSO-d6): δ 9.88 (s, 1H), 8.79 (s, 1H), 8.61 (d, 1H), 7.95 (d, 1H), 7.70 (d, 1H), 7.51 (s, 1H), 7.50 (d, 1H), 4.81 (m, 1H), 4.51 (d, 1H), 4.07 (s, 3H), 3.95 (m, 1H), 3.77-3.71 (m, 2H), 2.45 (d, 3H), 2.01-1.89 (m, 4H), 1.34 (d, 3H), 1.00 (s, 9H).
MS (ESI$^+$, m/z): 674 [M+H]$^+$ Example 81

Preparation of (S)—N-(4-((2,3-dichlorophenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2,3-dichloroaniline instead of 3-chloro-2,4-difluoro-aniline in <Step 4> to obtain the title compound (65 mg, 5%).
$^1$H NMR (300 MHz, DMSO-d6): δ 9.88 (s, 1H), 9.14 (s, 1H), 8.79 (s, 1H), 8.60 (d, 1H), 7.71 (d, 1H), 7.52 (m, 1H), 4.81 (m, 1H), 4.52 (d, 1H), 3.95 (m, 3H), 3.71 (m, 2H), 2.47 (d, 3H), 2.14-1.89 (m, 4H), 1.33 (d, 3H), 1.00 (s, 9H).
MS (ESI$^+$, m/z): 630 [M+H]$^+$ Example 82

Preparation of (S)—N-(4-((2-bromo-4-fluorophenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2-bromo-4-fluoroaniline instead of 3-chloro-2,4-difluoro-aniline in <Step 4> to obtain the title compound (92 mg, 3%).
$^1$H NMR (300 MHz, DMSO-d6): δ 9.87 (s, 1H), 9.13 (s, 1H), 8.78 (s, 1H), 8.60 (d, 1H), 7.79 (dd, 1H), 7.57 (dd, 1H), 7.45-7.39 (m, 2H), 4.80 (m, 1H), 4.52 (d, 1H), 4.07 (s, 3H), 3.94 (m, 1H), 3.69 (m, 2H), 2.48 (d, 3H), 2.13-1.79 (m, 4H), 1.33 (d, 3H), 1.00 (s, 9H).
MS (ESI$^+$, m/z): 658 [M+H]$^+$ Example 83

Preparation of (S)-1-((S)-3,3-dimethyl-2-((S)-2-(methylamino)propanamido)butanoyl)-N-(7-methoxy-4-(phenylamino)quinazolin-6-yl)pyrrolidine-2-carboxamide hydrochloride The procedure of Example 1 was repeated except for using 2-phenylethanamine instead of 3-chloro-2,4-difluoro-aniline in <Step 4> to obtain the title compound (138 mg, 3%).
$^1$H NMR (300 MHz, DMSO-d6): δ 9.98 (br, 1H), 9.77 (s, 1H), 9.37 (br, 1H), 8.87 (s, 2H), 8.80 (s, 1H), 8.59 (d, 1H), 7.36 (s, 1H), 7.24 (m, 5H), 4.78 (m, 1H), 4.51 (d, 1H), 4.02 (s, 3H), 3.38 (m, 2H), 2.97 (t, 2H), 2.48 (t, 2H), 2.01 (m, 4H), 1.33 (d, 3H), 1.00 (s, 9H).
MS (ESI$^+$, m/z): 590 [M+H]$^+$ Example 84

Preparation of (S)-1-((S)-3,3-dimethyl-2-((S)-2-(methylamino)propanamido)butanoyl)-N-(7-methoxy-4-((6-(prop-2-yn-1-yloxy)pyridin-3-yl)amino)quinazolin-6-yl)pyrrolidine-2-carboxamide hydrochloride The procedure of Example 1 was repeated except for using 6-(prop-2-yn-1-yloxy)pyridin-3-amine instead of 3-chloro-2,4-difluoro-aniline in <Step 4> to obtain the title compound (71.6 mg, 60%).
$^1$H NMR (300 MHz, DMSO): δ 9.81 (brs, 1H), 9.05 (s, 1H), 8.80 (s, 1H), 8.60-8.57 (d, 1H), 8.03-8.02 (d, 1H), 7.70-7.67 (dd, 1H), 7.38 (s, 1H), 6.55-6.53 (d, 1H), 4.83 (m, 1H), 4.78-4.77 (m, 2H), 4.55-4.52 (d, 1H), 4.07 (s, 3H), 3.78-3.71 (m, 2H), 3.48 (m, 1H), 2.50 (s, 3H), 2.03-1.91 (m, 4H), 1.36-1.33 (d, 3H), 1.01 (s, 9H)

Example 85

Preparation of (S)-1-((S)-3,3-dimethyl-2-((S)-2-(methylamino)propanamido)butanoyl)-N-(4-((3-fluoro-4-(piperidin-1-yl)phenyl)amino)-7-methoxyquinazolin-6-yl)pyrrolidine-2-carboxamide hydrochloride The procedure of Example 1 was repeated except for using 3-fluoro-4-(piperidin-1-yl)aniline instead of 3-chloro-2,4-difluoro-aniline in <Step 4> to obtain the title compound (197 mg, 83%).
$^1$H NMR (300 MHz, DMSO): δ 11.33 (s, 1H), 9.86 (s, 1H), 9.10 (s, 1H), 8.85 (s, 1H), 8.61-8.58 (d, 1H), 7.53-7.48 (d, 1H), 7.41 (s, 1H), 7.36-7.33 (d, 1H), 7.16-7.09 (t, 1H), 4.80 (m, 1H), 4.54-4.51 (d, 1H), 4.13 (s, 3H), 3.96 (m, 2H), 3.02-2.99 (m, 4H), 2.02 (m, 1H), 1.91 (m, 4H), 1.67 (m, 4H), 1.54 (m, 2H), 1.35-1.33 (d, 3H), 1.00 (s, 9H)

Example 86

Preparation of (S)—N-(4-((3-chloro-4-(4-methylpiperazin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 3-chloro-4-(4-methylpiperazin-1-yl)aniline instead of 3-chloro-2,4-difluoro-aniline in <Step 4> to obtain the title compound (130 mg, 74%).

¹H NMR (300 MHz, DMSO): δ10.83 (brs, 1H), 9.83 (s, 1H), 9.30 (brs, 1H), 9.25 (s, 1H), 8.81 (s, 1H), 8.62-8.60 (d, 1H), 7.83 (d, 1H), 7.62-7.59 (d, 1H), 7.44 (s, 1H), 7.32-7.29 (d, 1H), 4.81-4.80 (m, 1H), 4.54-4.51 (d, 1H), 4.01 (s, 3H), 3.80 (m, 1H), 3.47-3.34 (m, 4H), 3.23-3.15 (m, 4H), 2.85-2.84 (m, 3H), 2.50 (s, 3H), 2.04-1.99 (m, 2H), 1.91 (m, 4H), 1.35-1.33 (d, 3H), 0.95 (s, 9H)

MS (ESI⁺, m/z): 694 [M+H]⁺

Example 87

Preparation of (S)—N-(4-((4-bromo-3-chloro-2-fluorophenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 4-bromo-3-chloro-2-fluoroaniline instead of 3-chloro-2,4-difluoro-aniline in <Step 4> to obtain the title compound (1 g, 68%).

¹H NMR (300 MHz, CDCl₃): δ 9.73 (brs, 1H), 9.08 (s, 1H), 8.68 (s, 1H), 8.37-8.32 (t, 1H), 7.91-7.88 (d, 1H), 7.50 (brs, 1H), 7.48-7.45 (dd, 1H), 4.89-4.86 (dd, 1H), 4.65-4.61 (d, 1H), 4.05 (s, 3H), 3.99-3.96 (q, 1H), 3.75-3.70 (m, 1H), 3.14-3.07 (q, 1H), 2.59-2.54 (m, 1H), 2.43 (s, 3H), 2.20-1.97 (m, 4H), 1.35-1.33 (d, 3H), 1.05 (s, 9H)

Example 88

Preparation of (S)—N-(4-((4-(1H-imidazol-1-yl)phenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 4-(1H-imidazol-1-yl)aniline instead of 3-chloro-2,4-difluoro-aniline in <Step 4> to obtain the title compound (13 mg, 23%).

MS (ESI⁺, m/z): 628 [M+H]⁺

Example 89

Preparation of (S)-1-((S)-3,3-dimethyl-2-((S)-2-(methylamino)propanamido)butanoyl)-N-(4-(3-(2-fluorophenyl)ureido)-7-methoxyquinazolin-6-yl)pyrrolidine-2-carboxamide hydrochloride The procedure of Example 1 was repeated except for using 1-(2-fluorophenyl)urea instead of 3-chloro-2,4-difluoro-aniline in <Step 4> to obtain the title compound (42 mg, 41%).

¹H NMR (300 MHz, DMSO): δ 9.74 (brs, 1H), 9.40 (brs, 1H), 9.14 (s, 1H), 8.84 (s, 1H), 8.63-8.60 (d, 1H), 8.20-8.17 (t, 1H), 7.46 (s, 1H), 7.37-7.14 (m, 3H), 4.78 (m, 1H), 4.55-4.53 (d, 1H), 4.04 (s, 3H), 3.34 (m, 2H), 2.50 (s, 3H), 2.47 (m, 1H), 2.05 (m, 4H), 1.34-1.32 (d, 3H), 1.02 (s, 9H)

Example 90

Preparation of (S)-1-((S)-3,3-dimethyl-((S)-2-(methylamino)propanamido)butanoyl)-N-(7-methoxy-4-((4-morpholinophenyl)amino)quinazolin-6-yl)pyrrolidine-2-carboxamide hydrochloride The procedure of Example 1 was repeated except for using 4-morpholinoaniline instead of 3-chloro-2,4-difluoro-aniline in <Step 4> to obtain the title compound (45 mg, 1%).

¹H NMR (300 MHz, DMSO-d6): δ 9.64 (s, 1H), 8.94 (br, 1H), 8.56 (s, 1H), 7.85 (d, 1H), 7.53 (m, 3H), 7.25 (s, 1H), 6.64 (d, 2H), 4.86 (m, 1H), 4.62 (d, 1H), 3.99 (s, 3H), 3.95 (m, 1H), 3.86 (m, 4H), 3.69 (m, 2H), 3.14 (m, 4H), 2.41 (s, 3H), 2.03 (m, 4H), 1.32 (d, 3H), 1.02 (s, 9H).

MS (ESI⁺, m/z): 647 [M+H]⁺

Example 91

Preparation of (S)-1-((S)-3,3-dimethyl-2-((S)-2-(methylamino)propanamide)butanoyl)-N-(7-methoxy-4-((4-(2-propyn-1-yloxy)phenyl)amino)quinazolin-6-yl)pyrrolidine-2-carboxamide hydrochloride The procedure of Example 1 was repeated except for using 4-(2-propyn-1-yloxy)aniline instead of 3-chloro-2,4-difluoro-aniline in <Step 4> to obtain the title compound (20 mg, 25%).

¹H NMR (300 MHz, DMSO-d6): δ 11.28 (brs, 1H), 9.83 (s, 1H), 9.46 (brs, 1H), 9.12 (s, 1H), 8.91 (brs, 1H), 8.80 (brs, 1H), 8.60 (d, J=8.1 Hz, 1H), 7.53 (d, J=9.0 Hz, 2H), 7.09 (d, J=9.0 Hz, 2H), 5.04 (s, 2H), 4.81-4.73 (m, 1H), 4.53-4.50 (m, 1H), 4.06 (s, 3H), 3.99-3.63 (m, 3H), 2.46 (s, 3H), 2.17-1.91 (m, 4H), 1.35 (d, J=6.6 Hz, 3H), 1.00 (s, 9H).

MS (ESI⁺, m/z): 616 [M+H]⁺

Example 92

Preparation of (S)—N-(4-((3-chloro-4-(4-(cyclopropylmethyl)piperazin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide The procedure of Example 1 was repeated except for using 3-chloro-4-(4-(cyclopropylmethyl)piperazin-1-yl)aniline instead of 3-chloro-2,4-difluoro-aniline in <Step 4> to obtain the title compound (106 mg, 3.8%).

¹H NMR (300 MHz, CDCl₃): δ 9.50 (s, 1H), 8.75 (s, 1H), 8.46 (s, 1H), 7.73 (d, 1H), 7.68-7.63 (m, 2H), 7.41 (dd, 1H), 7.05 (s, 1H), 6.93 (d, 1H), 4.71 (dd, 1H), 4.47 (d, 1H), 3.88-3.79 (m, 4H), 3.60-3.58 (m, 1H), 2.97-2.91 (m, 5H), 2.61 (m, 4H), 2.26 (s, 3H), 2.22 (d, 3H), 2.03-1.85 (m, 9H), 1.18 (d, 3H), 0.89-0.79 (m. 10H), 0.39 (q, 2H), 0.02 (q, 2H).

MS (ESI⁺, m/z): 735 [M+H]⁺

Example 93

Preparation of (S)-1-((S)-3,3-dimethyl-2-((S)-2-(methylamino)propanamide)butanoyl)-N-(7-methoxy-4-((2-methyl-4-oxo-4H-chromen-7-yl)amino)quinazolin-6-yl)pyrrolidine-2-carboxamide hydrochloride The procedure of Example 1 was repeated except for using 7-amino-2-methyl-4H-chromen-4-one instead of 3-chloro-2,4-difluoro-aniline in <Step 4> to obtain the title compound (18 mg, 12%).

MS (ESI⁺, m/z): 644 [M+H]⁺

Example 94

Preparation of (S)-1-((S)-3,3-dimethyl-2-((S)-2-(methylamino)propanamide)butanoyl)-N-(7-methoxy-4-((2-oxoindolin-5-yl)amino)quinazolin-6-yl)pyrrolidine-2-carboxamide hydrochloride The procedure of Example 1 was repeated except for using 5-aminoindolin-2-one instead of 3-chloro-2,4-difluoro-aniline in <Step 4> to obtain the title compound (20 mg, 15%).

MS (ESI⁺, m/z): 617 [M+H]⁺

Example 95

Preparation of (S)—N-(4-((3-chloro-4-morpholinophenyl)amino)-7-methoxyquinazolin-6-yl)-1-((S)-3,3-dimethyl-2-((S)-2-(methylamino)propanamido)butanoyl)pyrrolidine-2-carboxamide The procedure of Example 1 was repeated except for using 3-chloro-4-morpholinoaniline instead of 3-chloro-2,4-difluoro-aniline in <Step 4> to obtain the title compound (85 mg, 3.4%).
MS (ESI$^+$, m/z): 682 [M+H]$^+$

Example 96

Preparation of (S)—N-(4-((3-chloro-4-(piperidin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 3-chloro-4-(piperidin-1-yl)aniline instead of 3-chloro-2,4-difluoro-aniline in <Step 4> to obtain the title compound (48 mg, 8%).
MS (ESI$^+$, m/z): 679 [M+H]$^+$

Example 97

Preparation of (S)—N-(4-((3-chloro-4-(4-isopropylpiperazin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 3-chloro-4-(4-isopropylpiperazin-1-yl)aniline instead of 3-chloro-2,4-difluoro-aniline in <Step 4> to obtain the title compound (15 mg, 6%).
MS (ESI$^+$, m/z): 722 [M+H]$^+$

Example 98

Preparation of (S)—N-(4-((3-chloro-4-(4-propyl-1-yl)phenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 3-chloro-4-(4-propylpiperazin-1-yl)aniline instead of 3-chloro-2,4-difluoro-aniline in <Step 4> to obtain the title compound (15 mg, 6%).
MS (ESI$^+$, m/z): 722 [M+H]$^+$

Example 99

Preparation of (S)—N-(4-((3-chloro-4-(diethylamino)phenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 2-chloro-N'N'-diethylbenzene-1,4-diamine instead of 3-chloro-2,4-difluoro-aniline in <Step 4> to obtain the title compound (14 mg, 6%).
MS (ESI$^+$, m/z): 667 [M+H]$^+$

Example 100

Preparation of (S)—N-(4-((4-(4-(cyclopropylmethyl)piperazin-1-yl)-3-fluorophenyl)amino)-7-methoxyquinazolin-6-yl)-1-((S)-3,3-dimethyl-2-((S)-2-(methylamino)propanamido)butanoyl)pyrrolizine-2-carboxamide hydrochloride The procedure of Example 1 was repeated except for using 4-(4-(cyclopropylmethyl)piperazin-1-yl)-3-fluoroaniline instead of 3-chloro-2,4-difluoro-aniline in <Step 4> to obtain the title compound (40 mg, 7%).
$^1$H NMR (300 MHz, DMSO): δ 9.69 (s, 1H), 9.60 (s, 1H), 8.85 (s, 1H), 8.46 (s, 1H), 7.88-7.91 (d, 1H), 7.66-7.71 (dd, 1H), 7.45-7.48 (d, 1H), 7.06 (s, 1H), 6.99-7.06 (t, 1H), 4.75-4.78 (m, 1H), 4.52-4.55 (d, 1H), 4.00 (s, 3H), 3.71-3.77 (m, 2H), 3.01 (m, 4H), 2.60 (m, 4H), 2.23-2.25 (d, 2H), 2.19 (s, 3H), 1.94-2.17 (m, 4H), 1.12-1.14 (d, 3H), 0.97 (s, 9H), 0.83-0.85 (m, 1H), 0.47-0.49 (m, 2H), 0.02-0.11 (m, 2H)
MS (ESI$^+$, m/z): 718 [M+H]$^+$

Example 101

Preparation of (S)—N-(4-((3,5-dichloro-4-(pyridin-2-ylmethoxy)phenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 3,5-dichloro-4-(pyridin-2-ylmethoxy)aniline instead of 3-chloro-2,4-difluoro-aniline in <Step 4> to obtain the title compound (147 mg, 7%).
$^1$H NMR (300 MHz, DMSO): δ 9.87 (s, 1H), 9.65 (s, 1H), 8.89 (s, 1H), 8.58 (s, 2H), 8.04 (s, 2H), 7.85-7.94 (m, 2H), 7.71-7.74 (d, 1H), 7.38-7.42 (m, 1H), 7.31 (s, 1H), 5.10) s, 2H), 4.47-4.80 (m, 1H), 4.52-4.56 (d, 1H), 4.02 (s, 3H), 3.72-3.79 (m, 2H), 2.18 (s, 3H), 1.93-2.08 (m, 4H), 1.11-1.13 (d, 3H), 0.97 (s, 9H)
MS (ESI$^+$, m/z): 737 [M+H]$^+$

Example 102

Preparation of (S)—N-(4-((3-chloro-4-(pyridin-2-ylmethoxy)phenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 3-chloro-4-(pyridin-2-ylmethoxy)aniline instead of 3-chloro-2,4-difluoro-aniline in <Step 4> to obtain the title compound (226 mg, 7%).
$^1$H NMR (300 MHz, DMSO): δ 9.71 (s, 1H), 9.61 (s, 1H), 8.86 (s, 1H), 8.70-8.71 (d, 1H), 8.56-8.58 (dd, 1H), 8.47 (s, 1H), 7.86-7.92 (m, 3H), 7.65-7.69 (dd, 1H), 7.44-7.48 (m, 1H), 7.26-7.30 (m, 2H), 5.27 (s, 2H), 4.76-4.79 (m, 1H), 4.52-4.56 (d, 1H), 4.01 (s, 3H), 3.70-3.78 (m, 2H), 5.27 (s, 2H), 4.76-4.79 (m, 1H), 4.52-4.56 (d, 1H), 4.01 (s, 3H), 3.70-3.78 (m, 2H), 2.15 (s, 3H), 1.91-2.09 (m, 4H), 1.12-1.19 (d, 3H), 0.97 (s, 9H)
MS (ESI$^+$, m/z): 703 [M+H]$^+$

Example 103

Preparation of (S)—N-(4-((4-([1,4'-bipiperidine]-1'-yl)phenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 4-([1,4'-bipiperidine]-1'-yl)aniline instead of 3-chloro-2,4-difluoro-aniline in <Step 4> to obtain the title compound (23 mg, 5%).

MS (ESI$^+$, m/z): 728 [M+H]$^+$

Example 104

Preparation of (S)-1-((S)-3,3-dimethyl-2-((S)-2-(methylamino)propanamido)butanoyl)-N-(7-methoxy-4-((4-(piperidin-1-ylmethyl)phenyl)amino)quinazolin-6-yl)pyrrolidine-2-carboxamide hydrochloride The procedure of Example 1 was repeated except for using 4-(piperidin-1-ylmethyl)aniline instead of 3-chloro-2,4-difluoro-aniline in <Step 4> to obtain the title compound (30 mg, 6%).

$^1$H NMR (300 MHz, DMSO): δ 9.67 (s, 1H), 9.58 (s, 1H), 8.87 (s, 1H), 8.45 (s, 1H), 7.85-7.88 (d, 1H), 7.65-7.68 (d, 2H), 7.23-7.26 (m, 4H), 4.79 (m, 1H), 4.55-4.74 (d, 1H), 4.00 (s, 3H), 3.71-3.77 (m, 2H), 3.39 (s, 2H), 2.98-3.00 (m, 1H), 2.34 (br, s, 4H), 2.19 (s, 3H), 1.98-2.08 (m, 4H), 1.47-1.49 (br, 4H)

MS (ESI$^+$, m/z): 659 [M+H]$^+$

Example 105

Preparation of (S)-1-((S)-3,3-dimethyl-2-((S)-2-(methylamino)propanamido)butanoyl)-N-(7-methoxy-4-((4-(4-(4-methylpiperazin-1-yl)piperidin-1-yl)phenyl)amino)quinazolin-6-yl)pyrrolidine-2-carboxamide hydrochloride The procedure of Example 1 was repeated except for using 3,5-dichloro-4-(pyridin-2-ylmethoxy)aniline instead of 3-chloro-2,4-difluoro-aniline in <Step 4> to obtain the title compound (20 mg, 7%).

$^1$H NMR (300 MHz, DMSO): δ 9.52-9.54 (d, 2H), 8.81 (s, 1H), 8.39 (s, 1H), 7.89-7.92 (d, 1H), 7.49-7.52 (d, 2H), 7.22 (s, 1H), 6.91-6.94 (d, 2H), 4.76-4.78 (m, 1H), 4.52-4.55 (d, 1H), 3.66-3.77 (m, 4H), 3.32 (s, 3H), 3.02-3.05 (q, 1H), 2.18 (s, 3H), 2.14 (s, 3H), 2.02-2.11 (m, 4H), 1.82-1.86 (m, 2H), 1.51 (m, 2H), 1.12-1.14 (d, 3H), 0.97 (s, 9H)

MS (ESI$^+$, m/z): 743 [M+H]$^+$

Example 106

Preparation of (S)-1-((S)-3,3-dimethyl-2-((S)-2-(methylamino)propanamido)butanoyl)-N-(7-methoxy-4-((4-(1-methylpiperidin-4-yl)phenyl)amino)quinazolin-6-yl)pyrrolidine-2-carboxamide hydrochloride The procedure of Example 1 was repeated except for using 4-(1-methylpiperidin-4-yl)aniline instead of 3-chloro-2,4-difluoro-aniline in <Step 4> to obtain the title compound (32 mg, 7%).

MS (ESI$^+$, m/z): 659 [M+H]$^+$

Example 107

Preparation of (S)-1-((S)-3,3-dimethyl-2-((S)-2-(methylamino)propanamido)butanoyl)-N-(7-methoxy-4-((4-(4-methylpiperidin-1-yl)cyclohexyl)amino)quinazolin-6-yl)pyrrolidine-2-carboxamide hydrochloride The procedure of Example 1 was repeated except for using 4-(4-methylpiperidin-1-yl)cyclohexanamine instead of 3-chloro-2,4-difluoro-aniline in <Step 4> to obtain the title compound (16 mg, 5%).

MS (ESI$^+$, m/z): 665 [M+H]$^+$

Example 108

Preparation of (S)-1-((S)-3,3-dimethyl-2-((S)-2-(methylamino)propanamido)butanoyl)-N-(7-methoxy-4-((4-((4-methylpiperazin-1-yl)sulfonyl)phenyl)amino)quinazolin-6-yl)pyrrolidine-2-carboxamide hydrochloride The procedure of Example 1 was repeated except for using 4-((4-methylpiperazin-1-yl)sulfonyl)aniline instead of 3-chloro-2,4-difluoro-aniline in <Step 4> to obtain the title compound (34 mg, 8%).

MS (ESI$^+$, m/z): 724 [M+H]$^+$

Example 109

Preparation of (2S)-1-((S)-3,3-dimethyl-2-((S)-2-(methylamino)propanamido)butanoyl)-N-(7-methoxy-4-((4-(1-methylpiperidin-3-yl)phenyl)amino)quinazolin-6-yl)pyrrolidine-2-carboxamide hydrochloride The procedure of Example 1 was repeated except for using 4-(1-methylpiperidin-3-yl)aniline instead of 3-chloro-2,4-difluoro-aniline in <Step 4> to obtain the title compound (18 mg, 3%).

MS (ESI$^+$, m/z): 659 [M+H]$^+$

Example 110

Preparation of (S)-1-((S)-3,3-dimethyl-2-((S)-2-(methylamino)propanamido)butanoyl)-N-(7-methoxy-4-((4-(4-(1-methylpiperidin-4-yl)piperazin-1-yl)phenyl)amino)quinazolin-6-yl)pyrrolizine-2-carboxamide hydrochloride The procedure of Example 1 was repeated except for using 4-(4-(1-methylpiperidin-4-yl)piperazin-1-yl)aniline instead of 3-chloro-2,4-difluoro-aniline in <Step 4> to obtain the title compound (62 mg, 9%).

MS (ESI$^+$, m/z): 743 [M+H]$^+$

Example 111

Preparation of (S)—N-(4-((4-((1H-imidazol-1-yl)methyl)phenyl)amino)-7-methoxyquinazolin-6-yl)-1-((S)-3,3-dimethyl-2-((S)-2-(methylamino)propanamido)butanoyl)pyrrolidine-2-carboxamide hydrochloride The procedure of Example 1 was repeated except for using 4-((1H-imidazol-1-yl)methyl)aniline instead of 3-chloro-2,4-difluoro-aniline in <Step 4> to obtain the title compound (17 mg, 5%).

$^1$H NMR (300 MHz, DMSO): δ 9.84 (brs, 1H), 9.59 (s, 1H), 8.89 (s, 1H), 8.59-8.63 (d, 2H), 8.47 (s, 1H), 7.77 (d, 2H), 7.54 (s, 3H), 7.34-7.37 (d, 3H), 7.28 (s, 1H), 5.31 (s, 2H), 4.75-4.79 (m, 1H), 4.52-4.55 (d, 1H), 4.01 (s, 3H), 3.95-4.06 (m, 1H), 3.71-3.81 (m, 2H), 2.47 (s, 3H), 1.92-2.14 (m, 4H), 1.34-1.36 (d, 3H)

MS (ESI$^+$, m/z): 642 [M+H]$^+$

Example 112

Preparation of (S)-1-((S)-3,3-dimethyl-2-((S)-2-(methylamino)propanamido)butanoyl)-N-(4-((3-fluoro-4-(4-methylpiperazin-1-yl)phenyl)amino)-7-methoxyquinazolin-6-yl)pyrrolidine-2-carboxamide The procedure of Example 1 was repeated except for using 3-fluoro-4-(4-methylpiperazin-1-yl)aniline instead of 3-chloro-2,4-difluoro-aniline in <Step 4> to obtain the title compound (48 mg, 1.9%).

$^1$H NMR (300 MHz, CDCl$_3$): δ 9.64 (s, 1H), 8.94 (s, 1H), 8.62 (s, 1H), 7.89 (d, 1H), 7.81 (s, 1H), 7.66-7.60 (m, 1H), 7.34-7.31 (m, 1H), 7.22 (s, 1H), 6.97 (t, 1H), 4.88-4.85 (m, 1H), 4.63 (d, 1H), 4.02-3.97 (m, 4H), 3.73-3.71 (m, 1H), 3.13-3.09 (m, 4H), 2.65-2.63 (m, 4H), 2.42 (s, 3H), 2.38 (s, 3H), 2.19-2.00 (m, 5H), 1.33 (d, 3H), 1.04 (s, 9H).

MS (ESI$^+$, m/z): 678 [M+H]$^+$

Example 113

Preparation of (S)—N-(4-((3-chloro-4-(pyrrolidin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide The procedure of Example 1 was repeated except for using 3-chloro-4-(pyrrolidin-1-yl)aniline instead of 3-chloro-2,4-difluoro-aniline in <Step 4> to obtain the title compound (71 mg, 2.8%).

$^1$H NMR (300 MHz, CDCl$_3$): δ 9.64 (s, 1H), 8.94 (s, 1H), 8.60 (s, 1H), 7.89 (d, 1H), 7.68 (d, 1H), 7.59 (m, 1H), 7.45 (dd, 1H), 7.22 (s, 1H), 6.93 (d, 1H), 4.86 (d, 1H), 4.62 (dd, 1H), 4.08-4.02 (m, 4H), 3.74 (m, 1H), 3.37-3.34 (m, 4H), 3.10 (q, 1H), 2.42 (s, 3H), 2.15-1.93 (m, 9H), 1.33 (d, 3H), 1.04 (s, 9H).

MS (ESI$^+$, m/z): 665 [M+H]$^+$

The compounds obtained in Examples 1 to 113 are represented by the following structural formula, as shown in Table 1 below.

TABLE

| Example | Name | Formula |
|---|---|---|
| 1 | (S)-N-(4-(3-chloro-2,4-difluorophenylamino)-7-methoxyquinazolin-6-yl)-1-((S)-3,3-dimethyl-2-((S)-2-(methylamino)-propanamido)butanoyl)pyrrolidine-2-carboxamide hydrochloride | 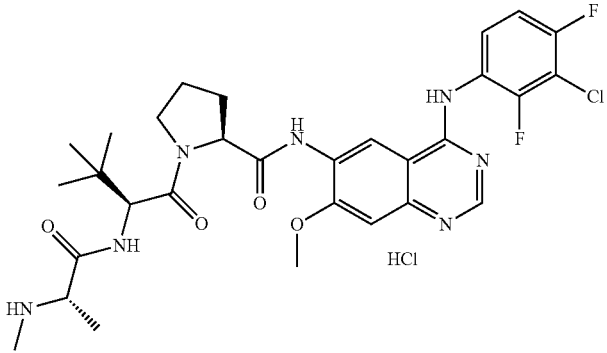 [SMILES: CN[C@@H](C)C(=O)N[C@H](C(=O)N1CCC[C@H]1C(=O)Nc1cc2c(Nc3ccc(F)c(Cl)c3F)ncnc2cc1OC)C(C)(C)C ; Cl] |
| 2 | (S)-N-(4-(3-chloro-2-fluorophenylamino)-7-(2-methoxyethoxy)quinazolin-6-yl)-1-((S)-3,3-dimethyl-2-((S)-2-(methylamino)-propanamido)butanoyl)pyrrolidine-2-carboxamide hydrochloride | 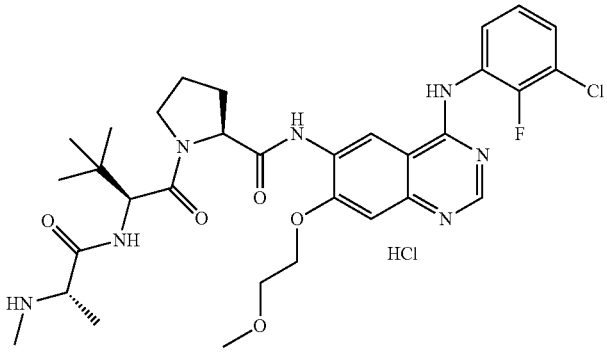 [SMILES: CN[C@@H](C)C(=O)N[C@H](C(=O)N1CCC[C@H]1C(=O)Nc1cc2c(Nc3cccc(Cl)c3F)ncnc2cc1OCCOC)C(C)(C)C ; Cl] |

TABLE-continued

| Example | Name | Formula |
|---|---|---|
| 3 | (S)-N-(4-(5-chlorobenzo[d][1,3]dioxol-4-ylamino)-7-(2-methoxyethoxy)-quinazolin-6-yl)-1-((S)-3,3-dimethyl-2-((S)-2-(methylamino)-propanamido)butanoyl)pyrrolidine-2-carboxamide hydrochloride | 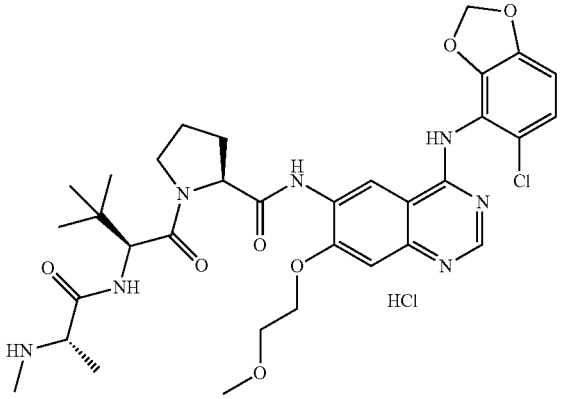 [SMILES: CN[C@@H](C)C(=O)N[C@H](C(=O)N1CCC[C@H]1C(=O)Nc1cc2c(Nc3c(Cl)ccc4c3OCO4)ncnc2cc1OCCOC)C(C)(C)C ; Cl] |
| 4 | (S)-N-(4-(3-chloro-2-fluorophenylamino)quinazolin-6-yl)-1-((S)-3,3-dimethyl-2-((S)-2-(methylamino)propanamido)-butanoyl)pyrrolidine-2-carboxamide hydrochloride | 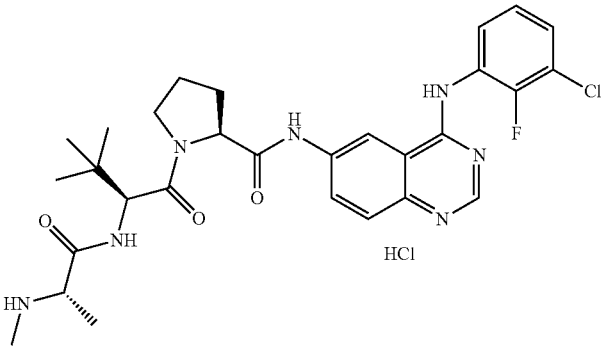 [SMILES: CN[C@@H](C)C(=O)N[C@H](C(=O)N1CCC[C@H]1C(=O)Nc1ccc2ncnc(Nc3cccc(Cl)c3F)c2c1)C(C)(C)C ; Cl] |
| 5 | (S)-N-(4-(3-chloro-4-fluorophenylamino)-7-(2-methoxyethoxy)quinazolin-6-yl)-1-((S)-3,3-dimethyl-2-((S)-2-(methylamino)-propanamido)butanoyl)pyrrolidine-2-carboxamide hydrochloride | 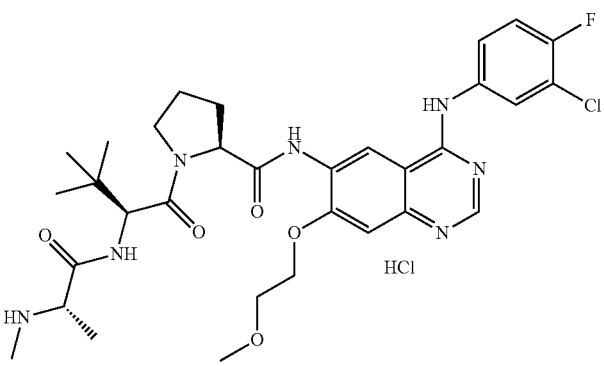 [SMILES: CN[C@@H](C)C(=O)N[C@H](C(=O)N1CCC[C@H]1C(=O)Nc1cc2c(Nc3ccc(F)c(Cl)c3)ncnc2cc1OCCOC)C(C)(C)C ; Cl] |
| 6 | (S)-N-(4-(3-chloro-2,4-difluorophenylamino)-7-(2-methoxyethoxy)quinazolin-6-yl)-1-((S)-3,3-dimethyl-2-((S)-2-(methylamino)propanamido)-butanoyl)pyrrolidine-2-carboxamide hydrochloride | 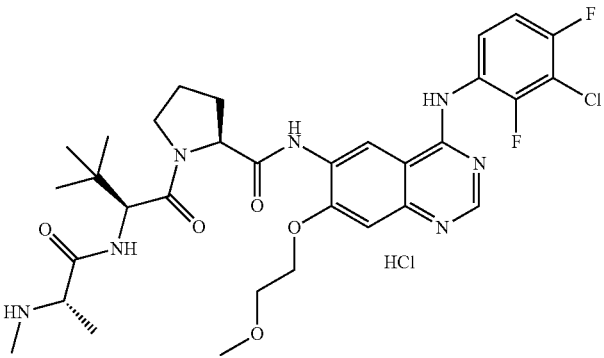 [SMILES: CN[C@@H](C)C(=O)N[C@H](C(=O)N1CCC[C@H]1C(=O)Nc1cc2c(Nc3ccc(F)c(Cl)c3F)ncnc2cc1OCCOC)C(C)(C)C ; Cl] |

TABLE-continued

| Example | Name | Formula |
|---|---|---|
| 7 | (S)-N-(4-(3-chloro-2-fluorophenylamino)-7-(2-methoxyethoxy)quinazolin-6-yl)-1-((S)-3,3-dimethyl-2-((S)-2-(methylamino)propanamido)-butanoyl)pyrrolidine-2-carboxamide hydrochloride | 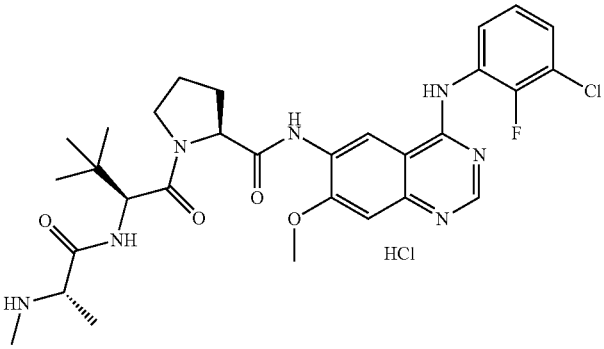 [SMILES: CN[C@@H](C)C(=O)N[C@H](C(=O)N1CCC[C@H]1C(=O)Nc1cc2c(Nc3cccc(Cl)c3F)ncnc2cc1OC)C(C)(C)C ; Cl] |
| 8 | (S)-N-(4-(3,4-dichloro-2-fluorophenylamino)-7-methoxyquinazolin-6-yl)-1-((S)-3,3-dimethyl-2-((S)-2-(methylamino)propanamido)-butanoyl)pyrrolidine-2-carboxamide hydrochloride | 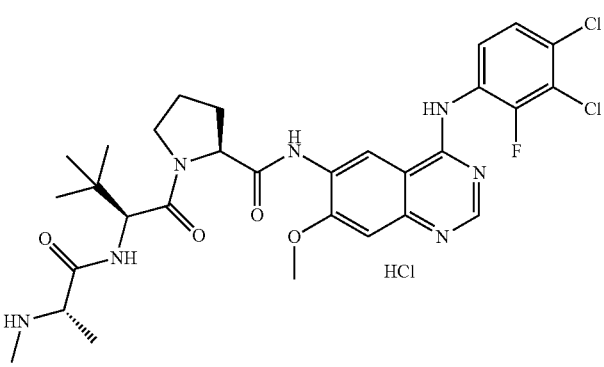 |
| 9 | (S)-N-(4-(4-bromo-2-fluorophenyl-amino)-7-methoxyquinazolin-6-yl)-1-((S)-3,3-dimethyl-2-((S)-2-(methylamino)propanamido)-butanoyl)pyrrolidine-2-carboxamide hydrochloride | 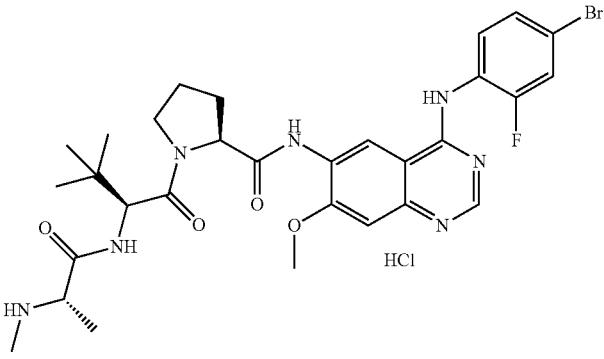 [SMILES: CN[C@@H](C)C(=O)N[C@H](C(=O)N1CCC[C@H]1C(=O)Nc1cc2c(Nc3ccc(Br)cc3F)ncnc2cc1OC)C(C)(C)C ; Cl] |
| 10 | (S)-1-((S)-3,3-dimethyl-2-((S)-2-(methylamino)propanamido)-butanoyl)-N-(4-(2-fluorophenylamino)-7-methoxyquinazolin-6-yl)pyrrolidine-2-carboxamide hydrochloride | 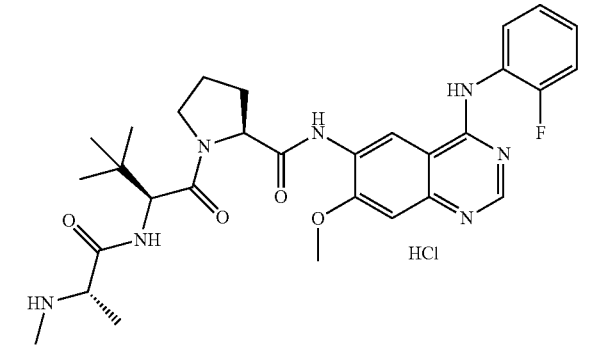 [SMILES: CN[C@@H](C)C(=O)N[C@H](C(=O)N1CCC[C@H]1C(=O)Nc1cc2c(Nc3ccccc3F)ncnc2cc1OC)C(C)(C)C ; Cl] |

TABLE-continued

| Example | Name | Formula |
|---|---|---|
| 11 | (S)-N-(4-phenylamino-7-methoxyquinazolin-6-yl)-1-((S)-3,3-dimethyl-2-((S)-2-(methylamino)propanamido)-butanoyl)pyrrolidine-2-carboxamide hydrochloride | |
| 12 | (S)-1-((S)-2-((S)-2-aminopropanamido)-3,3-dimethylbutanoyl)-N-(4-(3-chloro-2,4-difluorophenylamino)-7-methoxyquinazolin-6-yl)-pyrrolidine-2-carboxamide hydrochloride | |
| 13 | (S)-1-((S)-2-((S)-2-acrylamidopropanamido)-3,3-dimethylbutanoyl)-N-(4-(3-chloro-2,4-difluorophenylamino)-7-methoxyquinazolin-6-yl)-pyrrolidine-2-carboxamide hydrochloride | |
| 14 | (S)-N-(4-(3-chloro-2,4-difluorophenylamino)-7-((S)-tetrahydrofuran-3-yloxy)quinazolin-6-yl)-1-((S)-3,3-dimethyl-2-((S)-2-(methylamino)propanamido)-butanoyl)pyrrolidine-2-carboxamide hydrochloride | |

TABLE-continued

| Example | Name | Formula |
|---|---|---|
| 15 | (S)-N-(4-(3-chloro-2,4-difluoro-phenylamino)-7-methoxyquinazolin-6-yl)-1-((S)-2-cyclohexyl-2-((S)-2-(methylamino)propanamido)acetyl)-pyrrolidine-2-carboxamide hydrochloride | 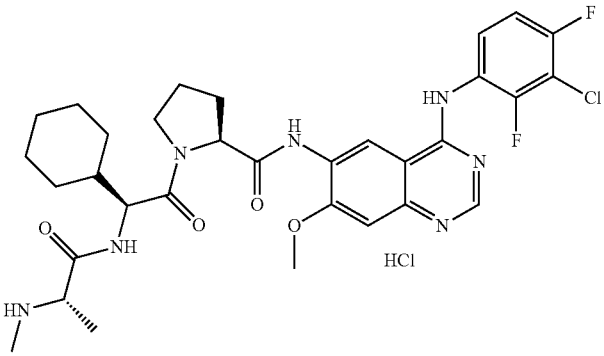 [SMILES: CN[C@@H](C)C(=O)N[C@H](C(=O)N1CCC[C@H]1C(=O)Nc1cc2c(Nc3ccc(F)c(Cl)c3F)ncnc2cc1OC)C1CCCCC1 ; Cl] |
| 16 | (S)-N-(4-(3-chloro-2,4-difluorophenyl-amino)-7-((R)-tetrahydrofuran-3-yloxy)quinazolin-6-yl)-1-((S)-3,3-dimethyl-2-((S)-2-(methylamino)-propanamido)butanoyl)pyrrolidine-2-carboxamide hydrochloride | 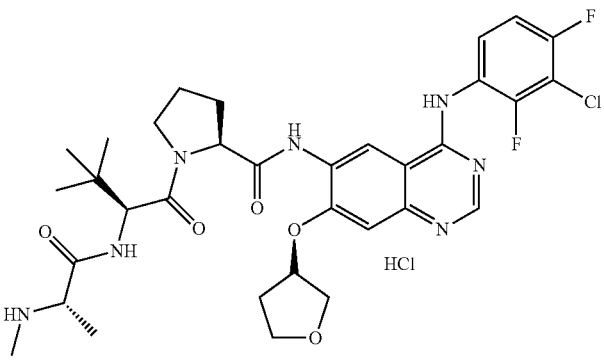 |
| 17 | (S)-1-((S)-3,3-dimethyl-2-((S)-2-(methylamino)propanamido)-butanoyl)-N-(7-methoxy-4-(2,3,4-trifluorophenylamino)quinazolin-6-yl)pyrrolidine-2-carboxamide hydrochloride | 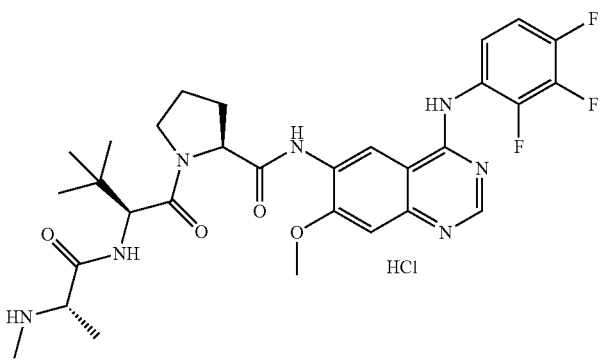 [SMILES: CN[C@@H](C)C(=O)N[C@H](C(=O)N1CCC[C@H]1C(=O)Nc1cc2c(Nc3ccc(F)c(F)c3F)ncnc2cc1OC)C(C)(C)C ; Cl] |
| 18 | (S)-N-(4-(benzylamino)-7-methoxy-quinazolin-6-yl)-1-((S)-3,3-dimethyl-2-((S)-2-(methylamino)-propanamido)butanoyl)pyrrolidine-2-carboxamide hydrochloride | 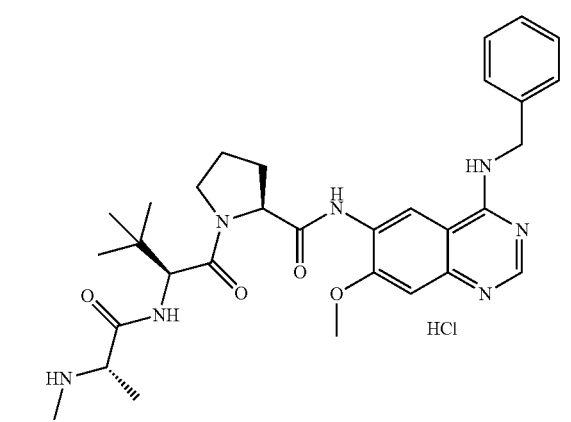 [SMILES: CN[C@@H](C)C(=O)N[C@H](C(=O)N1CCC[C@H]1C(=O)Nc1cc2c(NCc3ccccc3)ncnc2cc1OC)C(C)(C)C ; Cl] |

TABLE-continued

| Example | Name | Formula |
|---|---|---|
| 19 | (S)-N-(4-(3-chloro-4-(6-methylpyridin-3-yloxy)phenylamino)-7-methoxyquinazolin-6-yl)-1-((S)-3,3-dimethyl-2-((S)-2-(methylamino)propanamido)butanoyl)pyrrolidine-2-carboxamide hydrochloride | 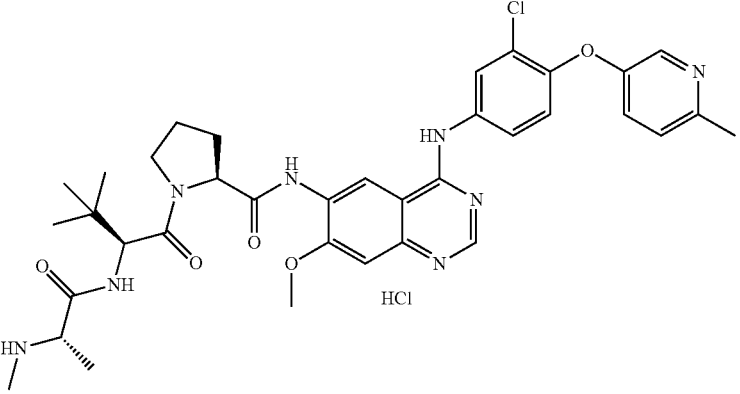 |
| 20 | (S)-N-(4-(3-chloro-2,4-difluorophenylamino)-7-methoxyquinazolin-6-yl)-1-((S)-3,3-dimethyl-2-((S)-2-(methylamino)propanamido)butanoyl)azetidine-2-carboxamide hydrochloride | 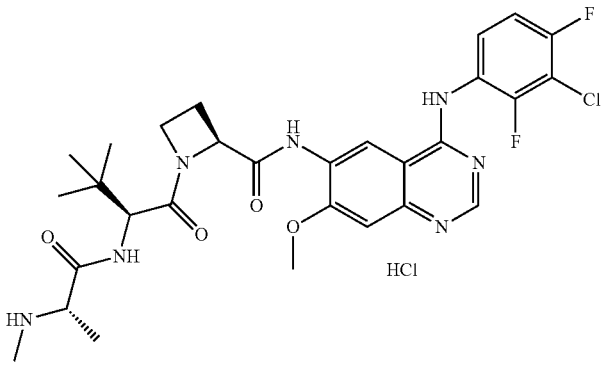 [SMILES: CN[C@@H](C)C(=O)N[C@H](C(=O)N1CC[C@H]1C(=O)Nc1cc2c(Nc3ccc(F)c(Cl)c3F)ncnc2cc1OC)C(C)(C)C ; Cl] |
| 21 | (S)-N-(4-(2-chlorophenylamino)-7-methoxyquinazolin-6-yl)-1-((S)-3,3-dimethyl-2-((S)-2-(methylamino)propanamido)butanoyl)-pyrrolidine-2-carboxamide hydrochloride | 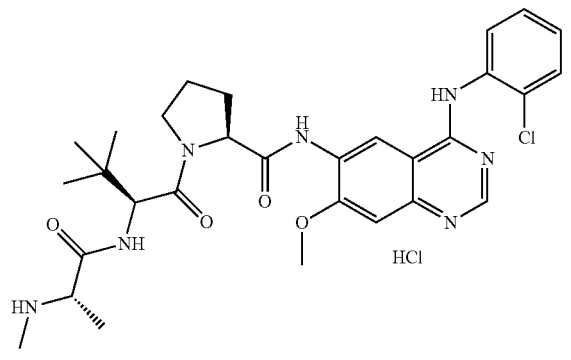 [SMILES: CN[C@@H](C)C(=O)N[C@H](C(=O)N1CCC[C@H]1C(=O)Nc1cc2c(Nc3ccccc3Cl)ncnc2cc1OC)C(C)(C)C ; Cl] |
| 22 | (S)-N-(4-(2-bromophenylamino)-7-methoxyquinazolin-6-yl)-1-((S)-3,3-dimethyl-2-((S)-2-(methylamino)propanamido)butanoyl)-pyrrolidine-2-carboxamide hydrochloride | 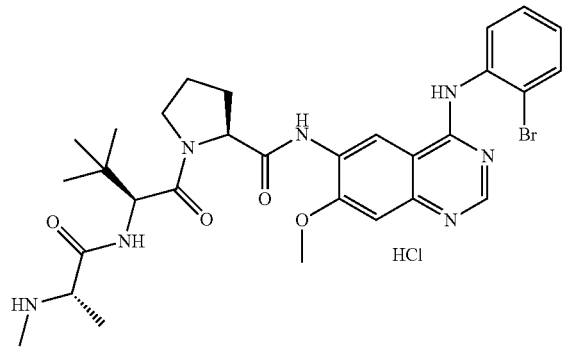 [SMILES: CN[C@@H](C)C(=O)N[C@H](C(=O)N1CCC[C@H]1C(=O)Nc1cc2c(Nc3ccccc3Br)ncnc2cc1OC)C(C)(C)C ; Cl] |

TABLE-continued

| Example | Name |
|---|---|
| 23 | (S)-1-((S)-3,3-dimethyl-2-((S)-2-(methylamino)propanamido)-butanoyl)-N-(7-methoxy-4-(methylamino)quinazolin-6-yl)-pyrrolidine-2-carboxamide |
| 24 | (S)-1-((S)-3,3-dimethyl-2-((S)-2-(methylamino)propanamido)-butanoyl)-N-(7-methoxy-4-(piperidin-1-yl)-quinazolin-6-yl)pyrrolidine-2-carboxamide hydrochloride |
| 25 | (S)-N-(4-(3-chloro-2,4-difluorophenylamino)-7-methoxyquinazolin-6-yl)-1-((S)-3,3-dimethyl-2-((S)-2-(methylamino)propanamido)-butanoyl)azetidine-2-carboxamide |
| 26 | (S)-N-(4-(3-chloro-2,4-difluorophenylamino)-7-methoxyquinazolin-6-yl)-1-((S)-3,3-dimethyl-2-((S)-2-(methylamino)propanamido)-butanoyl)piperidin-3-carboxamide hydrochloride |

TABLE-continued

| Example | Name | Formula |
|---|---|---|
| 27 | (S)-N-(4-(o-toluidino)-7-methoxyquinazolin-6-yl)-1-((S)-3,3-dimethyl-2-((S)-2-(methylamino)propanamido)butanoyl)pyrrolidine-2-carboxamide hydrochloride | 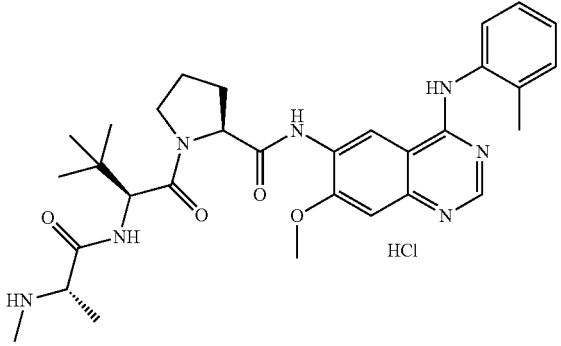 [SMILES: CN[C@@H](C)C(=O)N[C@H](C(=O)N1CCC[C@H]1C(=O)Nc1cc2c(Nc3ccccc3C)ncnc2cc1OC)C(C)(C)C ; Cl] |
| 28 | (S)-N-(4-(2,4-difluorophenylamino)-7-methoxyquinazolin-6-yl)-1-((S)-3,3-dimethyl-2-((S)-2-(methylamino)propanamido)butanoyl)pyrrolidine-2-carboxamide hydrochloride | 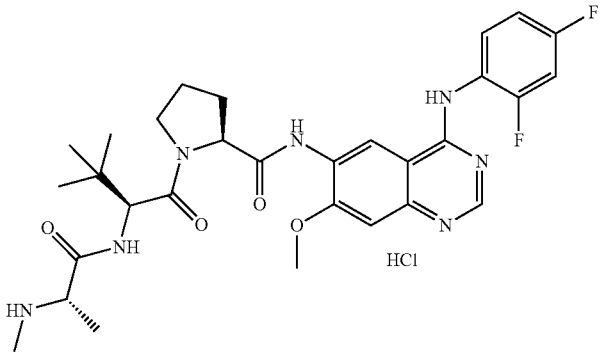 [SMILES: CN[C@@H](C)C(=O)N[C@H](C(=O)N1CCC[C@H]1C(=O)Nc1cc2c(Nc3ccc(F)cc3F)ncnc2cc1OC)C(C)(C)C ; Cl] |
| 29 | (S)-N-(4-(4-chloro-2-fluorophenylamino)-7-methoxyquinazolin-6-yl)-1-((S)-3,3-dimethyl-2-((S)-2-(methylamino)propanamido)butanoyl)pyrrolidine-2-carboxamide hydrochloride | 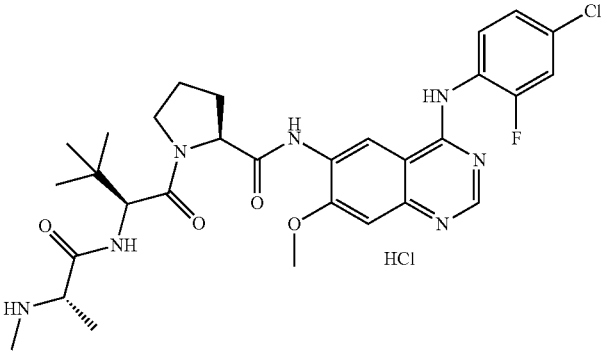 [SMILES: CN[C@@H](C)C(=O)N[C@H](C(=O)N1CCC[C@H]1C(=O)Nc1cc2c(Nc3ccc(Cl)cc3F)ncnc2cc1OC)C(C)(C)C ; Cl] |
| 30 | (S)-N-(4-(2-methoxyphenylamino)-7-methoxyquinazolin-6-yl)-1-((S)-3,3-dimethyl-2-((S)-2-(methylamino)propanamido)butanoyl)pyrrolidine-2-carboxamide hydrochloride | 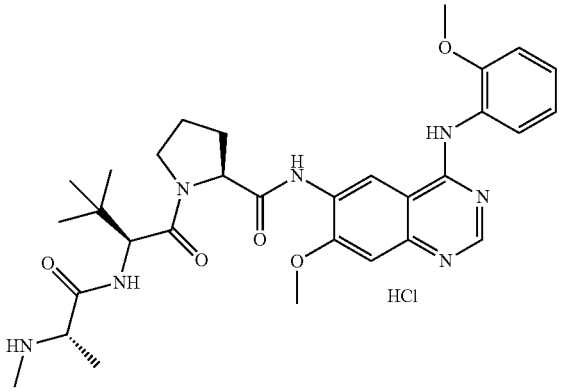 [SMILES: CN[C@@H](C)C(=O)N[C@H](C(=O)N1CCC[C@H]1C(=O)Nc1cc2c(Nc3ccccc3OC)ncnc2cc1OC)C(C)(C)C ; Cl] |

| Example | Name | Formula |
|---|---|---|
| 31 | (S)-1-((S)-3,3-dimethyl-2-((S)-2-(methylamino)propanamido)-butanoyl)-N-(7-methoxy-4-(methyl-(phenyl)amino)quinazolin-6-yl)-pyrrolidine-2-carboxamide hydrochloride | 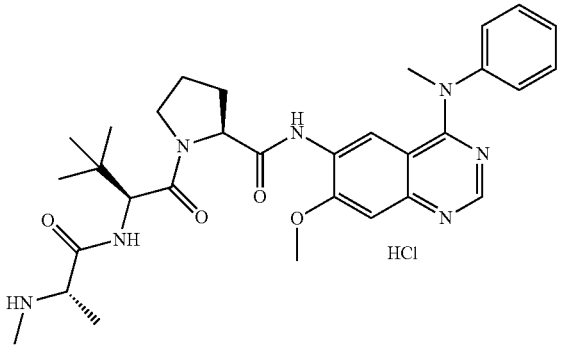 [SMILES: CN[C@@H](C)C(=O)N[C@H](C(=O)N1CCC[C@H]1C(=O)Nc1cc2c(N(C)c3ccccc3)ncnc2cc1OC)C(C)(C)C ; Cl] |
| 32 | (S)-1-((S)-3,3-dimethyl-2-((S)-2-(methylamino)propanamido)-butanoyl)-N-(7-methoxy-4-(naphthalen-2-ylamino)quinazolin-6-yl)pyrrolidine-2-carboxamide | 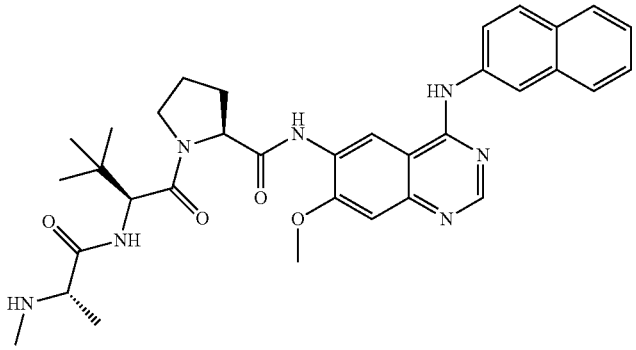 [SMILES: CN[C@@H](C)C(=O)N[C@H](C(=O)N1CCC[C@H]1C(=O)Nc1cc2c(Nc3ccc4ccccc4c3)ncnc2cc1OC)C(C)(C)C] |
| 33 | (S)-1-((S)-3,3-dimethyl-2-((S)-2-(methylamino)propanamido)-butanoyl)-N-(7-methoxy-4-(pyridin-2-ylamino)-quinazolin-6-yl)pyrrolidine-2-carboxamide | 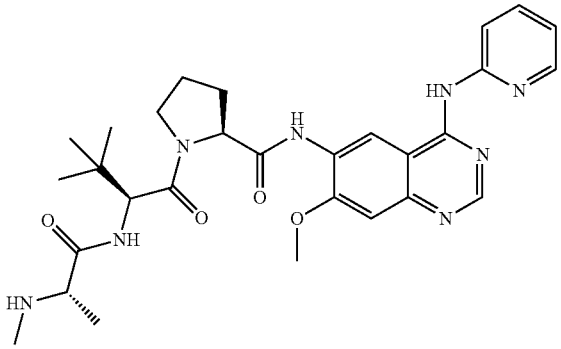 [SMILES: CN[C@@H](C)C(=O)N[C@H](C(=O)N1CCC[C@H]1C(=O)Nc1cc2c(Nc3ccccn3)ncnc2cc1OC)C(C)(C)C] |
| 34 | (S)-1-((S)-3,3-dimethyl-2-((S)-2-(methylamino)propanamido)-butanoyl)-N-(7-methoxy-4-((S)-1-phenylmethylamino)quinazolin-6-yl)-pyrrolidine-2-carboxamide hydrochloride | 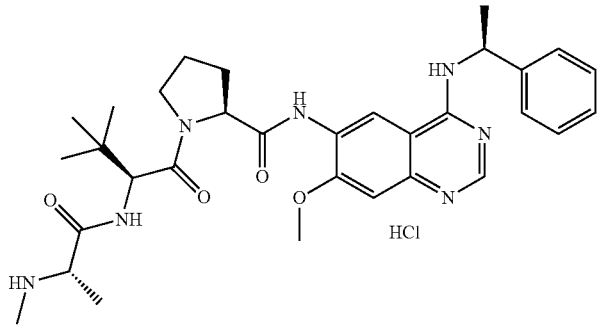 [SMILES: CN[C@@H](C)C(=O)N[C@H](C(=O)N1CCC[C@H]1C(=O)Nc1cc2c(N[C@@H](C)c3ccccc3)ncnc2cc1OC)C(C)(C)C ; Cl] |

| Example | Name | Formula |
|---|---|---|
| 35 | (S)-N-(4-(2,4-difluorobenzylamino)-7-methoxyquinazolin-6-yl)-1-((S)-3,3-dimethyl-2-((S)-2-(methylamino)propanamido)butanoyl)-pyrrolidine-2-carboxamide hydrochloride | 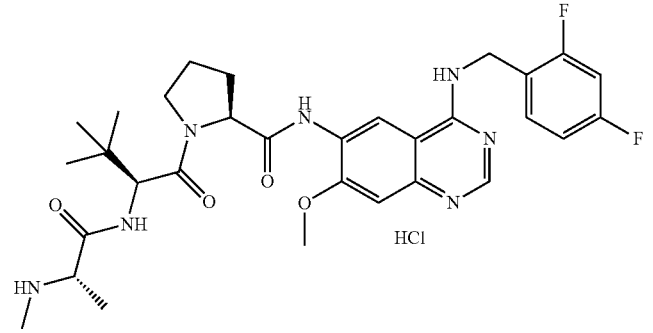 [SMILES: CN[C@@H](C)C(=O)N[C@H](C(=O)N1CCC[C@H]1C(=O)Nc1cc2c(NCc3ccc(F)cc3F)ncnc2cc1OC)C(C)(C)C ; Cl] |
| 36 | (S)-N-(4-amino-7-methoxyquinazolin-6-yl)-1-((S)-3,3-dimethyl-2-((S)-2-(methylamino)propanamido)butanoyl)-pyrrolidine-2-carboxamide | 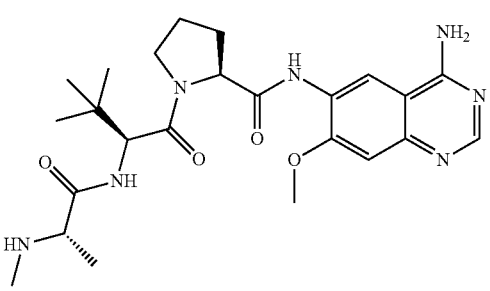 [SMILES: CN[C@@H](C)C(=O)N[C@H](C(=O)N1CCC[C@H]1C(=O)Nc1cc2c(N)ncnc2cc1OC)C(C)(C)C] |
| 37 | (S)-N-(4-(3-chloro-4-(3-fluorobenzyloxy)phenylamino)-7-methoxyquinazolin-6-yl)-1-((S)-3,3-dimethyl-2-((S)-2-(methylamino)propanamido)butanoyl)-pyrrolidine-2-carboxamide hydrochloride | 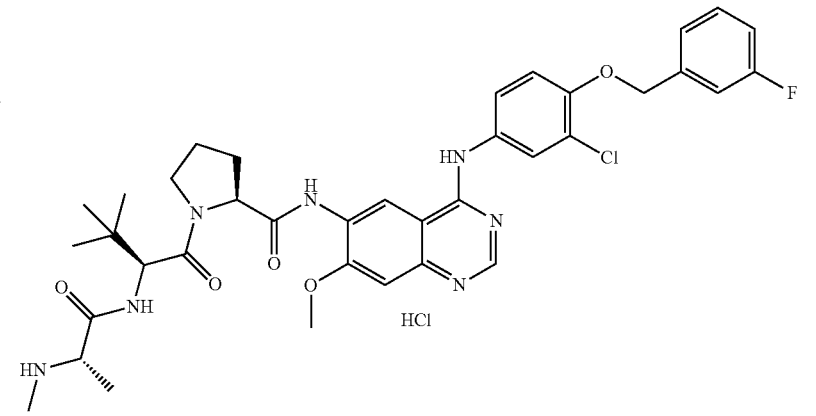 [SMILES: CN[C@@H](C)C(=O)N[C@H](C(=O)N1CCC[C@H]1C(=O)Nc1cc2c(Nc3ccc(OCc4cccc(F)c4)c(Cl)c3)ncnc2cc1OC)C(C)(C)C ; Cl] |
| 38 | (S)-N-(4-(cyclohexylamino)-7-methoxyquinazolin-6-yl)-1-((S)-3,3-dimethyl-2-((S)-2-(methylamino)propanamido)butanoyl)-pyrrolidine-2-carboxamide hydrochloride | 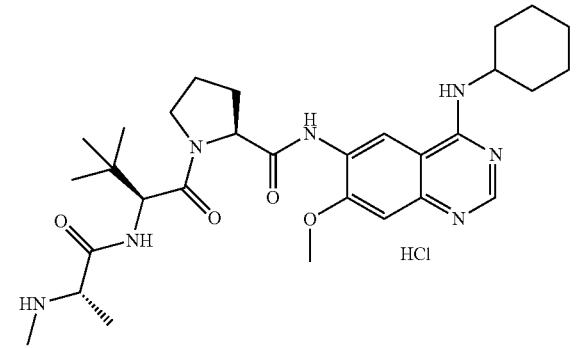 [SMILES: CN[C@@H](C)C(=O)N[C@H](C(=O)N1CCC[C@H]1C(=O)Nc1cc2c(NC3CCCCC3)ncnc2cc1OC)C(C)(C)C ; Cl] |

| Example | Name | Formula |
|---|---|---|
| 39 | (S)-N-(4-(biphenyl-4-ylamino)-7-methoxyquinazolin-6-yl)-1-((S)-3,3-dimethyl-2-((S)-2-(methylamino)propanamido)butanoyl)-pyrrolidine-2-carboxamide hydrochloride | 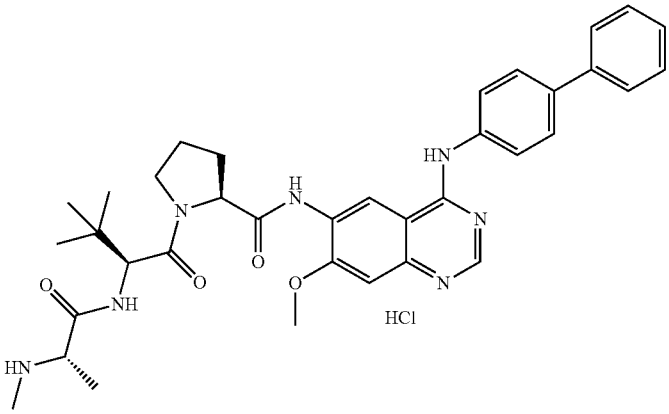 [SMILES: CN[C@@H](C)C(=O)N[C@H](C(=O)N1CCC[C@H]1C(=O)Nc1cc2c(Nc3ccc(-c4ccccc4)cc3)ncnc2cc1OC)C(C)(C)C ; Cl] |
| 40 | (S)-1-((S)-3,3-dimethyl-2-((S)-2-(methylamino)propanamido)butanoyl)-N-(7-methoxy-4-(4-phenoxyphenylamino)quinazolin-6-yl)pyrrolidine-2-carboxamide hydrochloride | 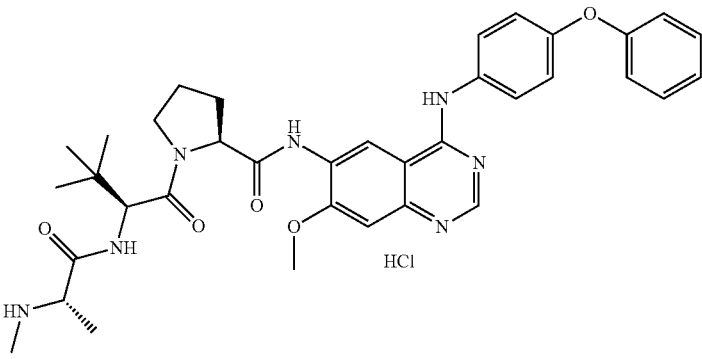 [SMILES: CN[C@@H](C)C(=O)N[C@H](C(=O)N1CCC[C@H]1C(=O)Nc1cc2c(Nc3ccc(Oc4ccccc4)cc3)ncnc2cc1OC)C(C)(C)C ; Cl] |
| 41 | (S)-N-(4-(3-chloro-4-fluorophenylamino)-7-methoxyquinazolin-6-yl)-1-((S)-3,3-dimethyl-2-((S)-2-(methylamino)propanamido)butanoyl)-pyrrolidine-2-carboxamide hydrochloride | 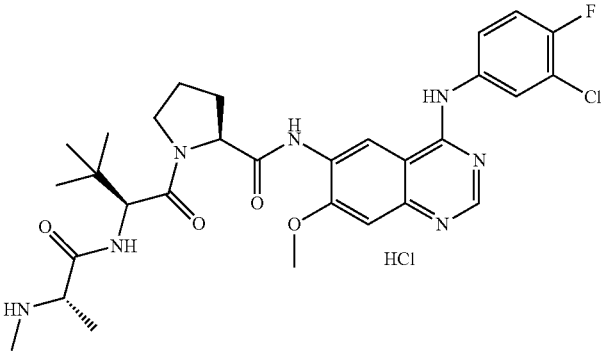 [SMILES: CN[C@@H](C)C(=O)N[C@H](C(=O)N1CCC[C@H]1C(=O)Nc1cc2c(Nc3ccc(F)c(Cl)c3)ncnc2cc1OC)C(C)(C)C ; Cl] |
| 42 | (S)-N-(4-(2,3-difluorophenylamino)-7-methoxyquinazolin-6-yl)-1-((S)-3,3-dimethyl-2-((S)-2-(methylamino)propanamido)butanoyl)-pyrrolidine-2-carboxamide hydrochloride | 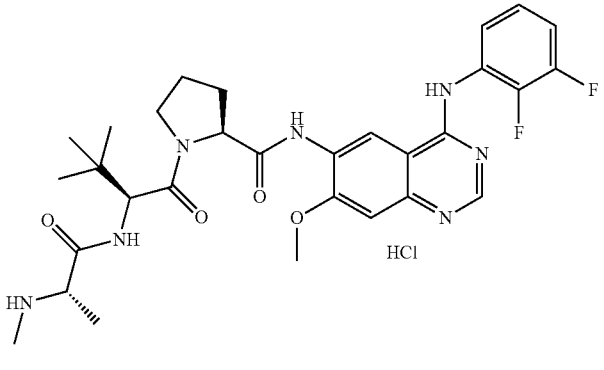 [SMILES: CN[C@@H](C)C(=O)N[C@H](C(=O)N1CCC[C@H]1C(=O)Nc1cc2c(Nc3cccc(F)c3F)ncnc2cc1OC)C(C)(C)C ; Cl] |

TABLE-continued

| Example | Name | Formula |
|---|---|---|
| 43 | (S)-N-(4-(3-chloro-2,4-difluorophenylamino)-7-hydroxyquinazolin-6-yl)-1-((S)-3,3-dimethyl-2-((S)-2-(methylamino)propanamido)butanoyl)-pyrrolidine-2-carboxamide | 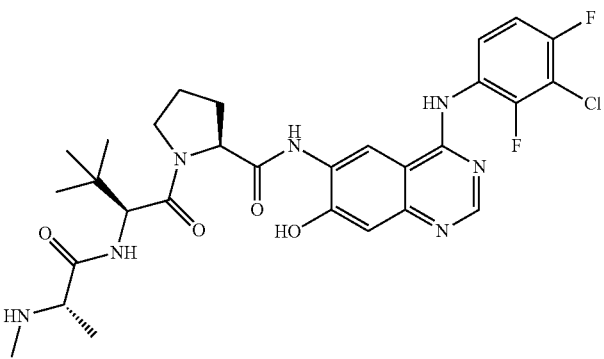 [SMILES: CN[C@@H](C)C(=O)N[C@H](C(=O)N1CCC[C@H]1C(=O)Nc1cc2c(Nc3ccc(F)c(Cl)c3F)ncnc2cc1O)C(C)(C)C] |
| 44 | (S)-N-((S)-1-((S)-2-(4-((4-bromo-2-fluorophenylamino)-6-methoxyquinazolinyl-7-oxy)methyl)-piperidine)-1-carbonyl)-1-pyrrolidinyl)-3,3-dimethyloxobutan-2-yl)-2-(methylamino)propanamide hydrochloride | 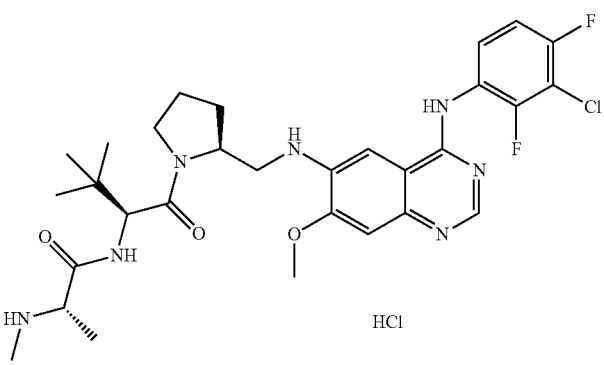 [SMILES: CN[C@@H](C)C(=O)N[C@H](C(=O)N1CCC[C@H]1CNc1cc2c(Nc3ccc(F)c(Cl)c3F)ncnc2cc1OC)C(C)(C)C ; Cl] |
| 45 | (S)-N-(4-(3-chloro-2,4-difluorophenylamino)-7-methoxy-quinazolin-6-yl)-1-((2S,3R)-2-((S)-2-(methylamino)propanamido)-3-(prop-2-ynyloxy)butanoyl)-pyrrolidine-2-carboxamide hydrochloride | 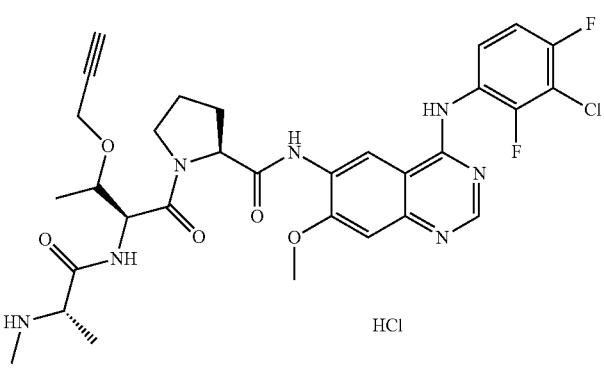 [SMILES: C#CCOC(C)[C@H](NC(=O)[C@H](C)NC)C(=O)N1CCC[C@H]1C(=O)Nc1cc2c(Nc3ccc(F)c(Cl)c3F)ncnc2cc1OC ; Cl] |
| 46 | (2S,4R)-4-(benzyloxy)-N-(4-(3-chloro-2,4-difluorophenylamino)-7-methoxyquinazolin-6-yl)-1-((S)-3,3-dimethyl-2-((S)-2-(methylamino)propanamido)-butanoyl)pyrrolidine-2-carboxamide hydrochloride | 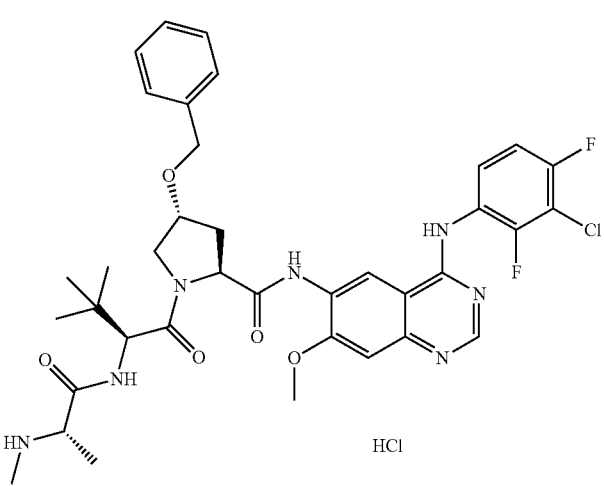 [SMILES: CN[C@@H](C)C(=O)N[C@H](C(=O)N1C[C@H](OCc2ccccc2)C[C@H]1C(=O)Nc1cc2c(Nc3ccc(F)c(Cl)c3F)ncnc2cc1OC)C(C)(C)C ; Cl] |

TABLE-continued

| Example | Name | Formula |
|---|---|---|
| 47 | (S)-1-((S)-3,3-dimethyl-2-((S)-2-(methylamino)propanamido)-butanoyl)-N-(7-methoxy-4-(2-morpholinophenylamino)quinazolin-6-yl)pyrrolidine-2-carboxamide | |
| 48 | (S)-N-(4-(3-chloro-2,4-difluorophenylamino)quinazolin-6-yl)-1-((S)-3,3-dimethyl-2-((S)-2-(methylamino)propanamido)butanoyl)-pyrrolidine-2-carboxamide | |
| 49 | (S)-1-((S)-3,3-dimethyl-2-((S)-2-(methylamino)propanamido)-butanoyl)-N-(7-methoxy-4-(4-methoxyphenylamino)quinazolin-6-yl)pyrrolidine-2-carboxamide hydrochloride | |
| 50 | (S)-N-(4-(3,4-dihydroquinoline-1(2H)-yl)-7-methoxyquinazolin-6-yl)-1-((S)-3,3-dimethyl-2-((S)-2-(methylamino)propanamido)butanoyl)-pyrrolidine-2-carboxamide hydrochloride | |

TABLE-continued

| Example | Name | Formula |
|---|---|---|
| 51 | (S)-N-(4-(5-chlorobenzo[d][1,3]dioxol-4-ylamino)-7-methoxyquinazolin-6-yl)-1-((S)-3,3-dimethyl-2-((S)-2-(methylamino)propanamido)butanoyl)-pyrrolidine-2-carboxamide hydrochloride | 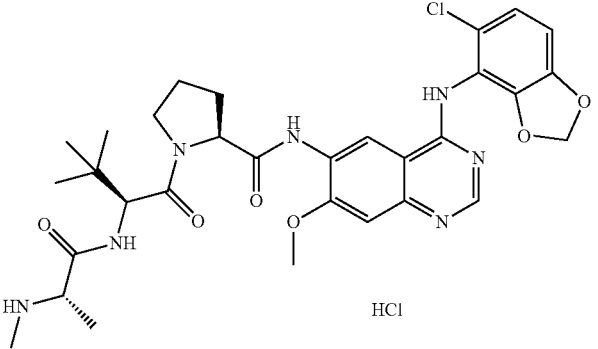 [SMILES: CN[C@@H](C)C(=O)N[C@H](C(=O)N1CCC[C@H]1C(=O)Nc1cc2c(Nc3c(Cl)ccc4c3OCO4)ncnc2cc1OC)C(C)(C)C ; Cl] HCl |
| 52 | (S)-N-(4-(2,3-dihydro-1H-inden-5-ylamino)-7-methoxyquinazolin-6-yl)-1-((S)-3,3-dimethyl-2-((S)-2-(methylamino)propanamido)butanoyl)-pyrrolidine-2-carboxamide hydrochloride | 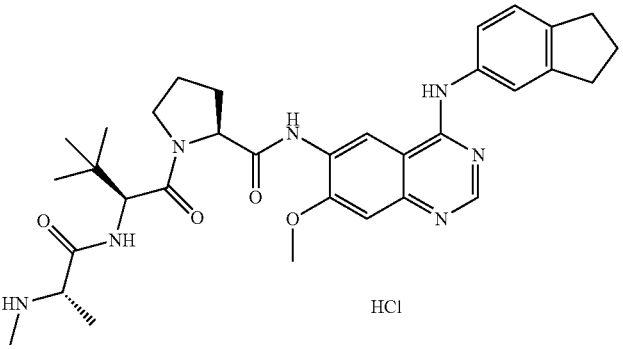 [SMILES: CN[C@@H](C)C(=O)N[C@H](C(=O)N1CCC[C@H]1C(=O)Nc1cc2c(Nc3ccc4c(c3)CCC4)ncnc2cc1OC)C(C)(C)C ; Cl] HCl |
| 53 | (S)-1-((S)-3,3-dimethyl-2-((S)-2-(methylamino)propanamido)-butanoyl)-N-(7-methoxy-4-(quinoline-6-ylamino)-quinazolin-6-yl)pyrrolidine-2-carboxamide | 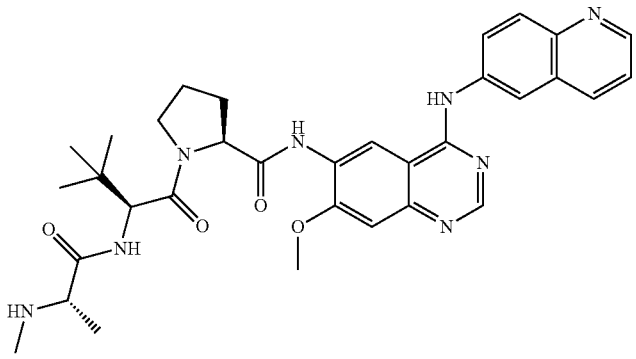 [SMILES: CN[C@@H](C)C(=O)N[C@H](C(=O)N1CCC[C@H]1C(=O)Nc1cc2c(Nc3ccc4ncccc4c3)ncnc2cc1OC)C(C)(C)C] |
| 54 | (S)-N-(4-(1H-indazol-5-ylamino)-7-methoxyquinazolin-6-yl)-1-((S)-3,3-dimethyl-2-((S)-2-(methylamino)propanamido)butanoyl)-pyrrolidine-2-carboxamide | 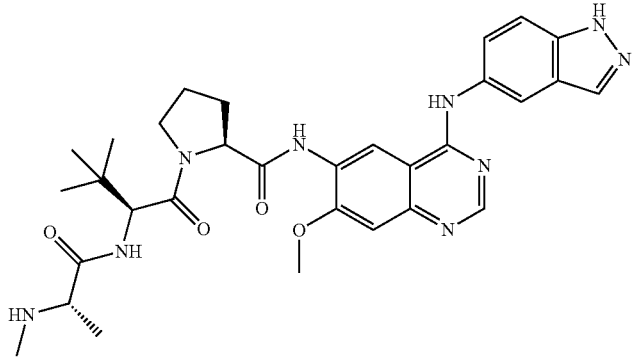 [SMILES: CN[C@@H](C)C(=O)N[C@H](C(=O)N1CCC[C@H]1C(=O)Nc1cc2c(Nc3ccc4[nH]ncc4c3)ncnc2cc1OC)C(C)(C)C] |

TABLE-continued

| Example | Name | Formula |
|---|---|---|
| 55 | (S)-1-((S)-3,3-dimethyl-2-((S)-2-(methylamino)propanamido)-butanoyl)-N-(4-(4-fluorophenylamino)-7-methoxyquinazolin-6-yl)pyrrolidine-2-carboxamide | |
| 56 | (S)-N-(4-(4-chlorophenylamino)-7-methoxyquinazolin-6-yl)-1-((S)-3,3-dimethyl-2((S)-2-(methylamino)propanamido)butanoyl)-pyrrolidine-2-carboxamide | |
| 57 | (S)-1-((S)-3,3-dimethyl-2-((S)-2-(methylamino)propanamido)-butanoyl)-N-(7-methoxy-4-(3-methoxyphenylamino)-quinazolin-6-yl)pyrrolidine-2-carboxamide hydrochloride | |
| 58 | (S)-N-(4-(2,4-dichlorophenylamino)-7-methoxyquinazolin-6-yl)-1-((S)-3,3-dimethyl-2-((S)-2-(methylamino)propanamido)butanoyl)-pyrrolidine-2-carboxamide hydrochloride | |

TABLE-continued

| Example | Name | Formula |
|---|---|---|
| 59 | (S)-N-(4-(2,6-difluorophenylamino)-7-methoxyquinazolin-6-yl)-1-((S)-3,3-dimethyl-2-((S)-2-(methylamino)propanamido)butanoyl)-pyrrolidine-2-carboxamide | |
| 60 | (S)-1-((S)-3,3-dimethyl-2-((S)-2-(methylamino)propanamido)-butanoyl)-N-(4-(4-(4-ethylpiperazin-1-yl)-phenylamino)-7-methoxyquinazolin-6-yl)pyrrolidine-2-carboxamide | |
| 61 | (S)-N-(4-(benzo[d][1,3]dioxol-5-ylamino)-7-methoxyquinazolin-6-yl)-1-((S)-3,3-dimethyl-2-((S)-2-(methylamino)propanamido)butanoyl)-pyrrolidine-2-carboxamide | |
| 62 | (S)-1-((S)-3,3-dimethyl-2-((S)-2-(methylamino)propanamido)-butanoyl)-N-(7-methoxy-4-(quinoline-3-ylamino)quinazolin-6-yl)pyrrolidine-2-carboxamide dihydrochloride | |

TABLE-continued

| Example | Name | Formula |
|---|---|---|
| 63 | (S)-1-((S)-3,3-dimethyl-2-((S)-2-(methylamino)propanamido)butanoyl)-N-(7-methoxy-4-(quinoline-5-ylamino)quinazolin-6-yl)pyrrolidine-2-carboxamide hydrochloride | 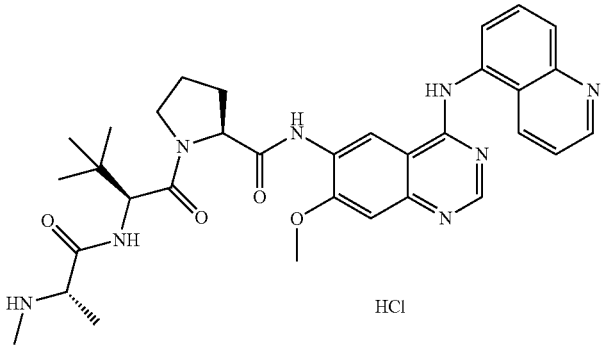 [SMILES: CN[C@@H](C)C(=O)N[C@H](C(=O)N1CCC[C@H]1C(=O)Nc1cc2c(Nc3cccc4ncccc34)ncnc2cc1OC)C(C)(C)C ; Cl] |
| 64 | (S)-1-((S)-3,3-dimethyl-2-((S)-2-(methylamino)propanamido)butanoyl)-N-(7-methoxy-4-(4-dimethylamino)phenylamino)quinazolin-6-yl)pyrrolidine-2-carboxamide dihydrochloride | 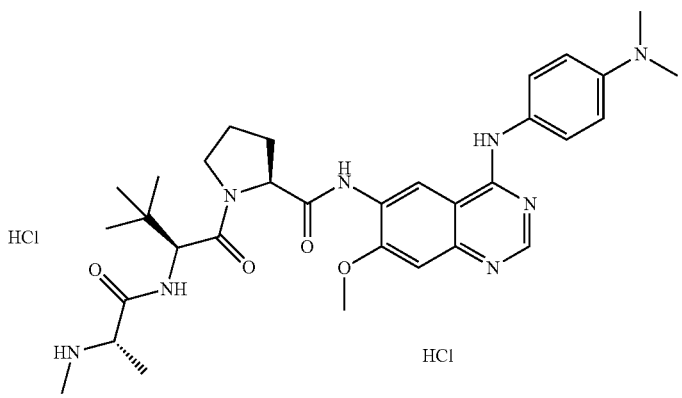 |
| 65 | (S)-1-((S)-3,3-dimethyl-2-((S)-2-(methylamino)propanamido)butanoyl)-N-(7-methoxy-4-(4-(pyrrolidine-1-yl)phenylamino)quinazolin-6-yl)pyrrolidine-2-carboxamide dihydrochloride | 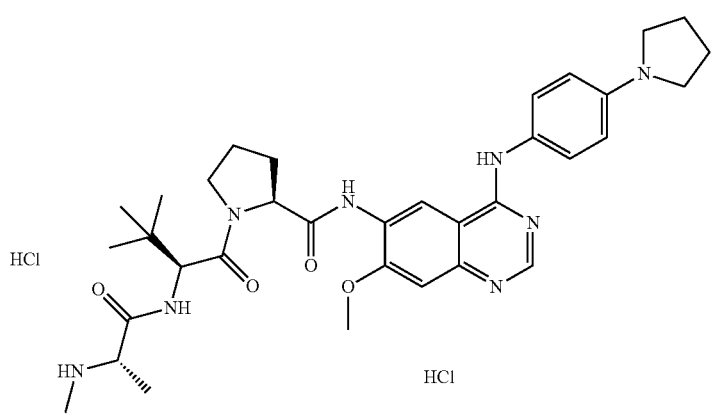 [SMILES: Cl ; CN[C@@H](C)C(=O)N[C@H](C(=O)N1CCC[C@H]1C(=O)Nc1cc2c(Nc3ccc(N4CCCC4)cc3)ncnc2cc1OC)C(C)(C)C ; Cl] |
| 66 | (S)-1-((S)-3,3-dimethyl-2-((S)-2-(methylamino)propanamido)butanoyl)-N-(7-methoxy-4-(4-(piperidin-1-yl)phenylamino)quinazolin-6-yl)pyrrolidine-2-carboxamide dihydrochloride | 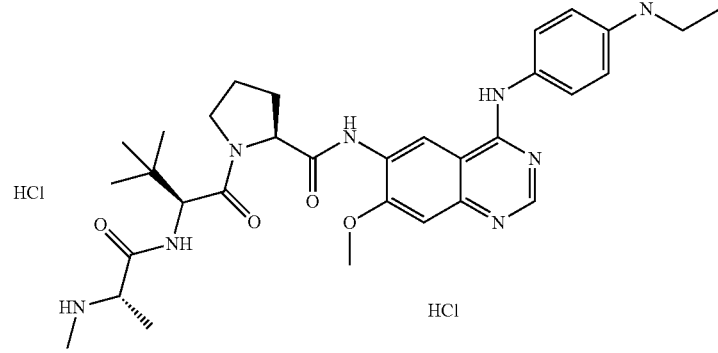 |

TABLE-continued

| Example | Name | Formula |
|---|---|---|
| 67 | (S)-1-((S)-3,3-dimethyl-2-((S)-2-(methylamino)propanamido)-butanoyl)-N-(7-methoxy-4-(4-(4-methylpiperazin-1-yl)-phenylamino)quinazolin-6-yl)-pyrrolidine-2-carboxamide dihydrochloride | 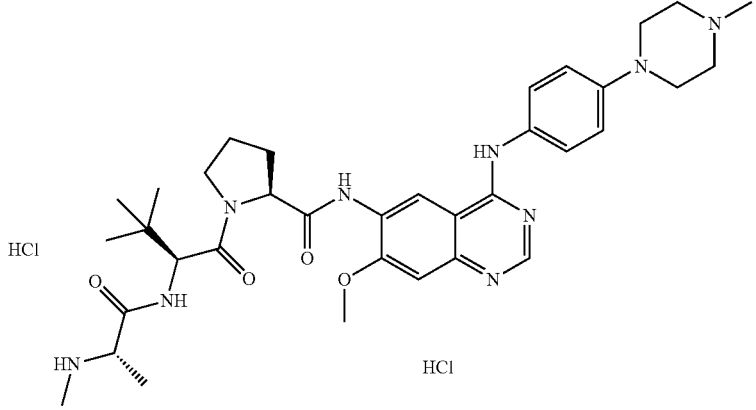 |
| 68 | (S)-1-((S)-3,3-dimethyl-2-((S)-2-(methylamino)propanamido)-butanoyl)-N-(7-methoxy-4-(4-diethylamino)phenylamino)-quinazolin-6-yl)pyrrolidine-2-carboxamide dihydrochloride | 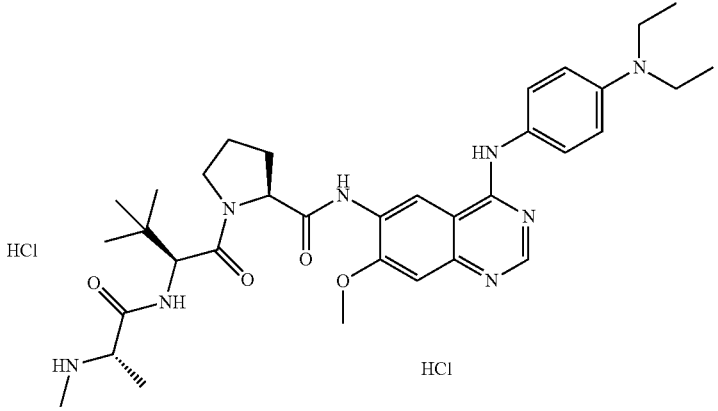 [SMILES: Cl ; CCN(CC)c1ccc(Nc2ncnc3cc(OC)c(NC(=O)[C@@H]4CCCN4C(=O)[C@@H](NC(=O)[C@H](C)NC)C(C)(C)C)cc23)cc1 ; Cl] |
| 69 | (S)-N-(4-(4-acetamidophenylamino)-7-methoxyquinazolin-6-yl)-1-((S)-3,3-dimethyl-2-((S)-2-(methylamino)propanamido)butanoyl)-pyrrolidine-2-carboxamide | 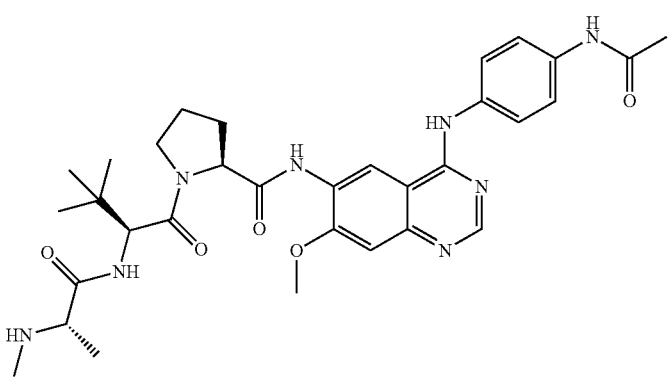 [SMILES: CN[C@@H](C)C(=O)N[C@H](C(=O)N1CCC[C@H]1C(=O)Nc1cc2c(Nc3ccc(NC(C)=O)cc3)ncnc2cc1OC)C(C)(C)C] |

| Example | Name | Formula |
|---|---|---|
| 70 | (S)-1-((S)-3,3-dimethyl-2-((S)-2-(methylamino)propanamido)-butanoyl)-N-(4-(4-(4-ethylpiperazin-1-yl)-3-(trifluoromethyl)-phenylamino)-7-methoxyquinazolin-6-yl)-pyrrolidine-2-carboxamide dihydrochloride | 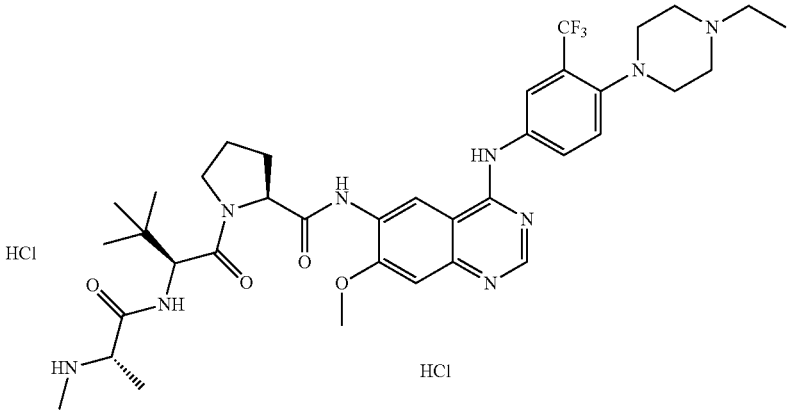 [SMILES: Cl ; CCN1CCN(c2ccc(Nc3ncnc4cc(OC)c(NC(=O)[C@@H]5CCCN5C(=O)[C@@H](NC(=O)[C@H](C)NC)C(C)(C)C)cc34)cc2C(F)(F)F)CC1 ; Cl] |
| 71 | (S)-1-((S)-3,3-dimethyl-2-((S)-2-(methylamino)propanamido)-butanoyl)-N-(4-(4-(4-ethylpiperazin-1-yl)-3-fluorophenylamino)-7-methoxyquinazolin-6-yl)pyrrolidine-2-carboxamide dihydrochloride | 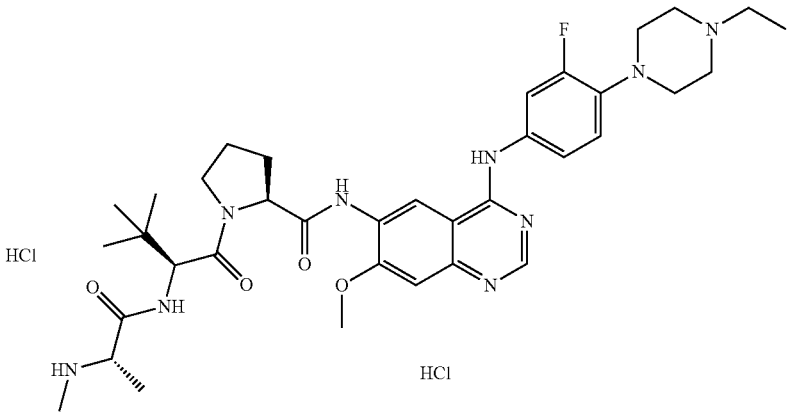 [SMILES: Cl ; CCN1CCN(c2ccc(Nc3ncnc4cc(OC)c(NC(=O)[C@@H]5CCCN5C(=O)[C@@H](NC(=O)[C@H](C)NC)C(C)(C)C)cc34)cc2F)CC1 ; Cl] |
| 72 | (S)-N-(4-((1,1-dioxide-4-thiomorpholinyl)phenylamino)-7-methoxyquinazolin-6-yl)-1-((S)-3,3-dimethyl-2-((S)-2-(methylamino)propanamido)butanoyl)-pyrrolidine-2-carboxamide | 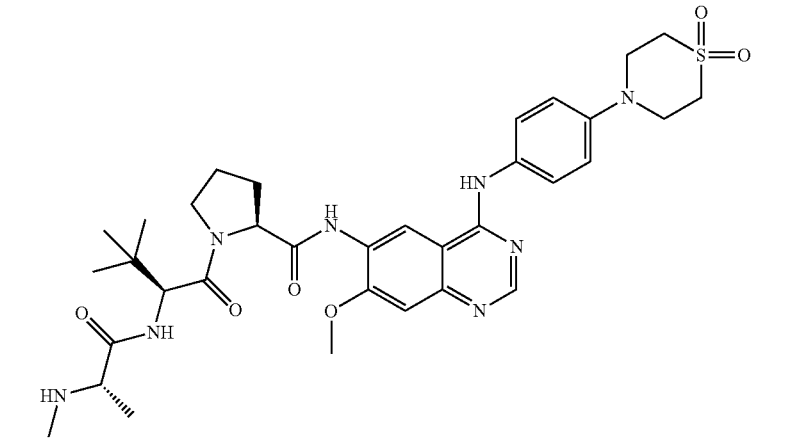 [SMILES: CN[C@@H](C)C(=O)N[C@H](C(=O)N1CCC[C@H]1C(=O)Nc1cc2c(Nc3ccc(N4CCS(=O)(=O)CC4)cc3)ncnc2cc1OC)C(C)(C)C] |

| Example | Name | Formula |
|---|---|---|
| 73 | (S)-1-((S)-3,3-dimethyl-2-((S)-2-(methylamino)propanamido)-butanoyl)-N-(7-methoxy-4-(pyridin-4-ylamino)-quinazolin-6-yl)pyrrolidine-2-carboxamide hydrochloride | |
| 74 | (S)-1-((S)-3,3-dimethyl-2-((S)-2-(methylamino)propanamido)-butanoyl)-N-(7-methoxy-4-(4-(methylcarbamoyl)phenylamino)-quinazolin-6-yl)pyrrolidine-2-carboxamide | |
| 75 | (S)-N-(4-(5-acetamino-2-chlorophenylamino)-7-methoxyquinazolin-6-yl)-1-((S)-3,3-dimethyl-2-((S)-2-(methylamino)propanamido)butanoyl)-pyrrolidine-2-carboxamide | |
| 76 | (S)-N-(4-(4-benzamidophenylamino)-7-methoxyquinazolin-6-yl)-1-((S)-3,3-dimethyl-2-((S)-2-(methylamino)propanamido)butanoyl)-pyrrolidine-2-carboxamide | |

TABLE-continued

| Example | Name | Formula |
|---|---|---|
| 77 | (S)-N-(4-((cyclohexylmethyl)amino)-7-methoxyquinazolin-6-yl)-1-((S)-3,3-dimethyl-2-((S)-2-(methylamino)propanamido)butanoyl)-pyrrolidine-2-carboxamide hydrochloride | 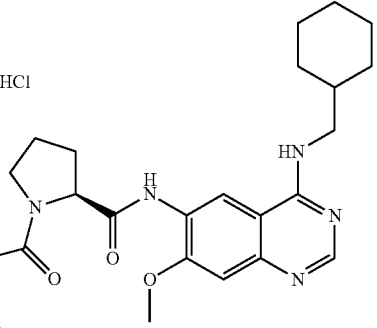 |
| 78 | (S)-N-(4-((2-chloropyridin-3-yl)-amino)-7-methoxyquinazolin-6-yl)-1-((S)-3,3-dimethyl-2-((S)-2-(methylamino)propanamido)butanoyl)-pyrrolidine-2-carboxamide hydrochloride | 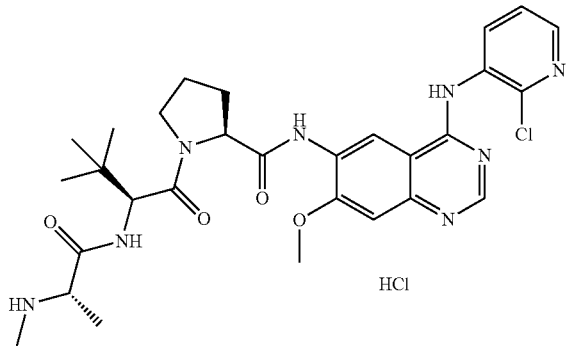 [SMILES: CN[C@@H](C)C(=O)N[C@H](C(=O)N1CCC[C@H]1C(=O)Nc1cc2c(Nc3cccnc3Cl)ncnc2cc1OC)C(C)(C)C ; Cl] |
| 79 | (S)-N-(4-((6-chloropyridin-3-yl)-amino)-7-methoxyquinazolin-6-yl)-1-((S)-3,3-dimethyl-2-((S)-2-(methylamino)propanamido)butanoyl)-pyrrolidine-2-carboxamide hydrochloride | 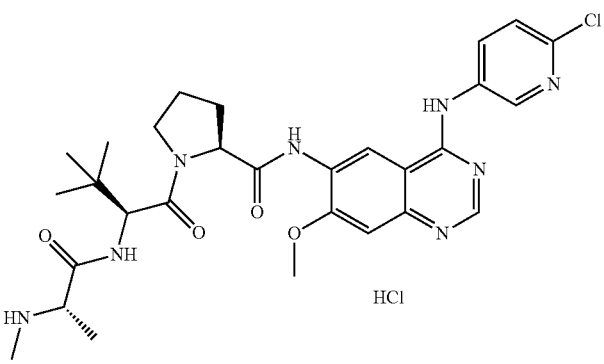 [SMILES: CN[C@@H](C)C(=O)N[C@H](C(=O)N1CCC[C@H]1C(=O)Nc1cc2c(Nc3ccc(Cl)nc3)ncnc2cc1OC)C(C)(C)C ; Cl] |
| 80 | (S)-N-(4-((4-bromo-2-chlorophenyl)-amino)-7-methoxyquinazolin-6-yl)-1-((S)-3,3-dimethyl-2-((S)-2-(methylamino)propanamido)butanoyl)-pyrrolidine-2-carboxamide hydrochloride | 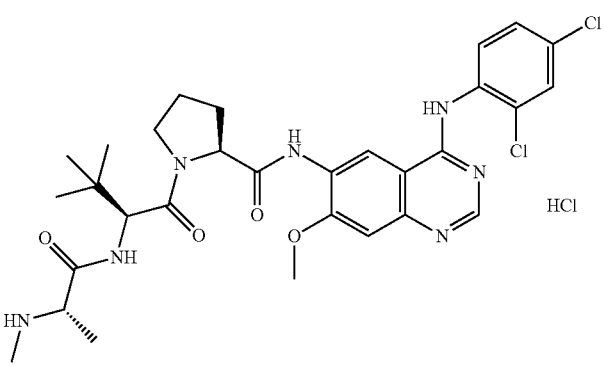 [SMILES: CN[C@@H](C)C(=O)N[C@H](C(=O)N1CCC[C@H]1C(=O)Nc1cc2c(Nc3ccc(Cl)cc3Cl)ncnc2cc1OC)C(C)(C)C ; Cl] |

TABLE-continued

| Example | Name | Formula |
|---|---|---|
| 81 | (S)-N-(4-((2,3-dichlorophenyl)-amino)-7-methoxyquinazolin-6-yl)-1-((S)-3,3-dimethyl-2-((S)-2-(methylamino)propanamido)butanoyl)-pyrrolidine-2-carboxamide hydrochloride | 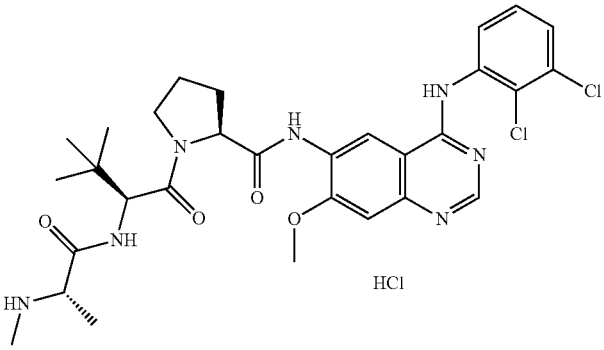 [SMILES: CN[C@@H](C)C(=O)N[C@H](C(=O)N1CCC[C@H]1C(=O)Nc1cc2c(Nc3cccc(Cl)c3Cl)ncnc2cc1OC)C(C)(C)C ; Cl] |
| 82 | (S)-N-(4-((2-bromo-4-fluorophenyl)-amino)-7-methoxyquinazolin-6-yl)-1-((S)-3,3-dimethyl-2-((S)-2-(methylamino)propanamido)butanoyl)-pyrrolidine-2-carboxamide hydrochloride | 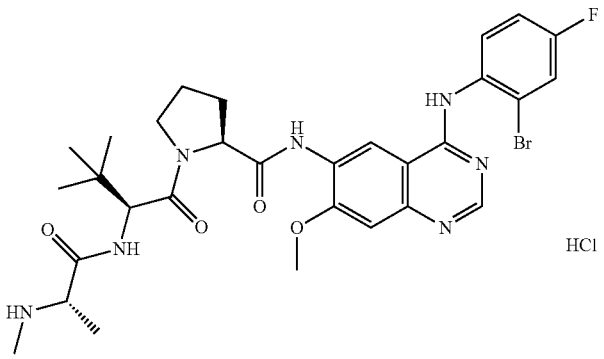 [SMILES: CN[C@@H](C)C(=O)N[C@H](C(=O)N1CCC[C@H]1C(=O)Nc1cc2c(Nc3ccc(F)cc3Br)ncnc2cc1OC)C(C)(C)C ; Cl] |
| 83 | (S)-1-((S)-3,3-dimethyl-2-((S)-2-(methylamino)propanamido)-butanoyl)-N-(7-methoxy-4-(phenylamino)-quinazolin-6-yl)pyrrolidine-2-carboxamide hydrochloride | 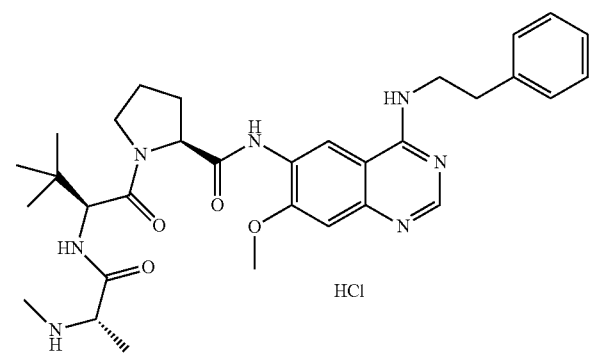 [SMILES: CN[C@@H](C)C(=O)N[C@H](C(=O)N1CCC[C@H]1C(=O)Nc1cc2c(NCCc3ccccc3)ncnc2cc1OC)C(C)(C)C ; Cl] |
| 84 | (S)-1-((S)-3,3-dimethyl-2-((S)-2-(methylamino)propanamido)butanoyl)-N-(7-methoxy-4-((6-(prop-2-yn-1-yloxy)pyridin-3-yl)-amino)quinazolin-6-yl)pyrrolidine-2-carboxamidehydrochloride | 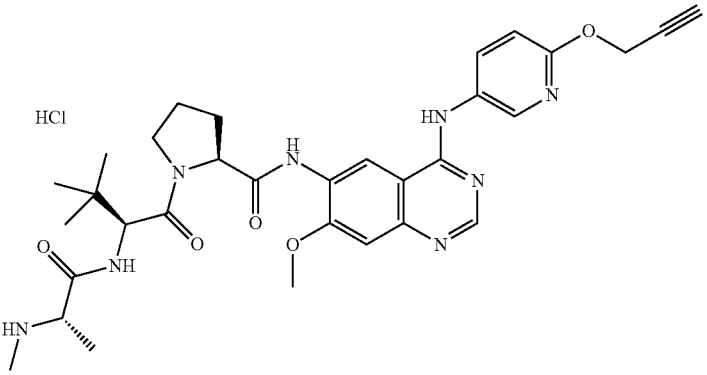 [SMILES: C#CCOc1ccc(Nc2ncnc3cc(OC)c(NC(=O)[C@@H]4CCCN4C(=O)[C@@H](NC(=O)[C@H](C)NC)C(C)(C)C)cc23)cn1 ; Cl] |

TABLE-continued

| Example | Name | Formula |
|---|---|---|
| 85 | (S)-1-((S)-3,3-dimethyl-2-((S)-2-(methylamino)propanamido)-butanoyl)-N-(4-((3-fluoro-4-(piperidin-1-yl)phenyl)amino)-7-methoxyquinazolin-6-yl)pyrrolidine-2-carboxamide hydrochloride | |
| 86 | (S)-N-(4-((3-chloro-4-(4-methyl-piperazin-1-yl)phenyl)amino)-7-methoxyquinazolin-6-yl)-1-((S)-3,3-dimethyl-2-((S)-2-(methylamino)-propanamido)butanoyl)pyrrolidine-2-carboxamide hydrochloride | |
| 87 | (S)-N-(4-((4-bromo-3-chloro-2-fluorophenyl)amino)-7-methoxy-quinazolin-6-yl)-1-((S)-3,3-dimethyl-2-((S)-2-(methylamino)propanamido)butanoyl)-pyrrolidine-2-carboxamide hydrochloride | |
| 88 | (S)-N-(4-((4-(1H-imidazol-1-yl)phenyl)amino)-7-methoxyquinazolin-6-yl)-1-((S)-3,3-dimethyl-2-((S)-2-(methylamino)propanamido)butanoyl)-pyrrolidine-2-carboxamide hydrochloride | |

| Example | Name | Formula |
|---|---|---|
| 89 | (S)-1-((S)-3,3-dimethyl-2-((S)-2-(methylamino)propanamido)-butanoyl)-N-(4-(3-(2-fluorophenyl)-ureido)-7-methoxyquinazolin-6-yl)pyrrolidine-2-carboxamide hydrochloride | 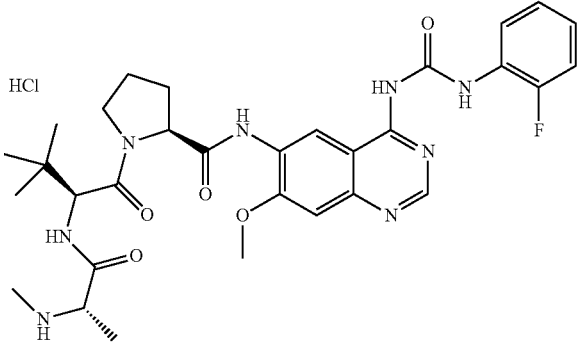 [SMILES: CN[C@@H](C)C(=O)N[C@H](C(=O)N1CCC[C@H]1C(=O)Nc1cc2c(NC(=O)Nc3ccccc3F)ncnc2cc1OC)C(C)(C)C ; Cl] |
| 90 | (S)-1-((S)-3,3-dimethyl-((S)-2-(methylamino)propanamido)-butanoyl)-N-(7-methoxy-4-((4-morpholinophenyl)amino)quinazolin-6-yl)pyrrolidine-2-carboxamide hydrochloride | 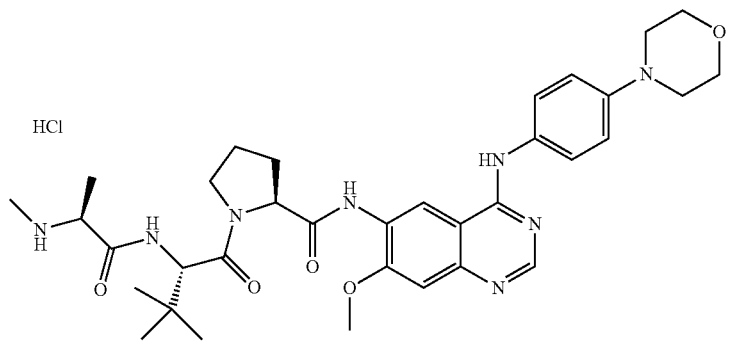 [SMILES: CN[C@@H](C)C(=O)N[C@H](C(=O)N1CCC[C@H]1C(=O)Nc1cc2c(Nc3ccc(N4CCOCC4)cc3)ncnc2cc1OC)C(C)(C)C ; Cl] |
| 91 | (S)-1-((S)-3,3-dimethyl-2-((S)-2-(methylamino)propanamide)-butanoyl)-N-(7-methoxy-4-((4-(2-propyn-1-yloxy)phenyl)-amino)quinazolin-6-yl)-pyrrolidine-2-carboxamide hydrochloride | 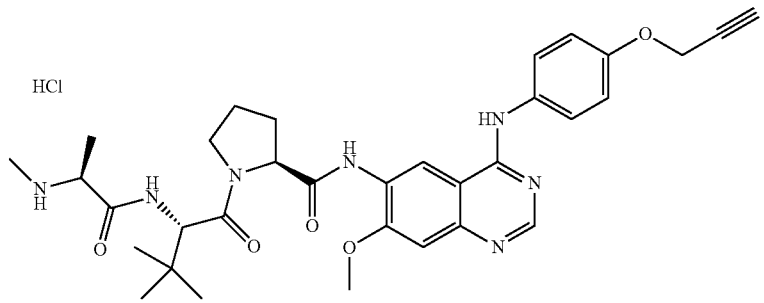 [SMILES: C#CCOc1ccc(Nc2ncnc3cc(OC)c(NC(=O)[C@@H]4CCCN4C(=O)[C@@H](NC(=O)[C@H](C)NC)C(C)(C)C)cc23)cc1 ; Cl] |
| 92 | (S)-N-(4-((3-chloro-4-(4-(cyclopropylmethyl)piperazin-1-yl)phenyl)amino)-7-methoxyquinazolin-6-yl)-1-((S)-3,3-dimethyl-2-((S)-2-(methylamino)propanamido)butanoyl)-pyrrolidine-2-carboxamide | 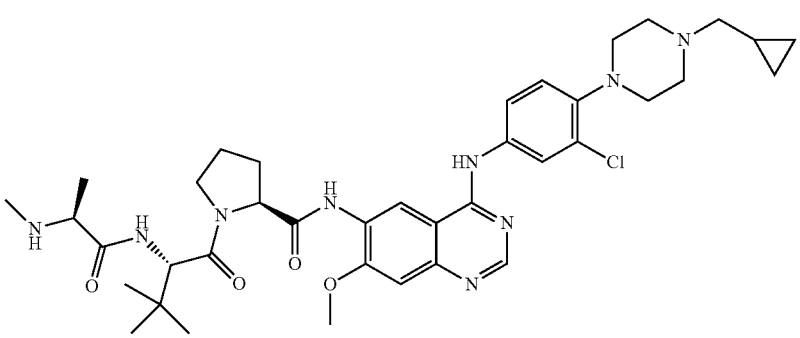 [SMILES: CN[C@@H](C)C(=O)N[C@H](C(=O)N1CCC[C@H]1C(=O)Nc1cc2c(Nc3ccc(N4CCN(CC5CC5)CC4)c(Cl)c3)ncnc2cc1OC)C(C)(C)C] |

TABLE-continued

| Example | Name | Formula |
|---|---|---|
| 93 | (S)-1-((S)-3,3-dimethyl-2-((S)-2-(methylamino)propanamide)-butanoyl)-N-(7-methoxy-4-((2-methyl-4-oxo-4H-chromen-7-yl)amino)quinazolin-6-yl)pyrrolidine-2-carboxamide hydrochloride | 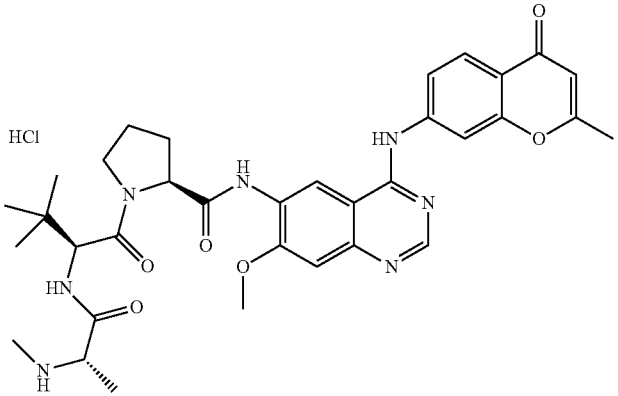 [SMILES: CN[C@@H](C)C(=O)N[C@H](C(=O)N1CCC[C@H]1C(=O)Nc1cc2c(Nc3ccc4c(=O)cc(C)oc4c3)ncnc2cc1OC)C(C)(C)C ; Cl] |
| 94 | (S)-1-((S)-3,3-dimethyl-2-((S)-2-(methylamino)propanamide)butanoyl)-N-(7-methoxy-4-((2-oxoindolin-5-yl)-amino)quinazolin-6-yl)pyrrolidine-2-carboxamide hydrochloride | 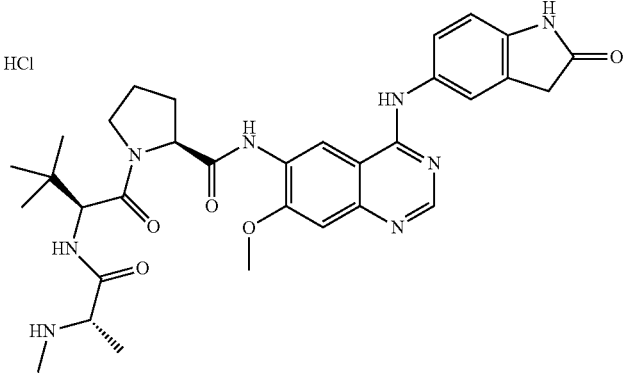 [SMILES: Cl ; CN[C@@H](C)C(=O)N[C@H](C(=O)N1CCC[C@H]1C(=O)Nc1cc2c(Nc3ccc4c(c3)CC(=O)N4)ncnc2cc1OC)C(C)(C)C] |
| 95 | (S)-N-(4-((3-chloro-4-morpholinophenyl)-amino)-7-methoxyquinazolin-6-yl)-1-((S)-3,3-dimethyl-2-((S)-2-(methylamino)propanamido)butanoyl)-pyrrolidine-2-carboxamide | 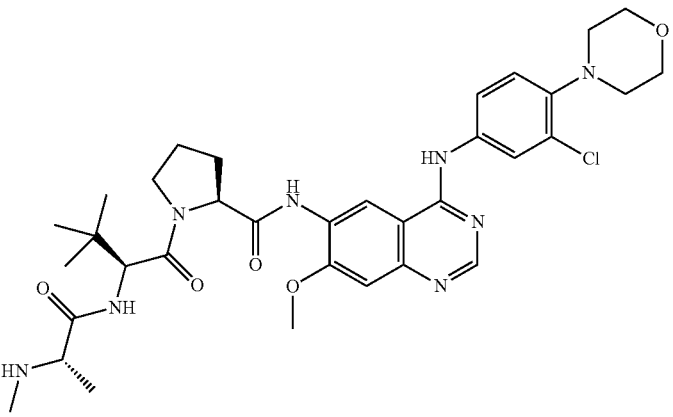 [SMILES: CN[C@@H](C)C(=O)N[C@H](C(=O)N1CCC[C@H]1C(=O)Nc1cc2c(Nc3ccc(N4CCOCC4)c(Cl)c3)ncnc2cc1OC)C(C)(C)C] |
| 96 | (S)-N-(4-((3-chloro-4-(piperidin-1-yl)phenyl)amino)-7-methoxyquinazolin-6-yl)-1-((S)-3,3-dimethyl-2-((S)-2-(methylamino)-propanamido)butanoyl)pyrrolidine-2-carboxamide hydrochloride | 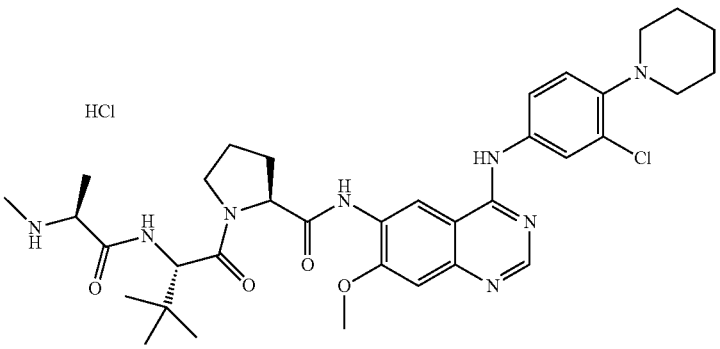 [SMILES: CN[C@@H](C)C(=O)N[C@H](C(=O)N1CCC[C@H]1C(=O)Nc1cc2c(Nc3ccc(N4CCCCC4)c(Cl)c3)ncnc2cc1OC)C(C)(C)C ; Cl] |

| Example | Name | Formula |
|---|---|---|
| 97 | (S)-N-(4-((3-chloro-4-(4-isopropylpiperazin-1-yl)-phenyl)amino)-7-methoxyquinazolin-6-yl)-1-((S)-3,3-dimethyl-2-((S)-2-(methylamino)propanamido)butanoyl)-pyrrolidine-2-carboxamide hydrochloride | 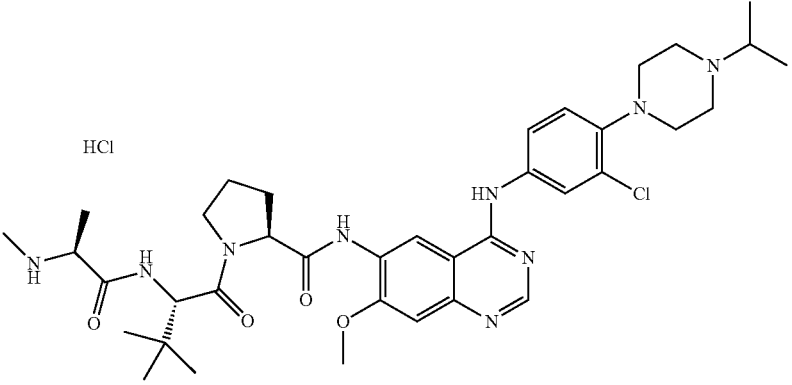 [SMILES: CN[C@@H](C)C(=O)N[C@H](C(=O)N1CCC[C@H]1C(=O)Nc1cc2c(Nc3ccc(N4CCN(C(C)C)CC4)c(Cl)c3)ncnc2cc1OC)C(C)(C)C ; Cl] |
| 98 | (S)-N-(4-((3-chloro-4-(4-propyl-1-yl)phenyl)amino)-7-methoxy-quinazolin-6-yl)-1-((S)-3,3-dimethyl-2-((S)-2-(methylamino)propanamido)-butanoyl)pyrrolidine-2-carboxamide hydrochloride | 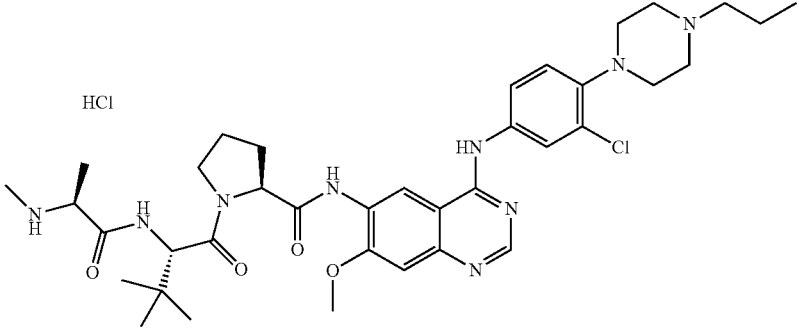 [SMILES: CCCN1CCN(c2ccc(Nc3ncnc4cc(OC)c(NC(=O)[C@@H]5CCCN5C(=O)[C@@H](NC(=O)[C@H](C)NC)C(C)(C)C)cc34)cc2Cl)CC1 ; Cl] |
| 99 | (S)-N-(4-((3-chloro-4-(diethylamino)phenyl)amino)-7-methoxyquinazolin-6-yl)-1-((S)-3,3-dimethyl-2-((S)-2-(methylamino)-propanamido)butanoyl)pyrrolidine-2-carboxamide hydrochloride | 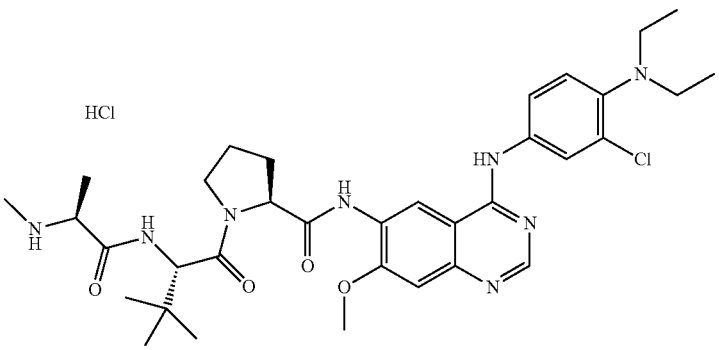 [SMILES: CCN(CC)c1ccc(Nc2ncnc3cc(OC)c(NC(=O)[C@@H]4CCCN4C(=O)[C@@H](NC(=O)[C@H](C)NC)C(C)(C)C)cc23)cc1Cl ; Cl] |
| 100 | (S)-N-(4-((4-(4-(cyclopropylmethyl)-piperazin-1-yl)-3-fluorophenyl)amino)-7-methoxyquinazolin-6-yl)-1-((S)-3,3-dimethyl-2-((S)-2-(methylamino)propanamido)-butanoyl)pyrrolizine-2-carboxamide hydrochloride | 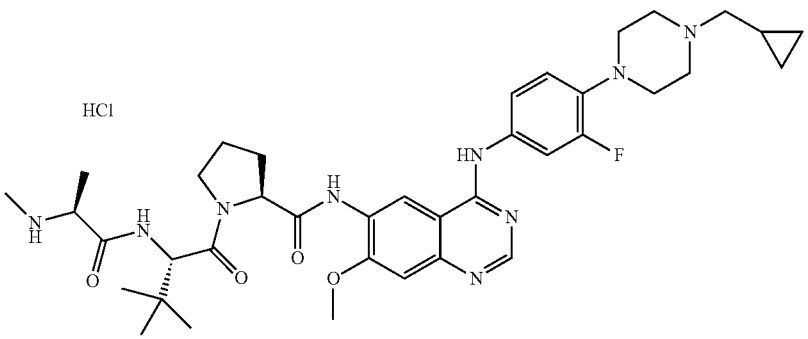 [SMILES: CN[C@@H](C)C(=O)N[C@H](C(=O)N1CCC[C@H]1C(=O)Nc1cc2c(Nc3ccc(N4CCN(CC5CC5)CC4)c(F)c3)ncnc2cc1OC)C(C)(C)C ; Cl] |

TABLE-continued

| Example | Name | Formula |
|---|---|---|
| 101 | (S)-N-(4-((3,5-dichloro-4-(pyridin-2-ylmethoxy)phenyl)amino)-7-methoxyquinazolin-6-yl)-1-((S)-3,3-dimethyl-2-((S)-2-(methylamino)propanamido)-butanoyl)pyrrolidine-2-carboxamide hydrochloride | 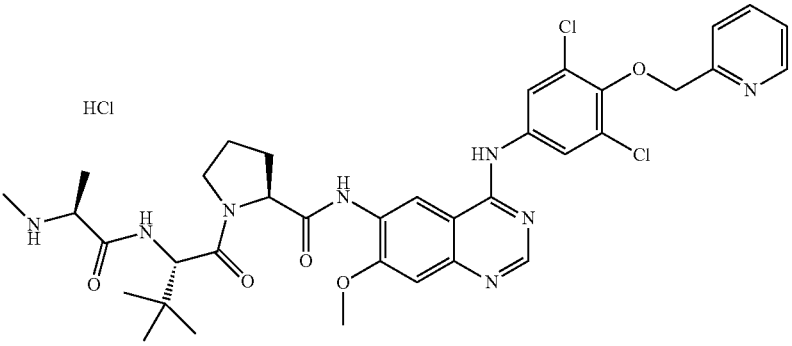 [SMILES: CN[C@@H](C)C(=O)N[C@H](C(=O)N1CCC[C@H]1C(=O)Nc1cc2c(Nc3cc(Cl)c(OCc4ccccn4)c(Cl)c3)ncnc2cc1OC)C(C)(C)C ; Cl] HCl |
| 102 | (S)-N-(4-((3-chloro-4-(pyridin-2-ylmethoxy)phenyl)amino)-7-methoxyquinazolin-6-yl)-1-((S)-3,3-dimethyl-2-((S)-2-(methylamino)propanamido)butanoyl)-pyrrolidine-2-carboxamide hydrochloride | 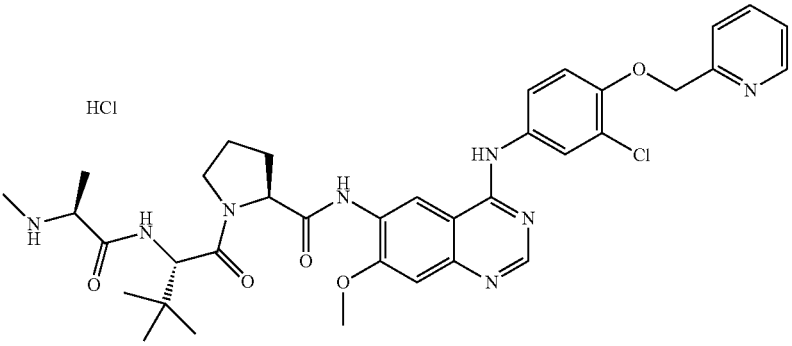 [SMILES: CN[C@@H](C)C(=O)N[C@H](C(=O)N1CCC[C@H]1C(=O)Nc1cc2c(Nc3ccc(OCc4ccccn4)c(Cl)c3)ncnc2cc1OC)C(C)(C)C ; Cl] HCl |
| 103 | (S)-N-(4-((4-([1,4'-bipiperidine]-1'-yl)phenyl)amino)-7-methoxyquinazolin-6-yl)-1-((S)-3,3-dimethyl-2-((S)-2-(methylamino)propanamido)-butanoyl)pyrrolidine-2-carboxamide hydrochloride | 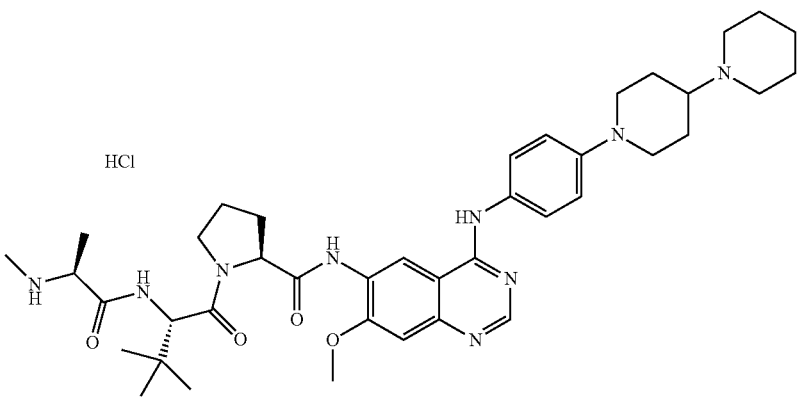 [SMILES: CN[C@@H](C)C(=O)N[C@H](C(=O)N1CCC[C@H]1C(=O)Nc1cc2c(Nc3ccc(N4CCC(N5CCCCC5)CC4)cc3)ncnc2cc1OC)C(C)(C)C ; Cl] HCl |
| 104 | (S)-1-((S)-3,3-dimethyl-2-((S)-2-(methylamino)propanamido)-butanoyl)-N-(7-methoxy-4-((4-(piperidin-1-ylmethyl)phenyl)amino)-quinazolin-6-yl)pyrrolidine-2-carboxamide hydrochloride | 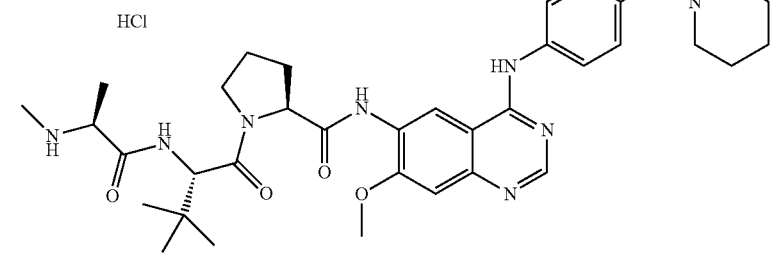 HCl |

TABLE-continued

| Example | Name | Formula |
|---|---|---|
| 105 | (S)-1-((S)-3,3-dimethyl-2-((S)-2-(methylamino)propanamido)-butanoyl)-N-(7-methoxy-4-((4-(4-(4-methylpiperazin-1-yl)piperidin-1-yl)phenyl)amino)quinazolin-6-yl)-pyrrolidine-2-carboxamide hydrochloride | 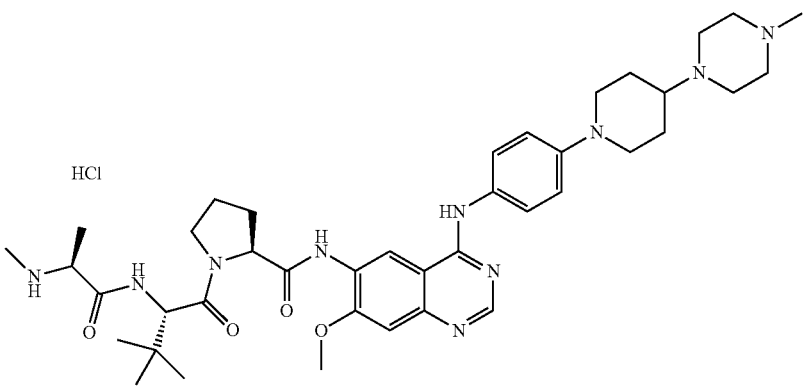 |
| 106 | (S)-1-((S)-3,3-dimethyl-2-((S)-2-(methylamino)propanamido)-butanoyl)-N-(7-methoxy-4-((4-(1-methylpiperidin-4-yl)phenyl)-amino)quinazolin-6-yl)pyrrolidine-2-carboxamide hydrochloride | 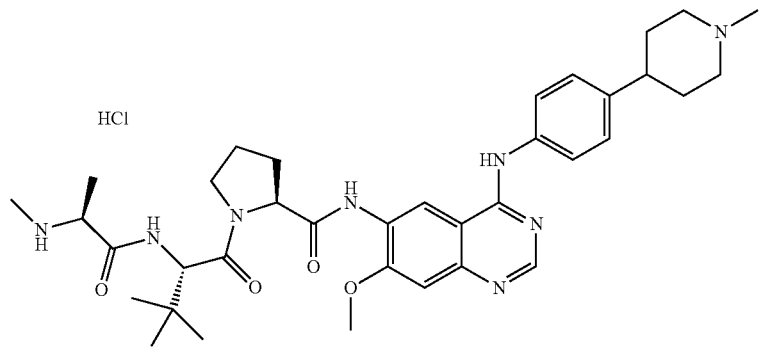 |
| 107 | (S)-1-((S)-3,3-dimethyl-2-((S)-2-(methylamino)propanamido)-butanoyl)-N-(7-methoxy-4-((4-(4-methylpiperidin-1-yl)cyclohexyl)amino)-quinazolin-6-yl)-pyrrolidine-2-carboxamide hydrochloride | 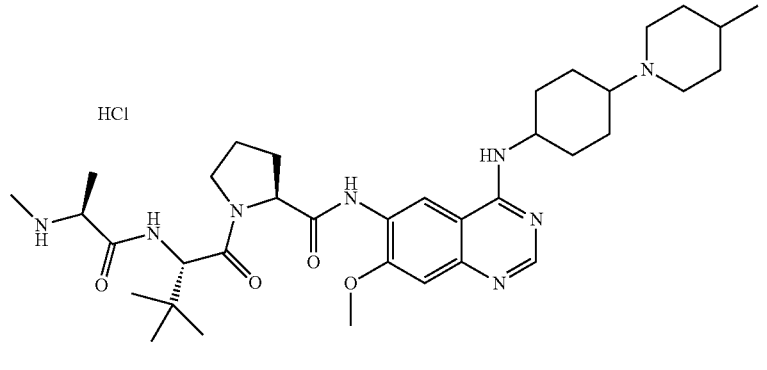 |
| 108 | (S)-1-((S)-3,3-dimethyl-2-((S)-2-(methylamino)propanamido)-butanoyl)-N-(7-methoxy-4-((4-((4-methylpiperazin-1-yl)sulfonyl)phenyl)amino)-quinazolin-6-yl)pyrrolidine-2-carboxamide hydrochloride | 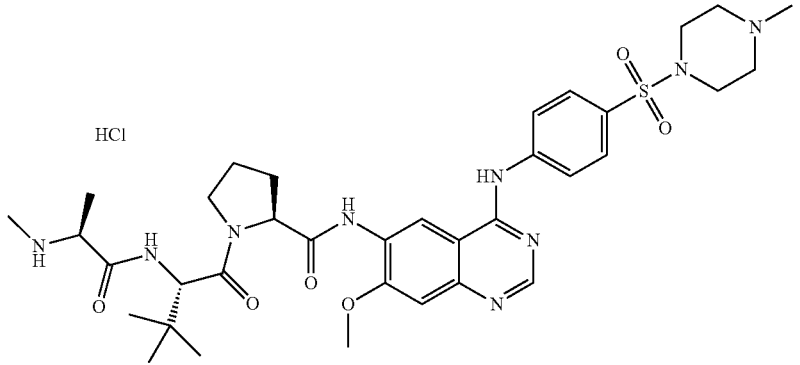 |

| Example | Name | Formula |
|---|---|---|
| 109 | (2S)-1-((S)-3,3-dimethyl-2-((S)-2-(methylamino)propanamido)-butanoyl)-N-(7-methoxy-4-((4-(1-methylpiperidin-3-yl)phenyl)amino)quinazolin-6-yl)-pyrrolidine-2-carboxamide hydrochloride | 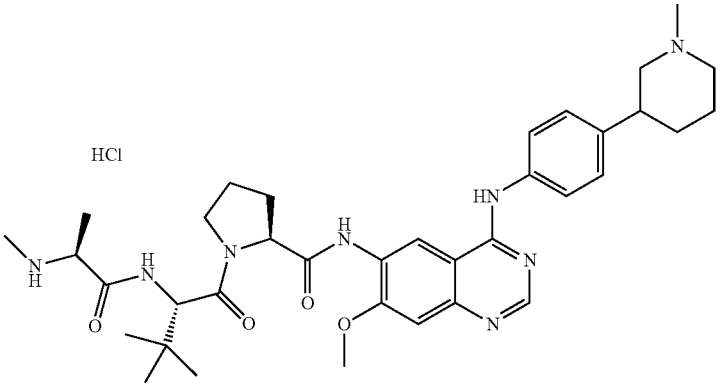 [SMILES: CN[C@@H](C)C(=O)N[C@H](C(=O)N1CCC[C@H]1C(=O)Nc1cc2c(Nc3ccc(C4CCCN(C)C4)cc3)ncnc2cc1OC)C(C)(C)C ; Cl] |
| 110 | (S)-1-((S)-3,3-dimethyl-2-((S)-2-(methylamino)propanamido)-butanoyl)-N-(7-methoxy-4-((4-(4-(1-methylpiperidin-4-yl)-piperazin-1-yl)phenyl)amino)-quinazolin-6-yl)pyrrolizine-2-carboxamide hydrochloride | 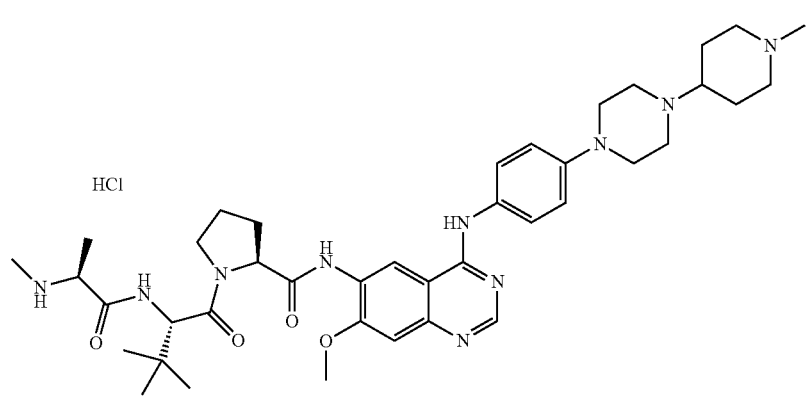 |
| 111 | (S)-N-(4-((4-((1H-imidazol-1-yl)methyl)phenyl)amino)-7-methoxyquinazolin-6-yl)-1-((S)-3,3-dimethyl-2-((S)-2-(methylamino)propanamido)-butanoyl)pyrrolidine-2-carboxamide hydrochloride | 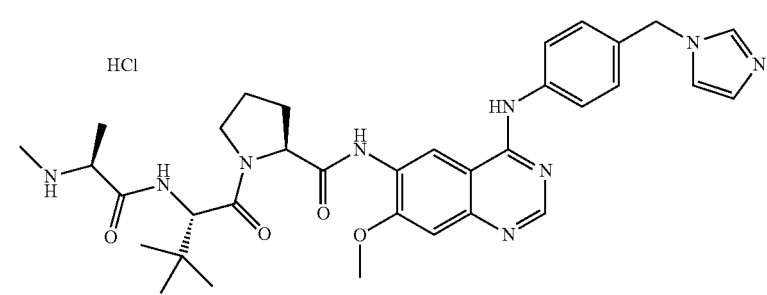 [SMILES: CN[C@@H](C)C(=O)N[C@H](C(=O)N1CCC[C@H]1C(=O)Nc1cc2c(Nc3ccc(Cn4ccnc4)cc3)ncnc2cc1OC)C(C)(C)C ; Cl] |
| 112 | (S)-1-((S)-3,3-dimethyl-2-((S)-2-(methylamino)propanamido)-butanoyl)-N-(4-((3-fluoro-4-(4-methylpiperazin-1-yl)-phenyl)amino)-7-methoxyquinazolin-6-yl)pyrrolidine-2-carboxamide | 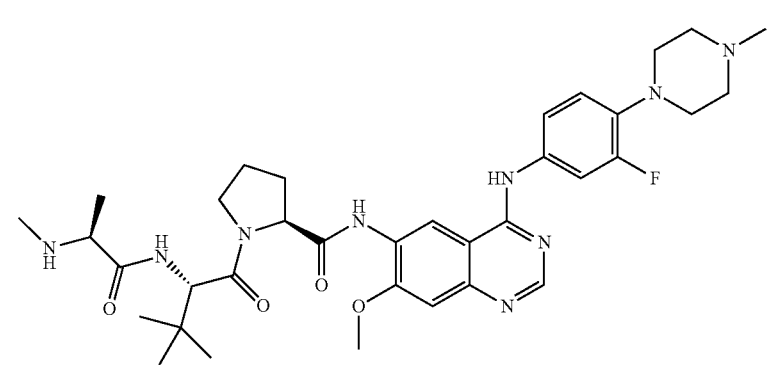 |

TABLE-continued

| Example | Name | Formula |
|---|---|---|
| 113 | (S)-N-(4-((3-chloro-4-(pyrrolidine-1-yl)phenyl)amino)-7-methoxyquinazolin-6-yl)-1-((S)-3,3-dimethyl-2-((S)-2-(methylamino)propanamido)-butanoyl)pyrrolidine-2-carboxamide | |

The compounds prepared from Examples were tested for biological assays as follows.

Experimental Example 1

Evaluation of Caspase Activity

MDA-MB-231 breast cancer cells (ATCC #HTB-26) were plated in 96-well plates at a density of $1.0$~$1.5 \times 10^4$ cells/well. After 24 hours, the cells were treated with test compounds at a concentration of 0 μM, 0.5 μM, 1 μM and 5 μM, respectively, for 12 hours to caspase 3/7 and for 16 hours to caspase 9. Then, media were removed and the cells were washed two times with PBS at 4° C. The cells were treated with a solution of the analysis samples and media (1:1) in an amount of 140 μL/well using Caspase-Glo™ 9 Assay Kit (Cat#. G8210; Promega, USA) and Caspase-Glo™ 3/7 Assay Kit (Cat#. G8090; Promega, USA). After the cells were incubated at 37° C. for 2 hours, luminescence was measured using Infinite™ M1000 multi reader (Tecan).

The measurement values of representative compounds are shown in Table 2, and IAP antagonist (Abbott) was used as a control.

The values were represented as "*" for six fold or more, "" for 4 fold to below 6 fold, and "*" for 1 fold to below 4 fold, as compared to that of untreated, normal MDA-MB-231 breast cancer cell lines.

TABLE 2

| Example | Caspase-3 | Caspase-9 |
|---|---|---|
| Control | ** | ** |
| 1 | *** | *** |
| 2 | ** | * |
| 7 | *** | *** |
| 8 | *** | *** |
| 9 | *** | *** |
| 10 | *** | *** |
| 11 | *** | *** |
| 15 | *** | *** |
| 17 | *** | *** |
| 18 | *** | *** |
| 19 | *** | *** |

As shown in Table 2, the compounds of the present invention increased the activity of caspase, which plays key effector roles in apoptosis of cancer cell lines, to induce apoptosis.

Experimental Example 2

Evaluation of Binding Affinity

In order to analyze the binding affinity with BIR-3 domain, XIAP BIR pre-diluted by 1.25 μM was placed into a black, round-bottom 96-well plate at 5 L/well, and 4F (AbuRPF-K (5-Fam)-NH$_2$) pre-diluted by 0.0625 μM was added thereto at 10 μL/well under a dark condition. At the time, XIAP BIR is a 241-356$^{th}$ amino acid residue of human XIAP protein, which was prepared by transforming E. coli BL21 (DE3) cells with a recombinant vector prepared from pET28a vector (Novagen) using standard DNA cloning process and PCR method (see Sambrook & Russell., Molecular cloning., Chapter 1. Third edition).

Specifically, pET28a (+) vector (Novagen) was used for introduction of a gene expressing a XIAP BIR3 protein. XIAR BIR3 was amplified by PCR using a reaction mixture comprising 1 μL of K562 (human blood lympoblast-like leukemia) cDNA as a template, 1.5 mM MgCl$_2$, 0.2 mM dNPTs, 0.4 mM sense and antisense PCR primers (SEQ ID NOs. 1 and 2) and 2.0 unit tag polymerase (Elpis biotech, Korea). The PCR was carried out under the following conditions: initial denaturation at 94° C. for five minutes; 35 cycles of denaturation at 94° C. for 30 seconds, annealing at 52° C. for 30 seconds and extension at 72° C. for 30 seconds; and final elongation at 72° C. for 7 minutes. The sequences of primer used in the experiment are represented in Table 3.

TABLE 3

| | Sequence |
|---|---|
| Sense primer (SEQ ID NO: 1) | 5'-CGC GGA TCC TCT GAT GCT GTG AGT TCT GA-3' |
| Antisense primer (SEQ ID NO: 2) | 5'-GAG CCT CGA GCT AAG TAG TTC TTA CCA GAC-3' |

The DNAs of XIAP BIR3 domains amplified above was inserted into pET28a (+) vector (Novagen), and E. coli BL21 (DE3) cells were transformed with said vector, and cultured. When the culture reaches an O.D of 0.6, 0.1 mM IPTG was added to overexpress a human XIAP BIR3 protein. The amino acid sequence of the overexpressed XIAP BIR3 protein is represented in SEQ ID NO: 3, which has six histidines (His-tag) bound to the terminus.

Subsequently, the cells containing said overexpressed proteins were subjected to ultrasonication, and centrifuged to obtain a supernatant. The supernatant was reacted with affinity beads which can specifically bind to His-Tag to isolate the desired protein from other proteins. XIAP BIR proteins were eluted from the affinity beads using 20 mM Tris, 10 mM NaCl (pH8.0), 100 mM imidazole buffer.

A binding assay buffer consisting of 100 mM calcium phosphate (pH 7.5), 100 μg/ml bovine γ-globulin and 0.02% sodium azide was added thereto at 105 μL/well, followed by a reaction at room temperature for 15 min. Subsequently, a positive control RPF-NH$_2$ (alanine-alginine-proline-phenylalanine-NH$_2$) and test compounds serially diluted to a concentration of 0.01 to 1,000 μM were added at 5 μL/well. In case of 0% and 100% inhibitory controls, DMSO was used instead. After reaction for 3 hours under a dark condition, Fluorescense Polarization values were measured at excitation wavelength 485 nm and emission wavelength 530 nm by using Infinite™ M1000 multi reader (Tecan). IC$_{50}$ values of test compounds and Kd values of 4F (ARPF-NH$_2$) were obtained from above values, and Ki values of test compounds calculated therefrom are shown in Table 4. The Ki values were represented as "*" for below 100 nM, "" for 100 nM to below 1,000 nM, and "*" for 1,000 nM or more.

TABLE 4

| Example | Binding affinity (IC$_{50}$) |
|---|---|
| Control | ** |
| 1 | ** |
| 2 | * |
| 3 | * |
| 4 | * |
| 5 | * |
| 6 | * |
| 7 | * |
| 8 | ** |
| 9 | ** |
| 10 | ** |
| 11 | ** |
| 12 | ** |
| 13 | * |
| 14 | ** |
| 15 | ** |
| 16 | * |
| 17 | ** |
| 18 | ** |
| 19 | ** |
| 20 | ** |
| 21 | ** |
| 22 | ** |
| 23 | ** |
| 24 | ** |
| 25 | * |
| 26 | * |
| 27 | * |
| 28 | ** |
| 29 | ** |
| 30 | ** |
| 31 | ** |
| 32 | ** |
| 33 | ** |
| 34 | ** |
| 35 | ** |
| 36 | ** |
| 37 | * |
| 38 | ** |
| 39 | ** |
| 40 | ** |
| 41 | ** |
| 42 | ** |
| 43 | * |
| 44 | * |

As shown in Table 4, the compounds of the present invention showed high affinities to BIR3 domains of IAP, an inhibitor of apoptosis protein, indicating its selective mechanism.

Experimental Example 3

Evaluation of Inhibition on Cell Growth (In-Vitro)

MDA-MB-231 breast cancer cell lines (ATCC #HTB-26) and BxPC-3 pancreas cancer cell lines (ATCC #CRL 1687), which have been reported to express XIAP, were obtained from ATCC (American type culture collection; Rockville, Md.). MDA-MB-231 cell lines were incubated in L-15 medium supplemented with 10% FBS and 1% penicillin/streptomycin (Gibco BRL) at a T-75 cm$^2$ growth flask. In addition, BxPC-3 cell lines were incubated in RPMI medium supplemented with 10% FBS and 1% penicillin/streptomycin. For experiments of toxicity to normal cells, fibroblasts Hs27 (ATCC #CRL 1634) and Balb/c3t3 (ATCC #CCL 163) were used. The various cell lines were transferred into 96-well plates at a density of 3,000~5,000 cells/100 μL, and cultured for 24 hours under conditions of 37° C., 5% CO$_2$, 95% air, and 100% relative humidity (MDA-MB-231 cells were cultured under atmospheric conditions). The cells were treated with 10 μM~0.1 nM of test compounds, and MDA-MB-231, BxPC-3, and normal cell lines were cultured for 120, 96, and 72 hours, respectively.

Cell viabilities of MDA-MB-231 cell lines were measured at an absorbance of 490 nm using CellTiter 96™ AQueous One Solution Cell proliferation Assay (MTS, Promega), and cell viabilities of BxPC-3 and normal cell lines were measured by fixing cells with 10% TCA (trichloroacetic acid), staining with SRB (sulforhodamine B), and measuring at 540 nm. From the values, GI$_{50}$ values in which test compounds reduce the growth of cancer cells by 50% were calculated. The growth rates of cancer cells were calculated from following Equation 1 or 2.

$$[(Ti-Tz)/(C-Tz)]\times 100 \text{ (for } Ti>=Tz)$$ [Equation 1]

$$[(Ti-Tz)/Tz]\times 100 \text{ (for } Ti<Tz)$$ [Equation 2]

In Equations 1 and 2, Tz refers to a density of untreated cells, which is an absorbance in 0% cell growth groups. C refers to a density of cells cultured by adding only medium, and Ti refers to a density of cells treated with test compounds.

GI$_{50}$ value is the concentration of a test compound when the value of Equation 1 is 50, which indicates the concentration of test compound required to inhibit the cancer cells by 50%. On each measurement, test compounds were compared with a control.

The activity value of each compound (GI$_{50}$ value) was shown in Table 5, and an IAP antagonist was used as a control.

In the activity measurement on MDA-MB-231 breast cancer cell lines, the values were represented as "*" for 100 nM or less, "" for over 100 nM to below 1,000 nM, and "*" for 1,000 nM or more. In the measurement on normal cell lines, Balb/C and Hs27, the values were represented as "+++" for 10,000 nM or more, "++" for over 5,000 nM to below 10,000 nM, and "+" for 5,000 nM or less.

TABLE 5

| Example | MDA-MB-231 | BalB/C | Hs27 |
|---|---|---|---|
| Control | ** | +++ | +++ |
| 1 | *** | +++ | +++ |
| 2 | ** | +++ | +++ |
| 3 | ** | +++ | +++ |
| 4 | ** | +++ | +++ |
| 5 | ** | +++ | +++ |
| 6 | ** | +++ | +++ |

TABLE 5-continued

| Example | MDA-MB-231 | BalB/C | Hs27 |
|---|---|---|---|
| 7 | *** | +++ | +++ |
| 8 | *** | +++ | +++ |
| 9 | *** | +++ | +++ |
| 10 | *** | +++ | +++ |
| 11 | *** | +++ | +++ |
| 12 | * | +++ | +++ |
| 13 | * | +++ | +++ |
| 14 | *** | +++ | +++ |
| 15 | *** | +++ | +++ |
| 16 | ** | +++ | +++ |
| 17 | *** | +++ | +++ |
| 18 | *** | +++ | +++ |
| 19 | *** | +++ | +++ |
| 20 | ** | +++ | +++ |
| 21 | *** | +++ | +++ |
| 22 | *** | +++ | +++ |
| 23 | *** | +++ | +++ |
| 24 | *** | +++ | +++ |
| 25 | ** | +++ | +++ |
| 26 | * | +++ | +++ |
| 27 | *** | +++ | +++ |
| 28 | *** | +++ | +++ |
| 29 | *** | +++ | +++ |
| 30 | *** | +++ | +++ |
| 31 | *** | +++ | +++ |
| 32 | *** | +++ | +++ |
| 33 | *** | +++ | +++ |
| 34 | *** | +++ | +++ |
| 35 | *** | +++ | +++ |
| 36 | ** | +++ | +++ |
| 37 | *** | +++ | +++ |
| 38 | *** | +++ | +++ |
| 39 | *** | +++ | +++ |
| 40 | *** | +++ | +++ |
| 41 | *** | +++ | +++ |
| 42 | *** | +++ | +++ |
| 43 | *** | +++ | +++ |
| 44 | *** | +++ | +++ |
| 45 | *** | +++ | +++ |
| 46 | *** | +++ | +++ |
| 47 | *** | +++ | +++ |
| 48 | *** | +++ | +++ |
| 49 | *** | +++ | +++ |
| 50 | *** | +++ | +++ |
| 51 | *** | +++ | +++ |
| 52 | *** | +++ | +++ |
| 53 | *** | +++ | +++ |
| 54 | *** | +++ | +++ |
| 55 | *** | +++ | +++ |
| 56 | *** | +++ | +++ |
| 57 | *** | +++ | +++ |
| 58 | *** | +++ | +++ |
| 59 | *** | +++ | +++ |
| 60 | ** | +++ | +++ |
| 61 | * | +++ | +++ |
| 62 | ** | +++ | +++ |
| 63 | *** | +++ | +++ |
| 64 | *** | +++ | +++ |
| 65 | *** | +++ | +++ |
| 66 | *** | +++ | +++ |
| 67 | *** | +++ | +++ |
| 68 | *** | +++ | +++ |
| 69 | *** | +++ | +++ |
| 70 | *** | +++ | +++ |
| 71 | *** | +++ | +++ |
| 72 | *** | +++ | +++ |
| 73 | *** | +++ | +++ |
| 74 | *** | +++ | +++ |
| 75 | *** | +++ | +++ |
| 76 | *** | +++ | +++ |
| 77 | *** | − | +++ |
| 78 | *** | − | +++ |
| 79 | *** | − | +++ |
| 80 | *** | − | +++ |
| 81 | *** | − | +++ |
| 82 | *** | − | +++ |
| 83 | ** | − | +++ |
| 84 | ** | − | +++ |
| 85 | *** | − | +++ |
| 86 | *** | − | +++ |
| 87 | *** | − | +++ |
| 88 | *** | − | +++ |
| 89 | *** | − | +++ |
| 90 | *** | − | +++ |
| 91 | *** | − | +++ |
| 92 | *** | − | +++ |
| 93 | *** | − | +++ |
| 94 | ** | − | +++ |
| 95 | *** | − | +++ |
| 96 | *** | − | +++ |
| 97 | *** | − | +++ |
| 98 | *** | − | +++ |
| 99 | *** | − | +++ |
| 100 | *** | − | +++ |
| 101 | *** | − | +++ |
| 102 | *** | − | +++ |
| 103 | *** | − | +++ |
| 104 | *** | − | +++ |
| 105 | *** | − | +++ |
| 106 | *** | − | +++ |
| 107 | ** | − | +++ |
| 108 | *** | − | +++ |
| 109 | *** | − | +++ |
| 110 | *** | − | +++ |
| 111 | ** | − | +++ |
| 112 | *** | − | +++ |
| 113 | *** | − | +++ |

As shown in Table 5, the compounds of formula (I) of the present invention inhibited more significantly the growth of MDA-MB-231 cell lines in which IAPs are overexpressed, even at a low concentration.

In contrast, the compounds of the present invention did not inhibit the growth of a mouse normal cell line Balb/C and human normal cell line Hs27, even at a high concentration, which indicates that the compounds of the present invention has a high selectivity to tumor and aberrant cell lines.

As evidenced above, the compounds of the present invention selectively act on IAPs to show no adverse influence on normal cells and to allow normal apoptotic mechanism in tumor and aberrant cells. Thus, these compounds may be used in the prevention or treatment of a cancer, inflammation, autoimmune diseases, and neurodegenerative disorders, alone or in combination, while exerting no adverse effects.

Although the present invention has been described by way of a detailed description in which various embodiments and aspects of the invention have been described, it will be seen by one skilled in the art that the full scope of this invention is not limited to the examples presented herein. Therefore, the substantial scope of the present invention will be defined by the accompanying claims and equivalents thereof.

What is claimed is:

1. A compound selected from the group consisting of a quinoline or quinazoline derivative of Formula (I), and a pharmaceutically acceptable salt, an isomer, a hydrate, and a solvate thereof:

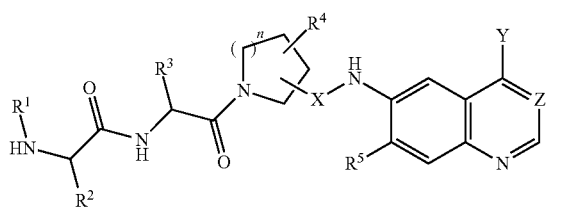

(I)

wherein,

Z is CH or N;

X is C(=O) or CH$_2$;

Y is hydrogen, —NR$^6$R$^7$, —NR$^6$C(=O)R$^7$, or —NR$^6$C(=O)NR$^6$R$^7$;

n is an integer ranging from 0 to 3;

R$^1$ is hydrogen, C$_{1-6}$alkyl, C$_{1-6}$alkanoyl, C$_{2-6}$alkenoyl, or C$_{2-6}$alkynoyl;

R$^2$ is hydrogen or C$_{1-3}$alkyl;

R$^3$ is hydrogen, C$_{1-6}$alkyl, C$_{3-6}$cycloalkyl, or C$_{3-6}$alkynyloxyC$_{1-4}$alkyl;

R$^4$ and R$^5$ are each independently hydrogen, —O(CH$_2$)$_m$—C$_{1-6}$alkyl, —O(CH$_2$)$_m$—C$_{3-6}$cycloalkyl, —O(CH$_2$)$_m$—C$_{3-6}$heterocycloalkyl, —O(CH$_2$)$_m$—

$C_{5-10}$aryl, —O(CH$_2$)$_m$—C$_{5-10}$heteroaryl or —O(CH$_2$)$_m$—C$_{1-3}$alkoxy, in which m is an integer ranging from 0 to 3;

$R^6$ is hydrogen or $C_{1-6}$alkyl; and $R^7$ is hydrogen, $C_{1-8}$alkyl, —(CH$_2$)$_l$—C$_{3-6}$cycloalkyl, —(CH$_2$)$_l$—C$_{3-6}$heterocycloalkyl, —(CH$_2$)$_l$—C$_{5-10}$aryl or —(CH$_2$)$_l$—C$_{5-10}$heteroaryl, in which l is an integer ranging from 0 to 3; in which:

said $R^6$ and $R^7$ are optionally linked together to form a ring structure; and said $R^7$ is optionally substituted with one or more substituents selected from the group consisting of halogen, —CF$_3$, —NO$_2$, —CN, $C_{1-8}$alkyl, —(CH$_2$)$_p$NR$^8$R$^9$, —(CH$_2$)$_p$OR$^{10}$, —(CH$_2$)$_p$C(=O)R$^{11}$, —(CH$_2$)$_p$C(=O)OR$^{10}$, —(CH$_2$)$_p$C(=O)NR$^8$R$^9$, —(CH$_2$)$_p$NR$^8$C(=O)R$^{11}$, —(CH$_2$)$_p$SR$^{12}$, —(CH$_2$)$_p$S(=O)R$^{11}$, —(CH$_2$)$_p$S(=O)$_2$R$^{11}$, and —(CH$_2$)$_p$—C$_{3-6}$cycloalkyl, —(CH$_2$)$_p$—C$_{3-6}$heterocycloalkyl, —(CH$_2$)$_p$—C$_{5-10}$aryl and —(CH$_2$)$_p$—C$_{5-10}$heteroaryl, in which p is an integer ranging from 0 to 3; in which:

said $R^8$, $R^9$, $R^{10}$, $R^{11}$ and $R^{12}$ are each independently halogen, —CF$_3$, —NO$_2$, —CN, $C_{1-6}$alkyl, —(CH$_2$)$_q$—C$_{3-6}$cycloalkyl, —(CH$_2$)$_q$—C$_{3-6}$heterocycloalkyl, —(CH$_2$)$_q$—C$_{2-4}$alkenyl, —(CH$_2$)$_q$—C$_{2-4}$alkynyl, —(CH$_2$)$_q$—C$_{5-10}$aryl or —(CH$_2$)$_q$—C$_{5-10}$heteroaryl, in which q is an integer ranging from 0 to 3; and said $R^8$ and $R^9$ are optionally linked together to form a ring structure.

2. The compound of claim 1, wherein Z is N.

3. The compound of claim 1, wherein X is C(=O).

4. The compound of claim 1, wherein $R^1$ is hydrogen or methyl.

5. The compound of claim 1, wherein $R^2$ is methyl.

6. The compound of claim 1, wherein $R^3$ is t-butyl, cyclohexyl or propazyloxyethyl.

7. The compound of claim 1, wherein $R^4$ is hydrogen or benzyloxy.

8. The compound of claim 1, wherein $R^5$ is hydrogen, methoxy, 2-methoxyethoxy or 3-tetrahydrofuranyloxy.

9. The compound of claim 1, wherein n is 1.

10. The compound of claim 1, wherein Y is selected from the group consisting of hydrogen, amine, 4-bromo-2-fluoroaniline, 3-chloro-2-fluoroaniline, 3,4-dichloro-2-fluoroaniline, 5-chlorobenzo-[1,3]dioxol-4-amine, 2,4-difluoro-3-chloroaniline, 4-chloro-3-fluoroaminobenzene, phenylmethylamino, 2-chloro-N$^1$-p-tolylbenzene-1,4-diamine, 2-chloroaniline, 4-methoxyaniline, methylamine, piperidine, 2-methylaniline, 2,4-difluoroaniline, 2-methoxyaniline, N-methylaniline, 2-amino naphthalene, 2-amino pyridine, (S)-α-methylbenzylamine, 2,4-difluorobenzylamine, 3-chloro-4-(3-fluorobenzyloxy)aniline, cyclohexylamine, 4-biphenylamine, 4-phenoxyaniline, 2,3-difluoroaniline, dimethylamine, 2-trifluoromethylaniline, 1-phenylurea, 2-nitrileaniline, 3,4-dichloro-2-fluoro-N-methylaniline, 2-morpholinaniline, 1,2,3,4-tetrahydroquinoline, 2,3-dihydro-1H-inden-5-amine, 5-aminoquinoline, 6-aminoquinoline, 8-aminoquinoline, 1H-indazol-5-amine, 1-aminonaphthalene, acetamide, 4-fluoroaniline, 4-chloroaniline, 3-ethynylaniline, 3-chloroaniline, 3-methoxyaniline, 2,4-dichloroaniline, 2,6-difluoroaniline, 2,6-dichloro-3,5-dimethoxyaniline, 4-(4-ethylpiperazin-1-yl)aniline, benzamide, 4-dimethylaminoaniline, 4-diethylaminoaniline, 4-(pyrrolidin-1-yl)aniline, 4-(piperidin-1-yl)aniline, 4-(4-methylpiperazin-1-yl)aniline, 3-chloro-4-(4-ethylpiperazin-1-yl)aniline, 3-fluoro-4-(4-ethylpiperazin-1-yl)aniline, 4-(4-ethylpiperazin-1-yl)-3-(trifluoromethyl)aniline, N-(4-aminophenyl)acetamide, 4-aminopyridine, 4-amino-N-methylbenzamide, N-(4-aminophenyl)benzamide, N-(3-amino-4-chlorophenyl)acetamide, 1-(2-fluorophenyl)urea, 2,3-dichloroaniline, 2-bromo-4-fluoroaniline, 2-chloropyridin-3-amine, 2-chloro-N1,N1-diethylbenzene-1,4-diamine, 2-phenylethanamine, 3,5-dichloro-4-(pyridin-2-ylmethoxy)aniline, 3-chloro-4-(4-(cyclopropylmethyl)piperazin-1-yl)aniline, 3-chloro-4-(4-isopropylpiperazin-1-yl)aniline, 3-chloro-4-(4-propylpiperazin-1-yl)aniline, 3-chloro-4-(pyrrolidin-1-yl)aniline, 3-chloro-4-(pyridin-2-ylmethoxy)aniline, 3-chloro-4-(piperidin-1-yl)aniline, 3-chloro-4-morpholinoaniline, 3-fluoro-4-(piperidin-1-yl)aniline, 4-((1H-imidazol-1-yl)methyl)aniline, 4-((4-methylpiperazin-1-yl)sulfonyl)aniline, 4-([1,4'-bipiperidine]-1'-yl)aniline, 4-(1-methylpiperidin-3-yl)aniline, 4-(1-methylpiperidin-4-yl)aniline, 4-(1H-imidazol-1-yl)aniline, 4-(2-propyn-1-yloxy)aniline, 4-(4-(1-methylpiperidin-4-yl)piperazin-1-yl)aniline, 4-(4-(cyclopropylmethyl)piperazin-1-yl)-3-fluoroaniline, 4-(4-methylpiperidin-1-yl)cyclohexanamine, 4-(piperidin-1-ylmethyl)aniline, 4-morpholinoaniline, 4-bromo-2-chloroaniline, 4-bromo-3-chloro-2-fluoroaniline, 5-aminoindolin-2-one, 6-(prop-2-yn-1-yloxy)pyridin-3-amine, 6-chloropyridin-3-amine, 7-amino-2-methyl-4H-chromen-4-one, cyclohexylmethanamine, 4-(4-(4-methylpiperazin-1-yl)piperidin-1-yl)aniline, 3-chloro-4-(4-methylpiperazin-1-yl)aniline and N-(4-((3-fluoro-4-(4-methylpiperazin-1-yl)aniline.

11. The compound of claim 1, which is selected from the group consisting of:

1) (S)—N-(4-(3-chloro-2,4-difluorophenylamino)-7-methoxyquinazolin-6-yl)-1-((S)-3,3-dimethyl-2-((S)-2-(methylamino)propanamido)butanoyl)pyrrolidine-2-carboxamide;

2) (S)—N-(4-(3-chloro-2-fluorophenylamino)-7-(2-methoxyethoxy)quinazolin-6-yl)-1-((S)-3,3-dimethyl-2-((S)-2-(methylamino)propanamido)butanoyl)pyrrolidine-2-carboxamide;

3) (S)—N-(4-(5-chlorobenzo[d][1,3]dioxol-4-ylamino)-7-(2-methoxyethoxy)quinazolin-6-yl)-1-((S)-3,3-dimethyl-2-((S)-2-(methylamino)propanamido)butanoyl)pyrrolidine-2-carboxamide;

4) (S)—N-(4-(3-chloro-2-fluorophenylamino)quinazolin-6-yl)-1-((S)-3,3-dimethyl-2-((S)-2-(methylamino)propanamido)butanoyl)pyrrolidine-2-carboxamide;

5) (S)—N-(4-(3-chloro-4-fluorophenylamino)-7-(2-methoxyethoxy)quinazolin-6-yl)-1-((S)-3,3-dim ethyl-2-((S)-2-(methylamino)propanamido)butanoyl)pyrrolidine-2-carboxamide;

6) (S)—N-(4-(3-chloro-2,4-difluorophenylamino)-7-(2-methoxyethoxy)quinazolin-6-yl)-1-((S)-3,3-dimethyl-2-((S)-2-(methylamino)propanamido)butanoyl)pyrrolidine-2-carboxamide;

7) (S)—N-(4-(3-chloro-2-fluorophenylamino)-7-(2-methoxyethoxy)quinazolin-6-yl)-1-((S)-3,3-dimethyl-2-((S)-2-(methylamino)propanamido)butanoyl)pyrrolidine-2-carboxamide;

8) (S)—N-(4-(3,4-dichloro-2-fluorophenylamino)-7-methoxyquinazolin-6-yl)-1-((S)-3,3-dimethyl-2-((S)-2-(methylamino)propanamido)butanoyl)pyrrolidine-2-carboxamide;

9) (S)—N-(4-(4-bromo-2-fluorophenylamino)-7-methoxyquinazolin-6-yl)-1-((S)-3,3-dimethyl-2-((S)-2-(methylamino)propanamido)butanoyl)pyrrolidine-2-carboxamide;

10) (S)-1-((S)-3,3-dimethyl-2-((S)-2-(methylamino)propanamido)butanoyl)-N-(4-(2-fluorophenylamino)-7-methoxyquinazolin-6-yl)pyrrolidine-2-carboxamide;

11) (S)—N-(4-phenylamino-7-methoxyquinazolin-6-yl)-1-((S)-3,3-dimethyl-2-((S)-2-(methylamino)propanamido)butanoyl)pyrrolidine-2-carboxamide;

12) (S)-1-((S)-2-((S)-2-aminopropanamido)-3,3-dimethylbutanoyl)-N-(4-(3-chloro-2,4-difluorophenylamino)-7-methoxyquinazolin-6-yl)pyrrolidine-2-carboxamide;

13) (S)-1-((S)-2-((S)-2-acrylamidopropanamido)-3,3-dimethylbutanoyl)-N-(4-(3-chloro-2,4-difluorophenylamino)-7-methoxyquinazolin-6-yl)pyrrolidine-2-carboxamide;

14) (S)—N-(4-(3-chloro-2,4-difluorophenylamino)-7-((S)-tetrahydrofuran-3-yloxy)quinazolin-6-yl)-1-((S)-3,3-dimethyl-2-((S)-2-(methylamino)propanamido)butanoyl)pyrrolidine-2-carboxamide;

15) (S)—N-(4-(3-chloro-2,4-difluorophenylamino)-7-methoxyquinazolin-6-yl)-1-((S)-2-cyclohexyl-2-((S)-2-(methylamino)propanamido)acetyl)pyrrolidine-2-carboxamide;

16) (S)—N-(4-(3-chloro-2,4-difluorophenylamino)-7-((R)-tetrahydrofuran-3-yloxy)quinazolin-6-yl)-1-((S)-3,3-dimethyl-2-((S)-2-(methylamino)propanamido)butanoyl)pyrrolidine-2-carboxamide;

17) (S)-1-((S)-3,3-dimethyl-2-((S)-2-(methylamino)propanamido)butanoyl)-N (7-methoxy-4-(2,3,4-trifluorophenylamino)quinazolin-6-yl)pyrrolidine-2-carboxamide;

18) (S)—N-(4-benzylamino-7-methoxyquinazolin-6-yl)-1-((S)-3,3-dimethyl-2-((S)-2-(methylamino)propanamido)butanoyl)pyrrolidine-2-carboxamide;

19) (S)—N-(4-(3-chloro-4-(6-methylpyridin-3-yloxy)phenylamino)-7-methoxyquinazolin-6-yl)-1-((S)-3,3-dimethyl-2-((S)-2-(methylamino)propanamido)butanoyl)pyrrolidine-2-carboxamide;

20) (S)—N-(4-(3-chloro-2,4-difluorophenylamino)-7-methoxyquinazolin-6-yl) 1-((S)-3,3-dimethyl-2-((S)-2-(methylamino)propanamido)butanoyl)azetidine-2-carboxamide;

21) (S)—N-(4-(2-chlorophenylamino)-7-methoxyquinazolin-yl)-1-((S)-3,3-dimethyl-2-((S)-2-(methylamino)propanamido)butanoyl)pyrrolidine-2-carboxamide;

22) (S)—N-(4-(2-bromophenylamino)-7-methoxyquinazolin-6-yl)-1-((S)-3,3-dimethyl-2-((S)-2-(methylamino)propanamido)butanoyl)pyrrolidine-2-carboxamide;

23) (S)-1-((S)-3,3-dimethyl-2-((S)-2-(methylamino)propanamido)butanoyl)-N (7-methoxy-4-(methylamino)quinazolin-6-yl)pyrrolidine-2-carboxamide;

24) (S)-1-((S)-3,3-dimethyl-2-((S)-2-(methylamino)propanamido)butanoyl)-N (7-methoxy-4-(piperidin-1-yl)quinazolin-6-yl)pyrrolidine-2-carboxamide;

25) (S)—N-(4-(3-chloro-2,4-difluorophenylamino)-7-methoxyquinazolin-6-yl)-1-((S)-3,3-dimethyl-2-((S)-2-(methylamino)propanamido)butanoyl)azetidine-2-carboxamide;

26) (S)—N-(4-(3-chloro-2,4-difluorophenylamino)-7-methoxyquinazolin-6-yl)-1-((S)-3,3-dimethyl-2-((S)-2-(methylamino)propanamido)butanoyl)piperidin-3-carboxamide;

27) (S)—N-(4-(o-toluidino)-7-methoxyquinazolin-6-yl)-1-((S)-3,3-dimethyl-2-((S)-2-(methylamino)propanamido)butanoyl)pyrrolidine-2-carboxamide;

28) (S)—N-(4-(2,4-difluorophenylamino)-7-methoxyquinazolin-6-yl)-1-((S)-3,3-dimethyl-2-((S)-2-(methylamino)propanamido)butanoyl)pyrrolidine-2-carboxamide;

29) (S)—N-(4-(4-chloro-2-fluorophenylamino)-7-methoxyquinazolin-6-yl)-1-((S)-3,3-dimethyl-2-((S)-2-(methylamino)propanamido)butanoyl)pyrrolidine-2-carboxamide;

30) (S)—N-(4-(2-methoxyphenylamino)-7-methoxyquinazolin-6-yl)-1-((S)-3,3-dimethyl-2-((S)-2-(methylamino)propanamido)butanoyl)pyrrolidine-2-carboxamide;

31) (S)-1-((S)-3,3-dimethyl-2-((S)-2-(methylamino)propanamido)butanoyl)-N-(7-methoxy-4-(methyl(phenyl)amino)quinazolin-6-yl)pyrrolidine-2-carboxamide;

32) (S)-1-((S)-3,3-dimethyl-2-((S)-2-(methylamino)propanamido)butanoyl)-N-(7-methoxy-4-(naphthalen-2-ylamino)quinazolin-6-yl)pyrrolidine-2-carboxamide;

33) (S)-1-((S)-3,3-dimethyl-2-((S)-2-(methylamino)propanamido)butanoyl)-N-(7-methoxy-4-(pyridin-2-ylamino)quinazolin-6-yl)pyrrolidine-2-carboxamide;

34) (S)-1-((S)-3,3-dimethyl-2-((S)-2-(methylamino)propanamido)butanoyl)-N-(7-methoxy-4-((S)-1-phenylmethylamino)quinazolin-6-yl)pyrrolidine-2-carboxamide;

35) (S)—N-(4-(2,4-difluorobenzylamino)-7-methoxyquinazolin-6-yl)-1-((S)-3,3-dimethyl-2-((S)-2-(methylamino)propanamido)butanoyl)pyrrolidine-2-carboxamide;

36) (S)—N-(4-amino-7-methoxyquinazolin-6-yl)-1-((S)-3,3-dimethyl-2-((S)-2-(methylamino)propanamido)butanoyl)pyrrolidine-2-carboxamide;

37) (S)—N-(4-(3-chloro-4-(3-fluorobenzyloxy)phenylamino)-7-methoxyquinazolin-6-yl)-1-((S)-3,3-dimethyl-2-((S)-2-(methylamino)propanamido)butanoyl)pyrrolidine-2-carboxamide;

38) (S)—N-(4-(cyclohexylamino)-7-methoxyquinazolin-6-yl)-1-((S)-3,3-dimethyl-2-((S)-2-(methylamino)propanamido)butanoyl)pyrrolidine-2-carboxamide;

39) (S)—N-(4-(biphenyl-4-ylamino)-7-methoxyquinazolin-6-yl)-1-((S)-3,3-dimethyl-2-((S)-2-(methylamino)propanamido)butanoyl)pyrrolidine-2-carboxamide;

40) (S)-1-((S)-3,3-dimethyl-2-((S)-2-(methylamino)propanamido)butanoyl)-N-(7-methoxy-4-(4-phenoxyphenylamino)quinazolin-6-yl)pyrrolidine-2-carboxamide;

41) (S)—N-(4-(3-chloro-4-fluorophenylamino)-7-methoxyquinazolin-6-yl)-1-((S)-3,3-dimethyl-2-((S)-2-(methylamino)propanamido)butanoyl)pyrrolidine-2-carboxamide;

42) (S)—N-(4-(2,3-difluorophenylamino)-7-methoxyquinazolin-6-yl)-1-((S)-3,3-dimethyl-2-((S)-2-(methylamino)propanamido)butanoyl)pyrrolidine-2-carboxamide;

43) (S)—N-(4-(3-chloro-2,4-difluorophenylamino)-7-hydroxyquinazolin-6-yl)-1-((S)-3,3-dimethyl-2-((S)-2-(methylamino)propanamido)butanoyl)pyrrolidine-2-carboxamide;

44) (S)—N—((S)-1-((S)-2-(4-((4-bromo-2-fluorophenylamino)-6-methoxyquinazolinyl-7-oxy)methyl)piperidine)-1-carbonyl)-1-pyrrolidinyl)-3,3-dimethyloxobutan-2-yl)-2-(methylamino)propanamide;

45) (S)—N-(4-(3-chloro-2,4-difluorophenylamino)-7-methoxyquinazolin-6-yl)-1-((2S,3R)-2-((S)-2-(methylamino)propanamido)-3-(prop-2-ynyloxy)butanoyl)pyrrolidine-2-carboxamide;

46) (2S,4R)-4-(benzyloxy)-N-(4-(3-chloro-2,4-difluorophenylamino)-7-methoxyquinazolin-6-yl)-1-((S)-3,3-dimethyl-2-((S)-2-(methylamino)propanamido)butanoyl)pyrrolidine-2-carboxamide;

47) (S)-1-((S)-3,3-dimethyl-2-((S)-2-(methylamino)propanamido)butanoyl)-N (7-methoxy-4-(2-morpholinophenylamino)quinazolin-6-yl)pyrrolidine-2-carboxamide;
48) (S)—N-(4-(3-chloro-2,4-difluorophenylamino)quinazolin-6-yl)-1-((S)-3,3-dimethyl-2-((S)-2-(methyamino)propanamido)butanoy)pyrrolidine-2-carboxamide;
49) (S)-1-((S)-3,3-dimethyl-2-((S)-2-(methylamino)propanamido)butanoyl)-N (7-methoxy-4-(4-methoxyphenylamino)quinazolin-6-yl)pyrrolidine-2-carboxamide;
50) (S)—N-(4-(3,4-dihydroquinoline-1(2H)-yl)-7-methoxyquinazolin-6-yl)-1-((S)-3,3-dimethyl-2-((S)-2-(methylamino)propanamido)butanoyl)pyrrolidine-2-carboxamide;
51) (S)—N-(4-(5-chlorobenzo[d][1,3]dioxol-4-ylamino)-7-methoxyquinazolin-6-yl)-1-((S)-3,3-dimethyl-2-((S)-2-(methylamino)propanamido)butanoyl)pyrrolidine-2-carboxamide;
52) (S)—N-(4-(2,3-dihydro-1H-inden-5-ylamino)-7-methoxyquinazolin-6-yl)-1-((S)-3,3-dimethyl-2-((S)-2-(methylamino)propanamido)butanoyl)pyrrolidine-2-carboxamide;
53) (S)-1-((S)-3,3-dimethyl-2-((S)-2-(methylamino)propanamido)butanoyl)-N (7-methoxy-4-(quinoline-6-ylamino)quinazolin-6-yl)pyrrolidine-2-carboxamide;
54) (S)—N-(4-(1H-indazol-5-ylamino)-7-methoxyquinazolin-6-yl)-1-((S)-3,3-dimethyl-2-((S)-2-(methylamino)propanamido)butanoyl)pyrrolidine-2-carboxamide;
55) (S)-1-((S)-3,3-dimethyl-2-((S)-2-(methylamino)propanamido)butanoyl)-N-(4-(4-fluorophenylamino)-7-methoxyquinazolin-6-yl)pyrrolidine-2-carboxamide;
56) (S)—N-(4-(4-chlorophenylamino)-7-methoxyquinazolin-6-yl)-1-((S)-3,3-dimethyl-2-((S)-2-(methylamino)propanamido)butanoyl)pyrrolidine-2-carboxamide;
57) (S)-1-((S)-3,3-dimethyl-2-((S)-2-(methylamino)propanamido)butanoyl)-N (7-methoxy-4-(3-methoxyphenylamino)quinazolin-6-yl)pyrrolidine-2-carboxamide;
58) (S)—N-(4-(2,4-dichlorophenylamino)-7-methoxyquinazolin-6-yl)-1-((S)-3,3-dimethyl-2-((S)-2-(methylamino)propanamido)butanoyl)pyrrolidine-2-carboxamide;
59) (S)—N-(4-(2,6-difluorophenylamino)-7-methoxyquinazolin-yl)-1-((S)-3,3-dimethyl-2-((S)-2-(methylamino)propanamido)butanoyl)pyrrolidine-2-carboxamide;
60) (S)-1-((S)-3,3-dimethyl-2-((S)-2-(methylamino)propanamido)butanoyl)-N-(4-(4-(4-ethylpiperazin-1-yl)phenylamino)-7-methoxyquinazolin-6-yl)pyrrolidine-2-carboxamide;
61) (S)—N-(4-(benzo[d][1,3]dioxol-5-ylamino)-7-methoxyquinazolin-6-yl)-1-((S)-3,3-dimethyl-2-((S)-2-(methylamino)propanamido)butanoyl)pyrrolidine-2-carboxamide;
62) (S)-1-((S)-3,3-dimethyl-2-((S)-2-(methylamino)propanamido)butanoyl)-N (7-methoxy-4-(quinoline-3-ylamino)quinazolin-6-yl)pyrrolidine-2-carboxamide;
63) (S)-1-((S)-3,3-dimethyl-2-((S)-2-(methylamino)propanamido)butanoyl)-N (7-methoxy-4-(quinoline-5-ylamino)quinazolin-6-yl)pyrrolidine-5-carboxamide;
64) (S)-1-((S)-3,3-dimethyl-2-((S)-2-(methylamino)propanamido)butanoyl)-N (7-methoxy-4-(4-dimethylamino)phenylamino)quinazolin-6-yl)pyrrolidine-2-carboxamide;
65) (S)-1-((S)-3,3-dimethyl-2-((S)-2-(methylamino)propanamido)butanoyl)-N (7-methoxy-4-(4-(pyrrolidin-1-yl)phenylamino)quinazolin-6-yl)pyrrolidine-2-carboxamide;
66) (S)-1-((S)-3,3-dimethyl-2-((S)-2-(methylamino)propanamido)butanoyl)-N-(7-methoxy-4-(4-(piperidin-1-yl)phenylamino)quinazolin-6-yl)pyrrolidine-2-carboxamide;
67) (S)-1-((S)-3,3-dimethyl-2-((S)-2-(methylamino)propanamido)butanoyl)-N-(7-methoxy-4-(4-(4-methylpiperazin-1-yl)phenylamino)quinazolin-6-yl)pyrrolidine-2-carboxamide;
68) (S)-1-((S)-3,3-dimethyl-2-((S)-2-(methylamino)propanamido)butanoyl)-N-(7-methoxy-4-(4-diethylamino)phenylamino)quinazolin-6-yl)pyrrolidine-2-carboxamide;
69) (S)—N-(4-(4-acetamidophenylamino)-7-methoxyquinazolin-6-yl)-1-((S)-3,3-dimethyl-2-((S)-2-(methylamino)propanamido)butanoyl)pyrrolidine-2-carboxamide;
70) (S)-1-((S)-3,3-dimethyl-2-((S)-2-(methylamino)propanamido)butanoyl)-N-(4-(4-(4-ethylpiperazin-1-yl)-3-(trifluoromethyl)phenylamino)-7-methoxyquinazolin-6-yl)pyrrolidine-2-carboxamide;
71) (S)-1-((S)-3,3-dimethyl-2-((S)-2-(methylamino)propanamido)butanoyl)-N-(4-(4-(4-ethylpiperazin-1-yl)-3-fluorophenylamino)-7-methoxyquinazolin-6-yl)pyrrolidine-2-carboxamide;
72) (S)—N-(4-((1,1-dioxide-4-thiomorpholinyl)phenylamino)-7-methoxyquinazolin-6-yl)-1-((S)-3,3-dimethyl-2-((S)-2-(methylamino)propanamido)butanoyl)pyrrolidine-2-carboxamide;
73) (S)-1-((S)-3,3-dimethyl-2-((S)-2-(methylamino)propanamido)butanoyl)-N-(7-methoxy-4-(pyridin-4-ylamino)quinazolin-6-yl)pyrrolidine-2-carboxamide;
74) (S)-1-((S)-3,3-dimethyl-2-((S)-2-(methylamino)propanamido)butanoyl)-N-(7-methoxy-4-(4-(methylcarbamoyl)phenylamino)quinazolin-6-yl)pyrrolidine-2-carboxamide;
75) (S)—N-(4-(5-acetamino-2-chlorophenylamino)-7-methoxyquinazolin-6-yl)-1-((S)-3,3-dimethyl-2-((S)-2-(methylamino)propanamido)butanoyl)pyrrolidine-2-carboxamide;
76) (S)—N-(4-(4-benzamidophenylamino)-7-methoxyquinazolin-6-yl)-1-((S)-3,3-dimethyl-2-((S)-2-(methylamino)propanamido)butanoyl)pyrrolidine-2-carboxamide;
77) (S)—N-(4-(cyclohexylmethyl)amino)-7-methoxyquinazolin-6-yl)-1-((S)-3,3-dimethyl-2-((S)-2-(methylamino)propanamido)butanoyl)pyrrolidine-2-carboxamide;
78) (S)—N-(4-((2-chloropyridin-3-yl)amino)-7-methoxyquinazolin-6-yl)-1-((S)-3,3-dimethyl-2-((S)-2-(methylamino)propanamido)butanoyl)pyrrolidine-2-carboxamide;
79) (S)—N-(4-((6-chloropyridin-3-yl)amino)-7-methoxyquinazolin-6-yl)-1-((S)-3,3-dimethyl-2-((S)-2-(methylamino)propanamido)butanoyl)pyrrolidine-2-carboxamide;
80) (S)—N-(4-((4-bromo-2-chlorophenyl)amino)-7-methoxyquinazolin-6-yl)-1-((S)-3,3-dimethyl-2-((S)-2-(methylamino)propanamido)butanoyl)pyrrolidine-2-carboxamide;
81) (S)—N-(4-((2,3-dichlorophenyl)amino)-7-methoxyquinazolin-6-yl)-1-((S)-3,3-dimethyl-2-((S)-2-(methylamino)propanamido)butanoyl)pyrrolidine-2-carboxamide;

82) (S)—N-(4-((2-bromo-4-fluorophenyl)amino)-7-methoxyquinazolin-6-yl)-1-((S)-3,3-dimethyl-2-((S)-2-(methylamino)propanamido)butanoyl)pyrrolidine-2-carboxamide;

83) (S)-1-((S)-3,3-dimethyl-2-((S)-2-(methylamino)propanamido)butanoyl)-N-(7-methoxy-4-(phenylamino)quinazolin-6-yl)pyrrolidine-2-carboxamide;

84) (S)-1-((S)-3,3-dimethyl-2-((S)-2-(methylamino)propanamido)butanoyl)-N-(7-methoxy-4-((6-(prop-2-yn-1-yloxy)pyridin-3-yl)amino)quinazolin-6-yl)pyrrolidine-2-carboxamide;

85) (S)-1-((S)-3,3-dimethyl-2-((S)-2-(methylamino)propanamido)butanoyl)-N-(4-((3-fluoro-4-(piperidin-1-yl)phenyl)amino)-7-methoxyquinazolin-6-yl)pyrrolidine-2-carboxamide;

86) (S)—N-(4-((3-chloro-4-(4-methylpiperazin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;

87) (S)—N-(4-((4-bromo-3-chloro-2-fluorophenyl)amino)-7-methoxyquinazolin-6-yl)-1-((S)-3,3-dimethyl-2-((S)-2-(methylamino)propanamido)butanoyl)pyrrolidine-2-carboxamide;

88) (S)—N-(4-((4-(1H-imidazol-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;

89) (S)-1-((S)-3,3-dimethyl-2-((S)-2-(methylamino)propanamido)butanoyl)-N (4-(3-(2-fluorophenyl)ureido)-7-methoxyquinazolin-6-yl)pyrrolidine-2-carboxamide;

90) (S)-1-((S)-3,3-dimethyl-((S)-2-(methylamino)propanamido)butanoyl)-N-(7-methoxy-4-((4-morpholinophenyl)amino)quinazolin-6-yl)pyrrolidine-2-carboxamide;

91) (S)-1-((S)-3,3-dimethyl-2-((S)-2-(methylamino)propanamide)butanoyl)-N (7-methoxy-4-((4-(2-propyn-1-yloxy)phenyl)amino)quinazolin-6-yl)pyrrolidine-2-carboxamide;

92) (S)—N-(4-((3-chloro-4-(4-(cyclopropylmethyl)piperazin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;

93) (S)-1-((S)-3,3-dimethyl-2-((S)-2-(methylamino)propanamide)butanoyl)-N (7-methoxy-4-((2-methyl-4-oxo-4H-chromen-7-yl)amino)quinazolin-6-yl)pyrrolidine-2-carboxamide;

94) (S)-1-((S)-3,3-dimethyl-2-((S)-2-(methylamino)propanamide)butanoyl)-N-(7-methoxy-4-((2-oxoindolin-5-yl)amino)quinazolin-6-yl)pyrrolidine-2-carboxamide;

95) (S)—N-(4-((3-chloro-4-morpholinophenyl)amino)-7-methoxyquinazolin-6-yl)-1-((S)-3,3-dimethyl-2-((S)-2-(methylamino)propanamido)butanoyl)pyrrolidine-2-carboxamide;

96) (S)—N-(4-((3-chloro-4-(piperidin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;

97) (S)—N-(4-((3-chloro-4-(isopropylpiperazin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;

98) (S)—N-(4-((3-chloro-4-(4-propyl-1-yl)phenyl)amino)-7-methoxyquinazolin-6-yl)-1-((S)-3,3-dimethyl-2-((S)-2-(methylamino)propanamido)butanoyl)pyrrolidine-2-carboxamide;

99) (S)—N-(4-((3-chloro-4-(diethylamino)phenyl)amino)-7-methoxyquinazolin-6-yl)-1-((S)-3,3-dimethyl-2-((S)-2-(methylamino)propanamido)butanoyl)pyrrolidine-2-carboxamide;

100) (S)—N-(4-((4-(4-(cyclopropylmethyl)piperazin-1-yl)-3-fluorophenyl)amino)-7-methoxyquinazolin-6-yl)-1-((S)-3,3-dimethyl-2-((S)-2-(methylamino)propanamido)butanoyl)pyrrolizine-2-carboxamide;

101) (S)—N-(4-((3,5-dichloro-4-(pyridin-2-ylmethoxy)phenyl)amino)-7-methoxyquinazolin-6-yl)-1-((S)-3,3-dimethyl-2-((S)-2-(methylamino)propanamido)butanoyl)pyrrolidine-2-carboxamide;

102) (S)—N-(4-((3-chloro-4-(pyridin-2-ylmethoxy)phenyl)amino)-7-methoxyquinazolin-6-yl)-1-((S)-3,3-dimethyl-2-((S)-2-(methylamino)propanamido)butanoyl)pyrrolidine-2-carboxamide;

103) (S)—N-(4-((4-([1,4'-bipiperidine]-1'-yl)phenyl)amino)-7-methoxyquinazolin-6-yl)-1-((S)-3,3-dimethyl-2-((S)-2-(methylamino)propanamido)butanoyl)pyrrolidine-2-carboxamide;

104) (S)-1-((S)-3,3-dimethyl-2-((S)-2-(methylamino)propanamido)butanoyl)-N-(7-methoxy-4-((4-(piperidin-1-ylmethyl)phenyl)amino)quinazolin-6-yl)pyrrolidine-2-carboxamide;

105) (S)-1-((S)-3,3-dimethyl-2-((S)-2-(methylamino)propanamido)butanoyl)-N-(7-methoxy-4-((4-(4-(4-methylpiperazin-1-yl)piperidin-1-yl)phenyl)amino)quinazolin-6-yl)pyrrolidine-2-carboxamide;

106) (S)-1-((S)-3,3-dimethyl-2-((S)-2-(methylamino)propanamido)butanoyl)-N-(7-methoxy-4-((4-(1-methylpiperidin-4-yl)phenyl)amino)quinazolin-6-yl)pyrrolidine-2-carboxamide;

107) (S)-1-((S)-3,3-dimethyl-2-((S)-2-(methylamino)propanamido)butanoyl)-N-(7-methoxy-4-((4-(4-methylpiperidin-1-yl)cyclohexyl)amino)quinazolin-6-yl)pyrrolidine-2-carboxamide;

108) (S)-1-((S)-3,3-dimethyl-2-((S)-2-(methylamino)propanamido)butanoyl)-N-(7-methoxy-4-((4-((4-methylpiperazin-1-yl)sulfonyl)phenyl)amino)quinazolin-6-yl)pyrrolidine-2-carboxamide;

109) (2S)-1-((S)-3,3-dimethyl-2-((S)-2-(methylamino)propanamido)butanoyl)-N-(7-methoxy-4-((4-(1-methylpiperidin-3-yl)phenyl)amino)quinazolin-6-yl)pyrrolidine-2-carboxamide;

110) (S)-1-((S)-3,3-dimethyl-2-((S)-2-(methylamino)propanamido)butanoyl)-N-(7-methoxy-4-((4-(4-(1-methylpiperidin-4-yl)piperazin-1-yl)phenyl)amino)quinazolin-6-yl)pyrrolizine-2-carboxamide;

111) (S)—N-(4-((4-((1H-imidazol-1-yl)methyl)phenyl)amino)-7-methoxyquinazolin-6-yl)-1-((S)-3,3-dimethyl-2-((S)-2-(methylamino)propanamido)butanoyl)pyrrolidine-2-carboxamide;

112) (S)-1-((S)-3,3-dimethyl-2-((S)-2-(methylamino)propanamido)butanoyl)-N-(4-((3-fluoro-4-(4-methylpiperazin-1-yl)phenyl)amino)-7-methoxyquinazolin-6-yl)pyrrolidine-2-carboxamide; and 113) (S)—N-(4-((3-chloro-4-(pyrrolidin-1-yl)phenyl)amino)-7-methoxyquinazolin-6-yl)-1-((S)-3,3-dimethyl-2-((S)-2-(methylamino)propanamido)butanoyl)pyrrolidine-2-carboxamide.

12. A pharmaceutical composition comprising the compound of claim 1 and a pharmaceutically acceptable carrier.

13. A compound library comprising two or more of the compounds of claim 1.

14. A method for treating breast cancer or pancreas cancer in a subject, which comprises administrating the compound of claim 1 to the subject in need thereof.

* * * * *

SEQUENCE LISTING

<160> NUMBER OF SEQ ID NOS: 3

<210> SEQ ID NO 1
<211> LENGTH: 29
<212> TYPE: DNA
<213> ORGANISM: Artificial Sequence
<220> FEATURE:
<223> OTHER INFORMATION: forward primer for XIAP BIR3

<400> SEQUENCE: 1
cgcggatcct ctgatgctgt gagttctga                                29

<210> SEQ ID NO 2
<211> LENGTH: 30
<212> TYPE: DNA
<213> ORGANISM: Artificial Sequence
<220> FEATURE:
<223> OTHER INFORMATION: reverse primer for XIAP BIR3

<400> SEQUENCE: 2
gagcctcgag ctaagtagtt cttaccagac                               30

<210> SEQ ID NO 3
<211> LENGTH: 116
<212> TYPE: PRT
<213> ORGANISM: Artificial Sequence
<220> FEATURE:
<223> OTHER INFORMATION: Synthetic construct of XIAP BIR3 domain

<400> SEQUENCE: 3

Ser Asp Ala Val Ser Ser Asp Arg Asn Phe Pro Asn Ser Thr Asn Leu
 1               5                  10                  15

Pro Arg Asn Pro Ser Met Ala Asp Tyr Glu Ala Arg Ile Phe Thr Phe
             20                  25                  30

Gly Thr Trp Ile Tyr Ser Val Asn Lys Glu Gln Leu Ala Arg Ala Gly
         35                  40                  45

Phe Tyr Ala Leu Gly Glu Gly Asp Lys Val Lys Cys Phe His Cys Gly
     50                  55                  60

Gly Gly Leu Thr Asp Trp Lys Pro Ser Glu Asp Pro Trp Glu Gln His
 65                  70                  75                  80

Ala Lys Trp Tyr Pro Gly Cys Lys Tyr Leu Leu Glu Gln Lys Gly Gln
                 85                  90                  95

Glu Tyr Ile Asn Asn Ile His Leu Thr His Ser Leu Glu Glu Cys Leu
            100                 105                 110

Val Arg Thr Thr
        115